United States Patent
Zawistoski et al.

(10) Patent No.: US 9,771,327 B2
(45) Date of Patent: Sep. 26, 2017

(54) COMPOUNDS AND METHODS FOR THE TREATMENT OF CYSTIC FIBROSIS

(71) Applicant: FLATLEY DISCOVERY LAB, LLC, Charlestown, MA (US)

(72) Inventors: Michael P. Zawistoski, West Warwick, RI (US); Yevgen Barsukov, Brookline, MA (US); Bridget M. Cole, Quincy, MA (US); Richard A. Nugent, Ashland, MA (US)

(73) Assignee: FLATLEY DISCOVERY LAB, LLC, Charlestown, MA (US)

( * ) Notice: Subject to any disclaimer, the term of this patent is extended or adjusted under 35 U.S.C. 154(b) by 0 days.

(21) Appl. No.: 14/210,232

(22) Filed: Mar. 13, 2014

(65) Prior Publication Data

US 2014/0371263 A1 Dec. 18, 2014

Related U.S. Application Data

(60) Provisional application No. 61/778,883, filed on Mar. 13, 2013.

(51) Int. Cl.
| | | |
|---|---|---|
| *C07D 405/14* | (2006.01) | |
| *A61K 31/4468* | (2006.01) | |
| *C07D 211/96* | (2006.01) | |
| *A61K 31/437* | (2006.01) | |
| *C07D 471/04* | (2006.01) | |
| *C07D 401/12* | (2006.01) | |
| *A61K 31/454* | (2006.01) | |
| *A61K 31/4545* | (2006.01) | |
| *A61K 31/497* | (2006.01) | |
| *A61K 31/506* | (2006.01) | |
| *A61K 45/06* | (2006.01) | |
| *C07D 401/14* | (2006.01) | |
| *C07D 413/12* | (2006.01) | |

(Continued)

(52) U.S. Cl.
CPC ........ *C07D 211/96* (2013.01); *A61K 31/4245* (2013.01); *A61K 31/437* (2013.01); *A61K 31/443* (2013.01); *A61K 31/4468* (2013.01); *A61K 31/454* (2013.01); *A61K 31/4525* (2013.01); *A61K 31/4545* (2013.01); *A61K 31/4725* (2013.01); *A61K 31/497* (2013.01); *A61K 31/506* (2013.01); *A61K 31/7036* (2013.01); *A61K 45/06* (2013.01); *C07D 401/12* (2013.01); *C07D 401/14* (2013.01); *C07D 405/14* (2013.01); *C07D 413/12* (2013.01); *C07D 417/12* (2013.01); *C07D 471/04* (2013.01)

(58) Field of Classification Search
CPC .. C07D 211/96; C07D 401/12; C07D 401/14; C07D 413/12; C07D 417/12; C07D 471/04; C07D 405/14

USPC ........ 546/118, 194, 198, 209, 224; 544/333, 544/327, 405
See application file for complete search history.

(56) References Cited

U.S. PATENT DOCUMENTS

| | | | |
|---|---|---|---|
| 7,244,744 B2 | 7/2007 | Gross et al. | |
| 7,879,880 B2 * | 2/2011 | Solomon | C07D 213/73 514/234.5 |

(Continued)

FOREIGN PATENT DOCUMENTS

| | | |
|---|---|---|
| WO | 96/33196 A1 | 10/1996 |
| WO | 96/35713 A1 | 11/1996 |

(Continued)

OTHER PUBLICATIONS

Chemcats 1060420-23-6 (2008).*

(Continued)

*Primary Examiner* — Celia Chang
(74) *Attorney, Agent, or Firm* — Elmore Patent Law Group, P.C.; Edgar Harlan; Carolyn Elmore

(57) ABSTRACT

The invention relates to a compound of Formula I and methods of treating CFTR (cystic fibrosis transmembrane conductance regulator) mediated diseases, in particular cystic fibrosis, comprising the step of administering a therapeutically effective amount of a compound of Formula I or IA to a patient in need thereof:

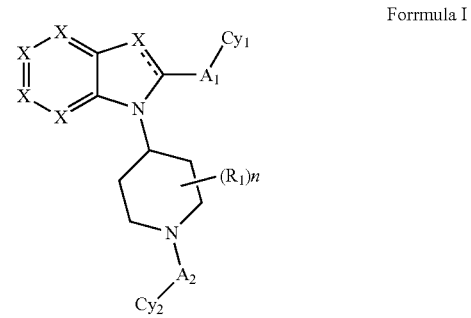

Forrmula I

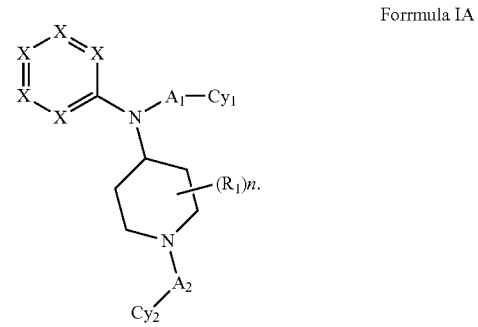

Forrmula IA

15 Claims, No Drawings

(51) Int. Cl.
C07D 417/12 (2006.01)
A61K 31/4245 (2006.01)
A61K 31/443 (2006.01)
A61K 31/4525 (2006.01)
A61K 31/4725 (2006.01)
A61K 31/7036 (2006.01)

(56) References Cited

U.S. PATENT DOCUMENTS

| | | | | |
|---|---|---|---|---|
| 8,741,933 | B2* | 6/2014 | Hadida Ruah et al. | 514/338 |
| 2004/0156859 | A1 | 8/2004 | Ezrin et al. | |
| 2009/0105274 | A1 | 4/2009 | Kugimiya et al. | |
| 2010/0144591 | A1 | 6/2010 | Aslanian et al. | |
| 2012/0095037 | A1 | 4/2012 | Winfield | |

FOREIGN PATENT DOCUMENTS

| | | |
|---|---|---|
| WO | 03/037890 A2 | 5/2003 |
| WO | 2007/069053 A1 | 6/2007 |
| WO | 2007/076055 A2 | 7/2007 |
| WO | 2011/086053 A1 | 7/2011 |

OTHER PUBLICATIONS

Chemcats 1069738-26-6 (2008).*
Chemcats 1066974-48-8 (2008).*
Chemcats 1270844-98-8 (2011).*
Chemcats 1281510-90-4 (2011).*
Chemcats 1283140-71-5 (2011).*
Carpino et al. "Preparation of htereocyclic . . . " CA126:60362 (1997).*
Kugimiva et al. "Preparation of indole . . . " CA146:316774 (2007).*
AGN-PC-07RWCQ—PubChem (2007).*
Anticipatory compounds Chemcats 1270844-98-3, 1281510-90-4 or 1283140-71-5, X=CR100, R100=H, halogen or substituted alkyl, A1=absent, Cy1=alkyl, A2 is absent, Cy2=alky; Kugimiya et al. CA146 or Carpino et al. CA126; Chemcats 1060420-23-6, 1069738-26-6 or 1066974-48-8 (Exhibit I) (2009).*
AGN-PC-07RWCL—PubChem (2007).*
AGN-PC-07RWCU—PubChem (2007).*
AGN-PC-07RWD0—PubChem (2007).*
Gross et al. "Preparationof 4-(benzimidao . . . " ca138:368892 (2003).*
Chemical Library, Wikipedia p. 1-3 (2015).*
Lodhi et al. "Chemoinformatics . . . " p. 60-61 (2011).*
Pubchem. CID 2980394. Jul. 30, 2005, pp. 1-4 [online], [retrieved on Jun. 6, 2014]. Retrieved from the Internet <URL: http://pubchem.ncbi.nlm.nih.gov/summary/summary.cgi?cid=2980394&loc=ec_rcs>.
Ipubchem. CID 68279240. Dec. 1, 2012, pp. 1-3 [online], [retrieved on Jun. 6, 2014]. Retrieved from the Internet <URL: http://pubchem.ncbi.nlm.nih.gov/summary/summary.cgi?cid=68279240&loc=ec_rcs>.
Pubchem. CID 46286853. Jul. 21, 2010, pp. 1-3 [online], [retrieved on Jun. 6, 2014]. Retrieved from the Internet <URL: http://pubchem.ncbi.nlm.nih.gov/summary/summary.cgi?cid=46286853&loc=ec_rcs>.
CAS RN: 1114623-88-9; 1114608-29-5; 1111418-15-5; 1111314-69-2; 1111314-68-1; 1111257-34-1; 1111163-35-9; 1111163-34-8; 1111163-33-7; 1111163-32-6; 1111163-31-5; 1111047-66-5; 1111047-62-1; 1111047-58-5; 1111010-39-9; 1111010-29-7; 1111010-24-2; 1110972-45-6; 1070752-32-7; 1069907-31-8; 1069868-05-8; 1069846-71-4; 1069826-72-7; 1069739-62-3; 1069704-08-0; 1069611-78-4; 1065562-89-1 1065509-21-8; 1065501-62-3; 1060957-23-4; 1060823-65-5; 1060469-44-4; 1060443-41-5 downloaded from STN file Registry.
Chemcats RN 1281510-90-4 (2011).
Chemcats RN 1283140-71-5 (2011).
Carpino, P., A., et al., "Preparation of heterocyclic dipeptide derivatives which promote release of growth hormone," CA126:60362 (1997).
Kugimiya, A., et al., "Preparation of indole-carboxylic acids and related compounds receptor antagonistic activity," CA146:316774 (2007).
Chemcats RN 1060420-23-6 (2008).
Chemcats RN 1270844-98-3 (2011).
Chemcats RN 1069738-26-6 (2008).
Chemcats RN 1066974-48-8 (2008).
King, F. D., Bioisoteres, Conformational Restriction, and Prodrugs—Case History: An Example of Conformational Restriction Approach, Ch. 14 in Med. Chem: Principle & Practice: 206-209 (1994).
Hilfiker, et al., "Optimization of a Novel Series of TRPV4 Antagonists with In Vivo Activity in a Model of Pulmonary Edema," ACS Medicinal Chemistry Letters, 4(2): 293-296 (2013).

* cited by examiner

COMPOUNDS AND METHODS FOR THE TREATMENT OF CYSTIC FIBROSIS

RELATED APPLICATION

This application claims the benefit of U.S. Provisional Application No. 61/778,883, filed on Mar. 13, 2013. The entire teachings of the above application are incorporated herein by reference.

BACKGROUND

Cystic fibrosis (CF) is a lethal, recessive, genetic disease affecting approximately 1 in 2500 live births among Caucasians. (Cohen-Cymberknoh, M et. al., *Am. J. Respir. Crit. Care Med.* 1463-1471, 2011; Boat et al., The Metabolic Basis of Inherited Disease, 6th ed, pp 2649-2680, McGraw Hill, NY (1989)). Approximately 1 in 25 persons are carriers of the disease. The major symptoms of cystic fibrosis include chronic pulmonary disease, pancreatic exocrine insufficiency, and elevated sweat electrolyte levels. The symptoms are consistent with cystic fibrosis being an exocrine disorder. (Hantash F: U.S. Patent Application No. 20060057593).

The CF gene codes for a cAMP/PKA-dependent, ATP-requiring, membrane chloride ion channel, generally found in the apical membranes of many secreting epithelia and known as CFTR (cystic fibrosis transmembrane conductance regulator). There are currently over 1700 known mutations affecting CFTR, many of which give rise to a disease phenotype. Around 75% of CF alleles contain the ΔF508 mutation in which a triplet codon has been lost, leading to a missing phenylalanine at position 508 in the protein. This altered protein fails to be trafficked to the correct location in the cell and is generally destroyed by the proteasome. The small amount that does reach the correct location functions poorly. (Cuthbert A W, *British Journal of Pharmacology,* 163(1), 173-183, 2011).

Mutations in the CFTR gene result in absence or dysfunction of the protein that regulates ion transport across the apical membrane at the surface of certain epithelia. Although CFTR functions mainly as a chloride channel, it has many other roles, including inhibition of sodium transport through the epithelial sodium channel, regulation of the outwardly rectifying chloride channel, ATP channels, intracellular vesicle transport, and inhibition of endogenous calcium-activated chloride channels. CFTR is also involved in bicarbonate-chloride exchange. A deficiency in bicarbonate secretion leads to poor solubility and aggregation of luminal mucins. Obstruction of intrapancreatic ducts with thickened secretions causes autolysis of pancreatic tissue with replacement of the body of the pancreas with fat, leading to pancreatic insufficiency with subsequent malnutrition. In the lungs, CFTR dysfunction leads to airway surface liquid (ASL) depletion and thickened and viscous mucus that adheres to airway surfaces. The result is decreased mucociliary clearance (MCC) and impaired host defenses. Dehydrated, thickened secretions lead to endobronchial infection with a limited spectrum of distinctive bacteria, mainly *Staphylococcus aureus* and *Pseudomonas aeruginosa*, and an exaggerated inflammatory response leading to development of bronchiectasis and progressive obstructive airways disease. Pulmonary insufficiency is responsible for most CF-related deaths. (Cohen-Cymberknoh, M et. al., *Am. J. Respir. Crit. Care Med.* 1463-1471, 2011).

The prognosis for the treatment of CF has improved over the last 40 years. This was achieved by improving pancreatic enzyme supplements, drugs designed to treat pulmonary infection, reduce inflammation and enhance mucociliary clearance. Currently the therapeutic challenges are to correct the biochemical defect of CF and to identify effective treatments for chronic respiratory infection. (Frerichs C. et. al., *Expert Opin Pharmacother.* 10(7), 1191-202, 2009).

SUMMARY

The invention relates to a compound of Formula I and methods of treating CFTR (cystic fibrosis transmembrane conductance regulator) mediated diseases, in particular cystic fibrosis, comprising the step of administering a therapeutically effective amount of a compound of Formula I or IA to a patient in need thereof:

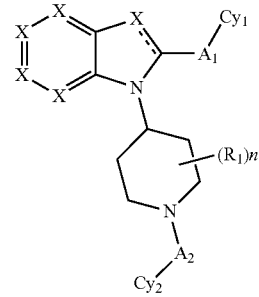

Formula I

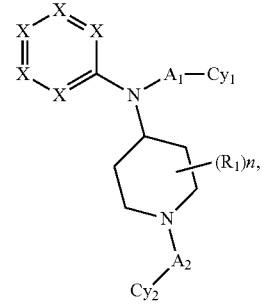

Formula IA wherein n is 0, 1, 2, 3, 4, 5, 6 or 7;
each X is independently selected from $-CR_{100}-$ or $-N-$;
$A_1$ is absent, $-[C(R_{100})(R_{101})]_m-C(O)-$, $-C(S)-$, $-S(O)-$, $-C(O)N(R_{100})-$, $-S(O)_2N(R_{100})(R_{101})$ or $-S(O)_2-$;
wherein m is 0, 1, 2, 3, 4, 5, 6 or 7;
wherein each $R_{100}$ and $R_{101}$ is hydrogen, deuterium, halogen, alkyl, cycloalkyl, substituted alkyl, alkenyl, substituted alkenyl, alkynyl, substituted alkynyl, aliphatic, substituted aliphatic, aryl and substituted aryl, heterocycle, substituted heterocycle, heteroaryl or substituted heteroaryl;
alternatively, two of $R_{100}$ and $R_{101}$ groups together with the atoms to which they are attached and any intervening atoms may form an additional optionally substituted, 3, 4, 5, 6 or 7 membered ring;
$A_2$ is absent, $-[C(R_{100})(R_{101})]_m-C(O)-$, $-C(S)-$, $-S(O)-$, $-C(O)N(R_{100})-$, $-S(O)_2N(R_{100})(R_{101})$ or $-S(O)_2-$;
each $R_1$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —OR$_{100}$, —SR$_{100}$, —S(O)—, S(O)$_2$—, —S(O)$_2$N(R$_{100}$)(R$_{101}$)—NR$_{100}$R$_{101}$, —C(O)R$_{100}$, —C(O)OR$_{100}$, —C(O)NR$_{100}$R$_{101}$, —N(R$_{100}$)C(O)R$_{101}$, —CF$_3$, —CN, —NO$_2$, —N$_3$, acyl, alkoxy, substituted alkoxy, alkylamino, substituted alkylamino, dialkylamino, substituted dialkylamino, alkylthio or substituted alkylthio; alternatively two of R$_1$ groups together with the atoms to which they are attached and any intervening atoms may form an additional optionally substituted 3, 4, 5, 6 or 7 membered ring;

Cy$_1$ is absent, alkyl, cycloalkyl, substituted cycloalkyl, aryl, substituted aryl, heteroaryl or substituted heteroaryl;

Cy$_2$ is alkyl, cycloalkyl, substituted cycloalkyl, aryl, substituted aryl, heteroaryl or substituted heteroaryl.

DETAILED DESCRIPTION OF THE INVENTION

The invention relates to a compound of Formula I and methods of treating cystic fibrosis comprising the step of administering a therapeutically effective amount of a compound of Formula I or IA to a patient in need thereof:

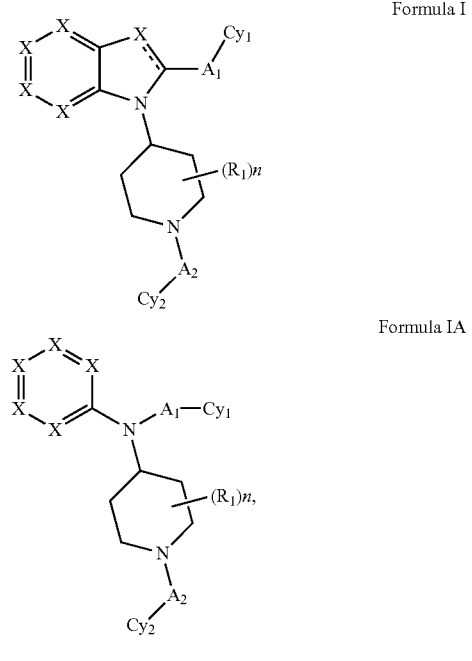

Formula I

Formula IA wherein n is 0, 1, 2, 3, 4, 5, 6 or 7;
each X is independently selected from —CR$_{100}$— or —N—;
A$_1$ is absent, —[C(R$_{100}$)(R$_{101}$)]$_m$—C(O)—, —C(S)—, —S(O)—, —C(O)N(R$_{100}$)— or —S(O)$_2$—, —S(O)$_2$N(R$_{100}$)(R$_{101}$);
wherein m is 0, 1, 2, 3, 4, 5, 6 or 7;
wherein each R$_{100}$ and R$_{101}$ is hydrogen, deuterium, halogen, alkyl, cycloalkyl, substituted alkyl, alkenyl, substituted alkenyl, alkynyl, substituted alkynyl, aliphatic, substituted aliphatic, aryl and substituted aryl, heterocycle, substituted heterocycle, heteroaryl or substituted heteroaryl;
alternatively, two of R$_{100}$ and R$_{101}$ groups together with the atoms to which they are attached and any intervening atoms may form an additional optionally substituted, 3, 4, 5, 6 or 7 membered ring;

A$_2$ is absent, —[C(R$_{100}$)(R$_{101}$)]$_m$—C(O)—, —C(S)—, —S(O)—, —C(O)N(R$_{100}$)— or —S(O)$_2$—, —S(O)$_2$N(R$_{100}$)(R$_{101}$);

each R$_1$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —OR$_{100}$, —SR$_{100}$, —S(O)—, S(O)$_2$—, —S(O)$_2$N(R$_{100}$)(R$_{101}$)—NR$_{100}$R$_{101}$, —C(O)R$_{100}$, —C(O)OR$_{100}$, —C(O)NR$_{100}$R$_{101}$, —N(R$_{100}$)C(O)R$_{101}$, —CF$_3$, —CN, —NO$_2$, —N$_3$, acyl, alkoxy, substituted alkoxy, alkylamino, substituted alkylamino, dialkylamino, substituted dialkylamino, alkylthio or substituted alkylthio;

alternatively two of R$_1$ groups together with the atoms to which they are attached and any intervening atoms may form an additional optionally substituted 3, 4, 5, 6 or 7 membered ring;

Cy$_1$ is absent, alkyl, cycloalkyl, substituted cycloalkyl, aryl, substituted aryl, heteroaryl or substituted heteroaryl;

Cy$_2$ is alkyl, cycloalkyl, substituted cycloalkyl aryl, substituted aryl, heteroaryl or substituted heteroaryl.

In a preferred embodiment, the invention relates to a compound having the Formula II or IIA:

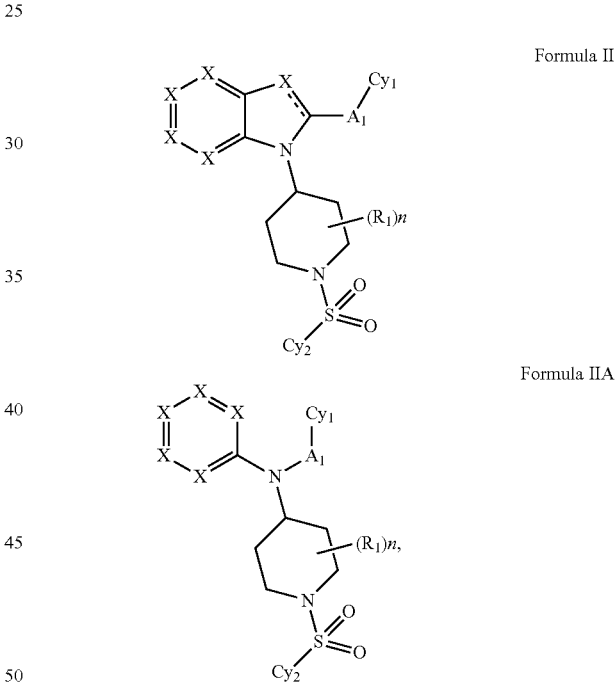

Formula II

Formula IIA wherein n is 0, 1, 2, 3, 4, 5, 6 or 7;
each X is independently selected from —CR$_{100}$— or —N—;
A$_1$ is absent, —[C(R$_{100}$)(R$_{101}$)]$_m$—C(O)—, —C(S)—, —S(O)—, —C(O)N(R$_{100}$)— or —S(O)$_2$—, —S(O)$_2$N(R$_{100}$)(R$_{101}$);
wherein m is 0, 1, 2, 3, 4, 5, 6 or 7;
wherein each R$_{100}$ and R$_{101}$ is hydrogen, deuterium, halogen, alkyl, cycloalkyl, substituted alkyl, alkenyl, substituted alkenyl, alkynyl, substituted alkynyl, aliphatic, substituted aliphatic, aryl and substituted aryl, heterocycle, substituted heterocycle, heteroaryl or substituted heteroaryl;
alternatively, two of R$_{100}$ and R$_{101}$ groups together with the atoms to which they are attached and any intervening atoms may form an additional optionally substituted, 3, 4, 5, 6 or 7 membered ring;

each $R_1$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —$OR_{100}$, —$SR_{100}$, —S(O)—, $S(O)_2$—, —$S(O)_2N(R_{100})(R_{101})$—$NR_{100}R_{101}$, —$C(O)R_{100}$, —$C(O)OR_{100}$, —$C(O)NR_{100}R_{101}$, —$N(R_{100})C(O)R_{101}$, —$CF_3$, —CN, —$NO_2$, —$N_3$, acyl, alkoxy, substituted alkoxy, alkylamino, substituted alkylamino, dialkylamino, substituted dialkylamino, alkylthio or substituted alkylthio;

Alternatively, two of $R_1$ groups together with the atoms to which they are attached and any intervening atoms may form an additional optionally substituted 3, 4, 5, 6 or 7 membered ring, preferably a cycloalkyl, substituted cycloalkyl, aryl, substituted aryl, heteroaryl or substituted heteroaryl group;

$Cy_1$ is absent, cycloalkyl, substituted cycloalkyl, aryl, substituted aryl, heteroaryl or substituted heteroaryl;

$Cy_2$ is aryl, substituted aryl, heteroaryl or substituted heteroaryl.

In a preferred embodiment, the invention relates to a compound having the Formula III or IIIA:

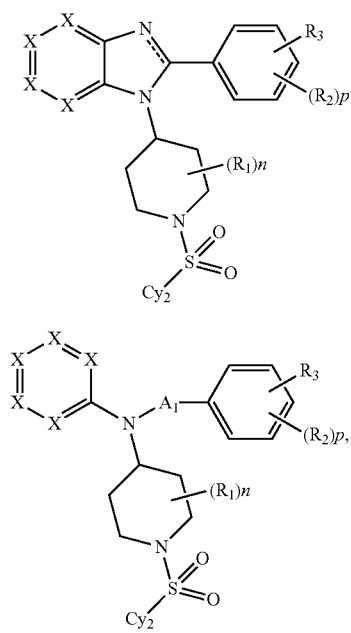

Formula III

Formula IIIA wherein p is 0, 1, 2 or 3;

each $R_2$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —$OR_{100}$, —$SR_{100}$, —S(O)—, $S(O)_2$—, —$S(O)_2N(R_{100})(R_{101})$—$NR_{100}R_{101}$, —$C(O)R_{100}$, —$C(O)OR_{100}$, —$C(O)NR_{100}R_{101}$, —$N(R_{100})C(O)R_{101}$, —$CF_3$, —CN, —$NO_2$, —$N_3$, acyl, alkoxy, substituted alkoxy, alkylamino, substituted alkylamino, dialkylamino, substituted dialkylamino, alkylthio or substituted alkylthio; and $R_3$ is selected from halogen, deuterium, alkyl, substituted alkyl, cycloalkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —$OR_{100}$, —$SR_{100}$, —S(O)—, $S(O)_2$—, —$S(O)_2N(R_{100})(R_{101})$—$NR_{100}R_{101}$, —$C(O)R_{100}$, —$C(O)OR_{100}$, —$C(O)NR_{100}R_{101}$, —$N(R_{100})C(O)R_{101}$, —$CF_3$, —CN, —$NO_2$, —$N_3$, acyl, alkoxy, substituted alkoxy, alkylamino, substituted alkylamino, dialkylamino, substituted dialkylamino, alkylthio or substituted alkylthio;

Alternatively, two of $R_2$ groups or an $R_2$ group with an $R_3$ group together with the atoms to which they are attached and any intervening atoms may form an additional optionally substituted 3, 4, 5, 6 or 7 membered ring, preferably a cycloalkyl, substituted cycloalkyl, aryl, substituted aryl, heteroaryl or substituted heteroaryl group.

In a preferred embodiment, the invention relates to a compound having the Formula IV or IVA:

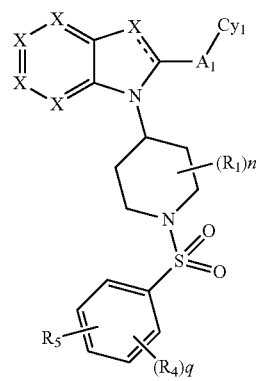

Formula IV

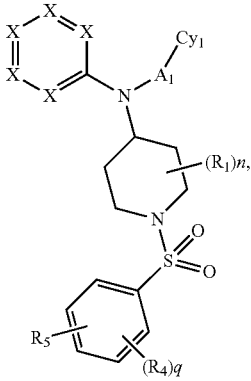

Formula IVA wherein q is 0, 1, 2 or 3;

each $R_4$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —$OR_{100}$, —$SR_{100}$, —S(O)—, $S(O)_2$—, —$S(O)_2N(R_{100})(R_{101})$—$NR_{100}R_{101}$, —$C(O)R_{100}$, —$C(O)OR_{100}$, —$C(O)NR_{100}R_{101}$, —$N(R_{100})C(O)R_{101}$, —$CF_3$, —CN, —$NO_2$, —$N_3$, acyl, alkoxy, substituted alkoxy, alkylamino, substituted alkylamino, dialkylamino, substituted dialkylamino, alkylthio or substituted alkylthio; and $R_5$ is selected from hydrogen, deuterium, halogen, alkyl, substituted alkyl, cycloalkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —OR$_{100}$, —SR$_{100}$, —S(O)—, S(O)$_2$—, —S(O)$_2$N(R$_{100}$)(R$_{101}$)—NR$_{100}$R$_{101}$, —C(O)R$_{100}$, —C(O)OR$_{100}$, —C(O)NR$_{100}$R$_{101}$, —N(R$_{100}$)C(O)R$_{101}$, —CF$_3$, —CN, —NO$_2$, —N$_3$, acyl, alkoxy, substituted alkoxy, alkylamino, substituted alkylamino, dialkylamino, substituted dialkylamino, alkylthio or substituted alkylthio;

alternatively, two of R$_4$ groups or an R$_4$ group with an R$_5$ group together with the atoms to which they are attached and any intervening atoms may form an additional optionally substituted 3, 4, 5, 6 or 7 membered ring, preferably a cycloalkyl, substituted cycloalkyl, aryl, substituted aryl, heteroaryl or substituted heteroaryl group.

In a preferred embodiment, the invention relates to a compound having the Formula V or VA:

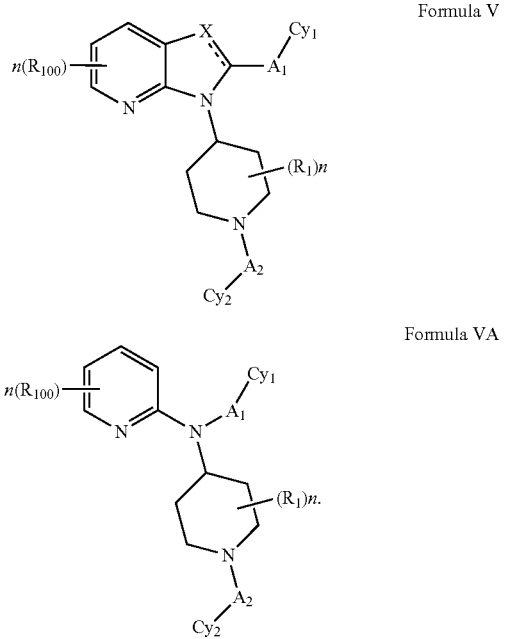

Formula V

Formula VA

In a preferred embodiment, Cy$_1$ is selected from:

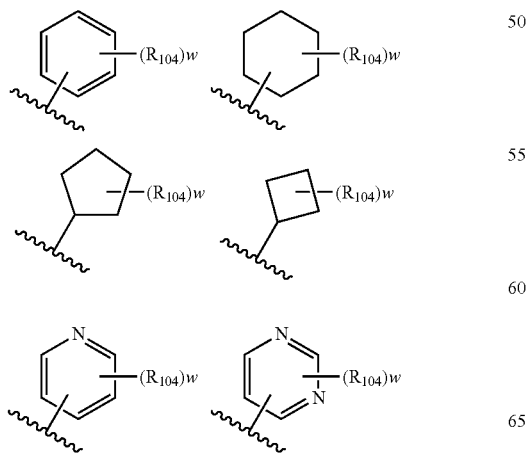

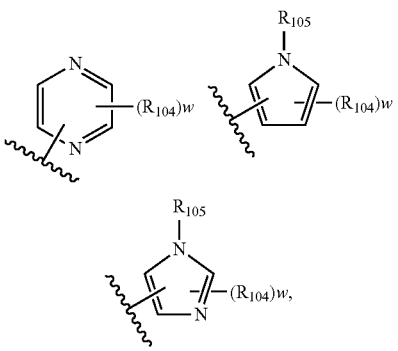

wherein w is 0, 1, 2, 3 or 4;

each R$_{104}$ and R$_{105}$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —OR$_{100}$, —SR$_{100}$, —S(O)—, S(O)$_2$—, —S(O)$_2$N(R$_{100}$)(R$_{101}$)—NR$_{100}$R$_{101}$, —C(O)R$_{100}$, —C(O)OR$_{100}$, —C(O)NR$_{100}$R$_{101}$, —N(R$_{100}$)C(O)R$_{101}$, —CF$_3$, —CN, —NO$_2$, —N$_3$, acyl, alkoxy, substituted alkoxy, alkylamino, substituted alkylamino, dialkylamino, substituted dialkylamino, alkylthio or substituted alkylthio;

alternatively, two of R$_{104}$ groups or an R$_{104}$ group with an R$_{105}$ group together with the atoms to which they are attached and any intervening atoms may form an additional optionally substituted 3, 4, 5, 6 or 7 membered ring, preferably a cycloalkyl, substituted cycloalkyl, aryl, substituted aryl, heteroaryl or substituted heteroaryl group.

In a preferred embodiment, Cy$_2$ is selected from:

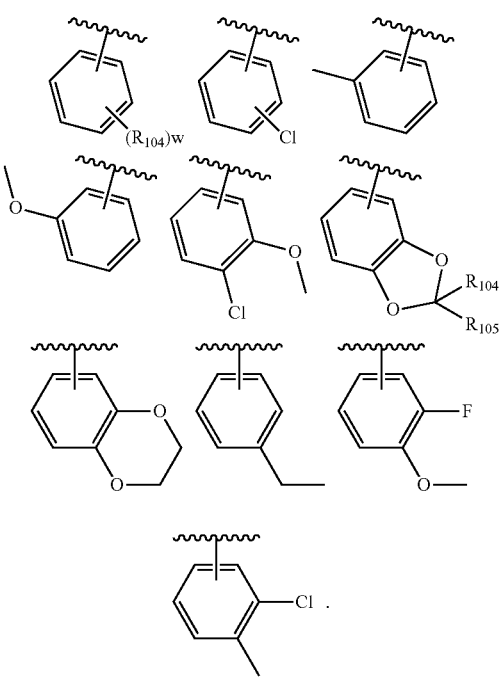

In a more preferred embodiment, a compound of formula I is selected from Table 1:
TABLE 1
| No. | Example No. |
|---|---|
| 1. | Example 16 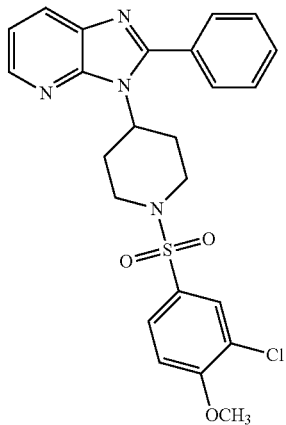 |
| 2. | Example 17 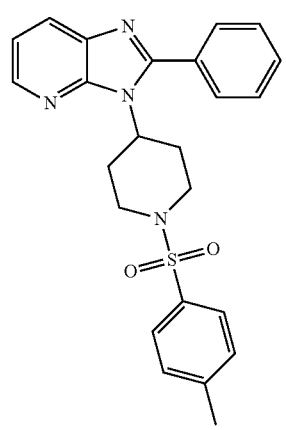 [SMILES: Cc1ccc(S(=O)(=O)N2CCC(n3c(-c4ccccc4)nc4cccnc43)CC2)cc1] |
| 3. | Example 18 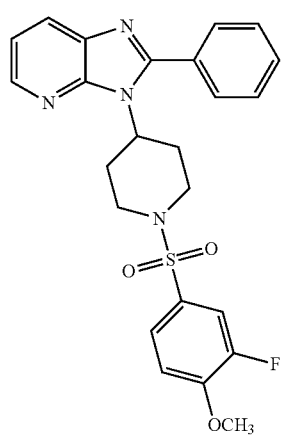 [SMILES: COc1ccc(S(=O)(=O)N2CCC(n3c(-c4ccccc4)nc4cccnc43)CC2)cc1F] |
TABLE 1-continued
| No. | Example No. |
|---|---|
| 4. | Example 19 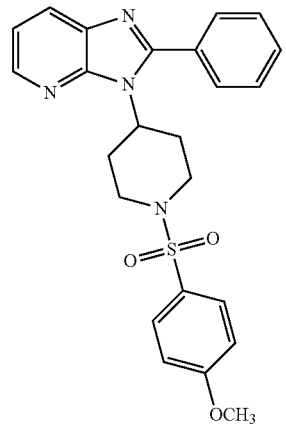 [SMILES: COc1ccc(S(=O)(=O)N2CCC(n3c(-c4ccccc4)nc4cccnc43)CC2)cc1] |
| 5. | Example 20 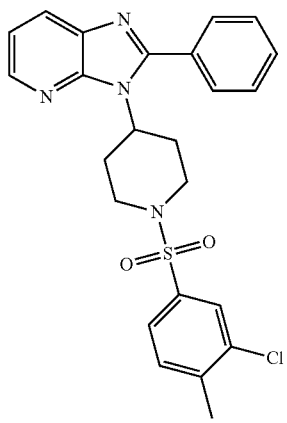 [SMILES: Cc1ccc(S(=O)(=O)N2CCC(n3c(-c4ccccc4)nc4cccnc43)CC2)cc1Cl] |
| 6. | Example 21 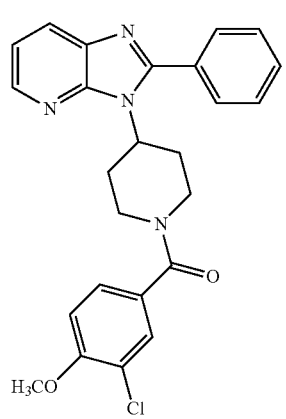 [SMILES: COc1ccc(C(=O)N2CCC(n3c(-c4ccccc4)nc4cccnc43)CC2)cc1Cl] |

TABLE 1-continued
| No. | Example No. |
|---|---|
| 7. | Example 6 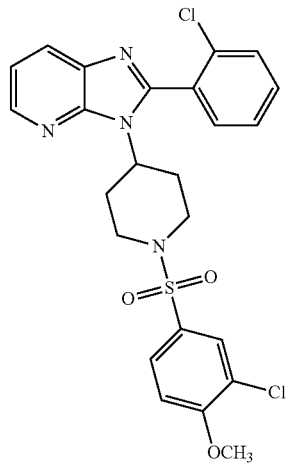 |
| 8. | Example 22 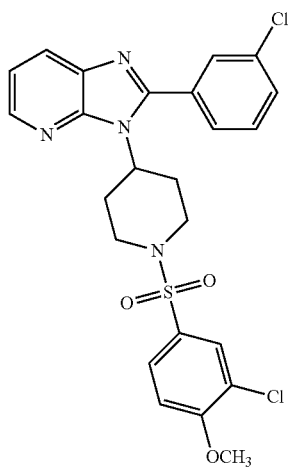 [SMILES: COc1ccc(S(=O)(=O)N2CCC(n3c(-c4cccc(Cl)c4)nc4cccnc43)CC2)cc1Cl] |
| 9. | Example 23 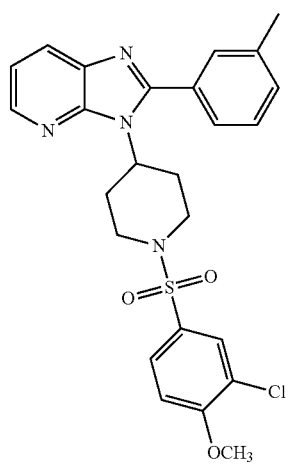 [SMILES: COc1ccc(S(=O)(=O)N2CCC(n3c(-c4cccc(C)c4)nc4cccnc43)CC2)cc1Cl] |
| 10. | Example 24 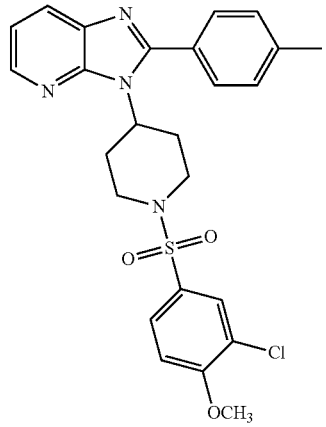 [SMILES: COc1ccc(S(=O)(=O)N2CCC(n3c(-c4ccc(C)cc4)nc4cccnc43)CC2)cc1Cl] |
| 11. | Example 25 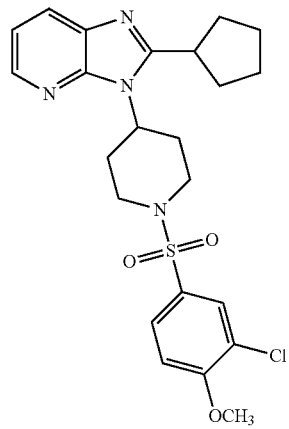 [SMILES: COc1ccc(S(=O)(=O)N2CCC(n3c(C4CCCC4)nc4cccnc43)CC2)cc1Cl] |
| 12. | Example 5 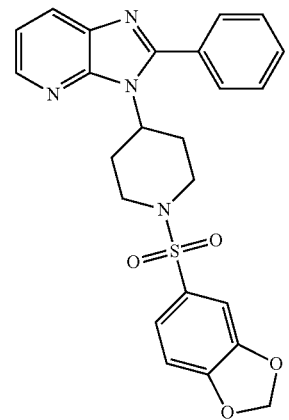 [SMILES: O=S(=O)(c1ccc2c(c1)OCO2)N1CCC(n2c(-c3ccccc3)nc3cccnc32)CC1] |

TABLE 1-continued
| No. | Example No. |
|---|---|
| 13. | Example 26 |
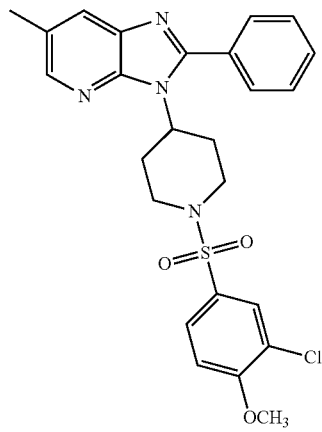
| No. | Example No. |
|---|---|
| 14. | Example 3 |
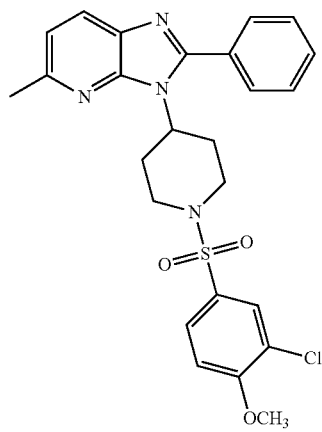
| No. | Example No. |
|---|---|
| 15. | Example 27 |
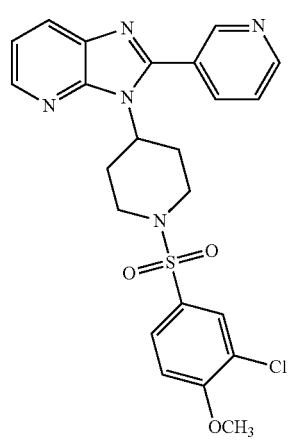 [SMILES: COc1ccc(S(=O)(=O)N2CCC(n3c(-c4cccnc4)nc4cccnc43)CC2)cc1Cl]
| No. | Example No. |
|---|---|
| 16. | Example 28 |
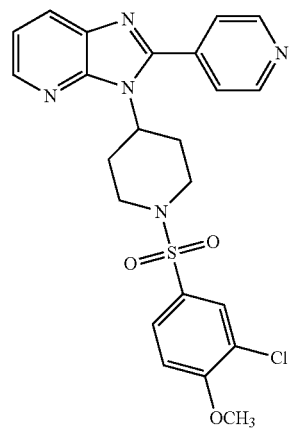 [SMILES: COc1ccc(S(=O)(=O)N2CCC(n3c(-c4ccncc4)nc4cccnc43)CC2)cc1Cl]
| No. | Example No. |
|---|---|
| 17. | Example 29 |
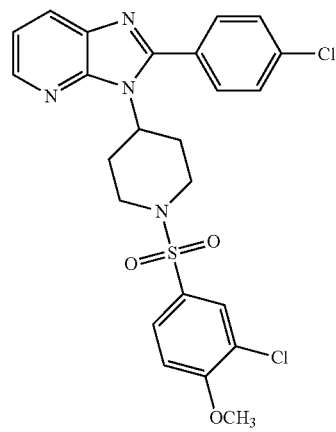 [SMILES: COc1ccc(S(=O)(=O)N2CCC(n3c(-c4ccc(Cl)cc4)nc4cccnc43)CC2)cc1Cl]
| No. | Example No. |
|---|---|
| 18. | Example 30 |
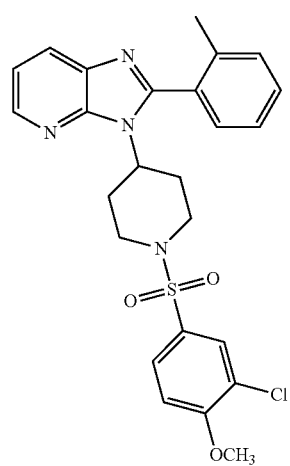 [SMILES: COc1ccc(S(=O)(=O)N2CCC(n3c(-c4ccccc4C)nc4cccnc43)CC2)cc1Cl]

TABLE 1-continued
| No. | Example No. |
|---|---|
| 19. | Example 31 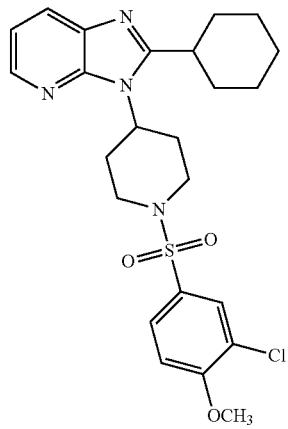 [SMILES: COc1ccc(S(=O)(=O)N2CCC(n3c(C4CCCCC4)nc4cccnc43)CC2)cc1Cl] |
| 20. | Example 32 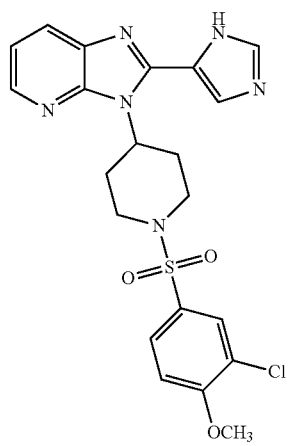 [SMILES: COc1ccc(S(=O)(=O)N2CCC(n3c(-c4cnc[nH]4)nc4cccnc43)CC2)cc1Cl] |
| 21. | Example 33 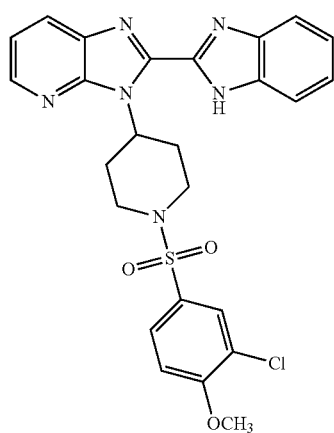 [SMILES: COc1ccc(S(=O)(=O)N2CCC(n3c(-c4nc5ccccc5[nH]4)nc4cccnc43)CC2)cc1Cl] |
| 22. | Example 34 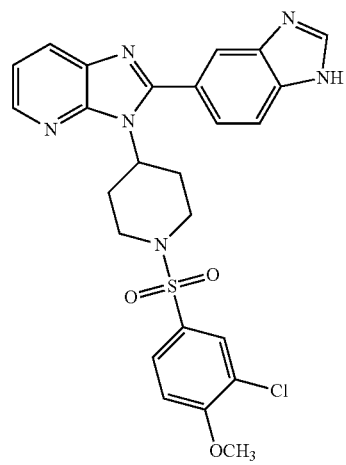 [SMILES: COc1ccc(S(=O)(=O)N2CCC(n3c(-c4ccc5[nH]cnc5c4)nc4cccnc43)CC2)cc1Cl] |
| 23. | Example 35 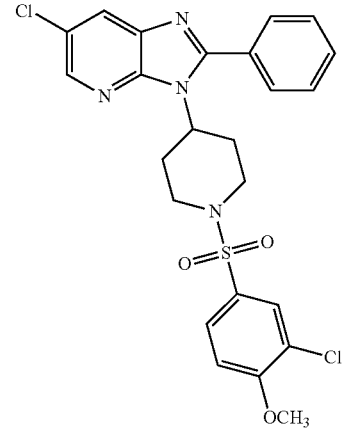 [SMILES: COc1ccc(S(=O)(=O)N2CCC(n3c(-c4ccccc4)nc4cc(Cl)cnc43)CC2)cc1Cl] |
| 24. | Example 36 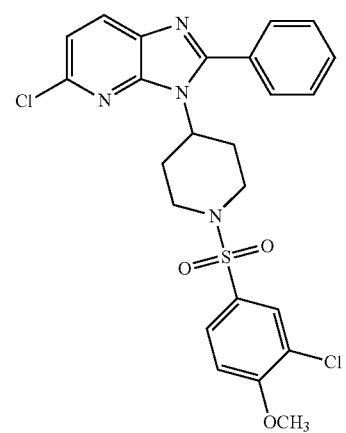 [SMILES: COc1ccc(S(=O)(=O)N2CCC(n3c(-c4ccccc4)nc4ccc(Cl)nc43)CC2)cc1Cl] |

TABLE 1-continued
| No. | Example No. |
|---|---|
| 25. | Example 4 |
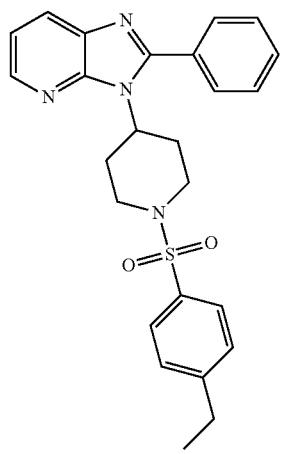 [SMILES: CCc1ccc(S(=O)(=O)N2CCC(n3c(-c4ccccc4)nc4cccnc43)CC2)cc1]
| No. | Example No. |
|---|---|
| 26. | Example 37 |
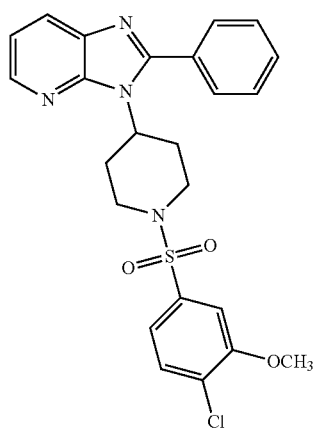 [SMILES: COc1cc(S(=O)(=O)N2CCC(n3c(-c4ccccc4)nc4cccnc43)CC2)ccc1Cl]
| No. | Example No. |
|---|---|
| 27. | Example 2 |
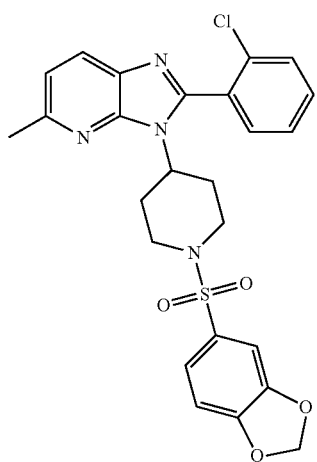 [SMILES: Cc1ccc2nc(-c3ccccc3Cl)n(C3CCN(S(=O)(=O)c4ccc5c(c4)OCO5)CC3)c2n1]
TABLE 1-continued
| No. | Example No. |
|---|---|
| 28. | Example 1 |
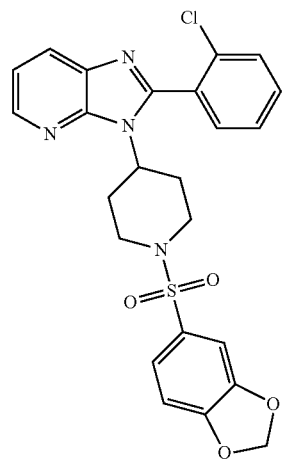 [SMILES: O=S(=O)(c1ccc2c(c1)OCO2)N1CCC(n2c(-c3ccccc3Cl)nc3cccnc32)CC1]
| No. | Example No. |
|---|---|
| 29. | Example 7 |
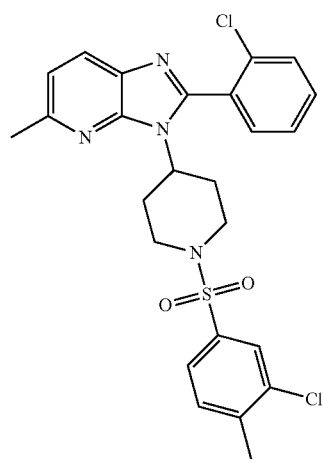 [SMILES: Cc1ccc2nc(-c3ccccc3Cl)n(C3CCN(S(=O)(=O)c4ccc(C)c(Cl)c4)CC3)c2n1]
| No. | Example No. |
|---|---|
| 30. | Example 8 |
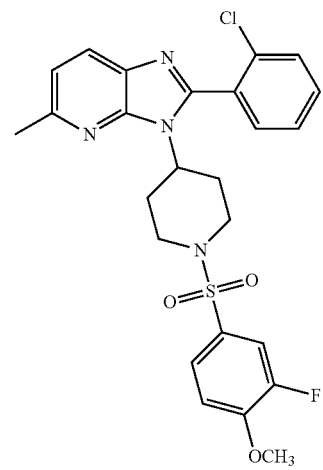 [SMILES: COc1ccc(S(=O)(=O)N2CCC(n3c(-c4ccccc4Cl)nc4ccc(C)nc43)CC2)cc1F]

TABLE 1-continued
| No. | Example No. |
|---|---|
| 31. | Example 9 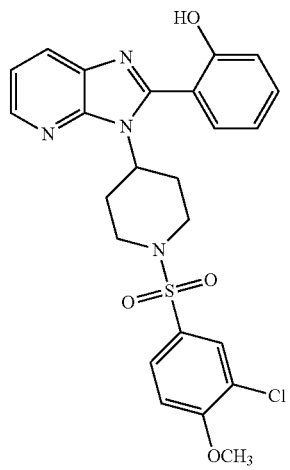 |
| 32. | Example 10 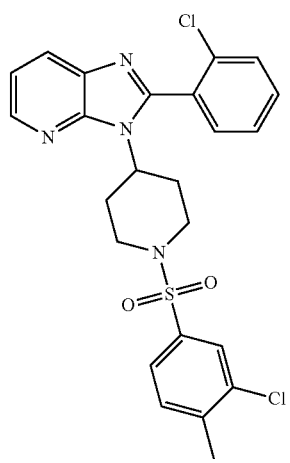 [SMILES: Cc1ccc(S(=O)(=O)N2CCC(n3c(-c4ccccc4Cl)nc4cccnc43)CC2)cc1Cl] |
| 33. | Example 11 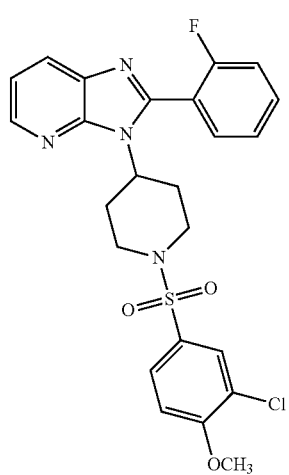 |
| 34. | Example 12 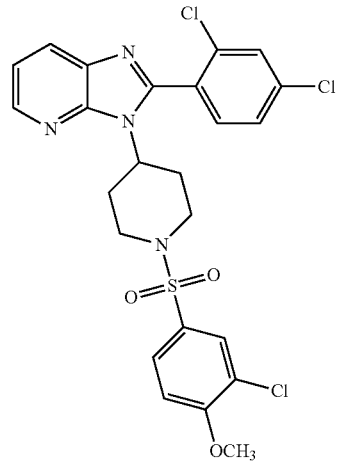 [SMILES: COc1ccc(S(=O)(=O)N2CCC(n3c(-c4ccc(Cl)cc4Cl)nc4cccnc43)CC2)cc1Cl] |
| 35. | Example 13 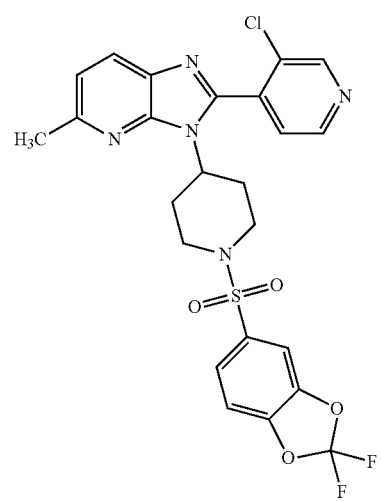 [SMILES: Cc1ccc2nc(-c3ccncc3Cl)n(C3CCN(S(=O)(=O)c4ccc5c(c4)OC(F)(F)O5)CC3)c2n1] |
| 36. | Example 14 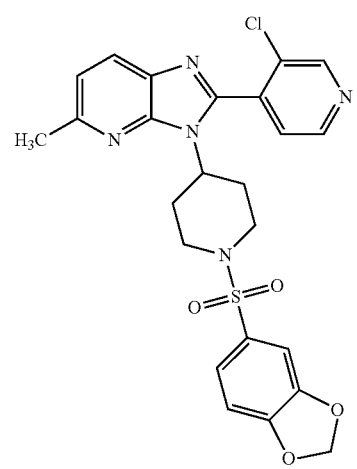 [SMILES: Cc1ccc2nc(-c3ccncc3Cl)n(C3CCN(S(=O)(=O)c4ccc5c(c4)OCO5)CC3)c2n1] |

TABLE 1-continued
| No. | Example No. | |
|---|---|---|
| 37. | Example 15 | 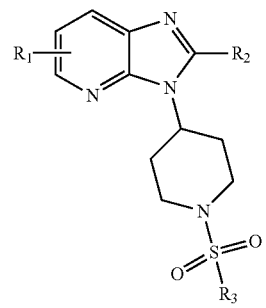 |
General synthetic schemes to prepare compounds of the invention:
SCHEME 1:
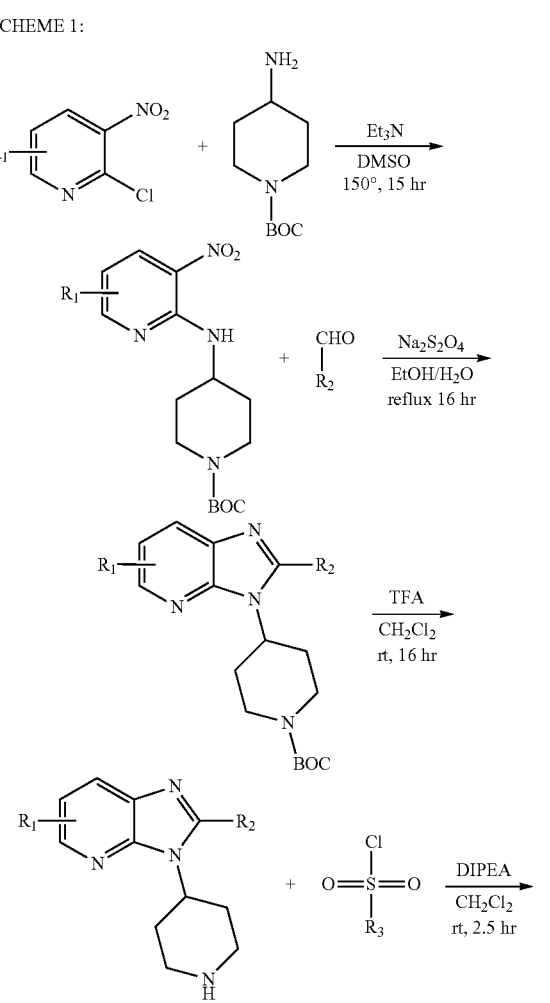
SCHEME 1a:
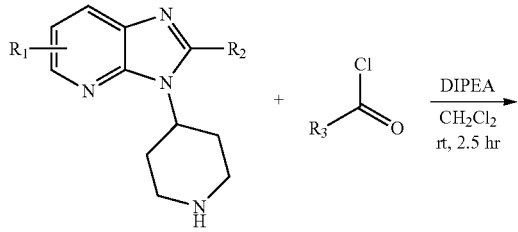
SCHEME 2:
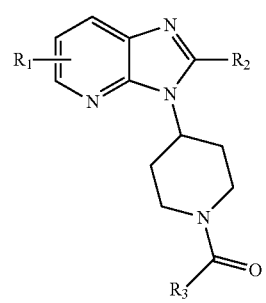

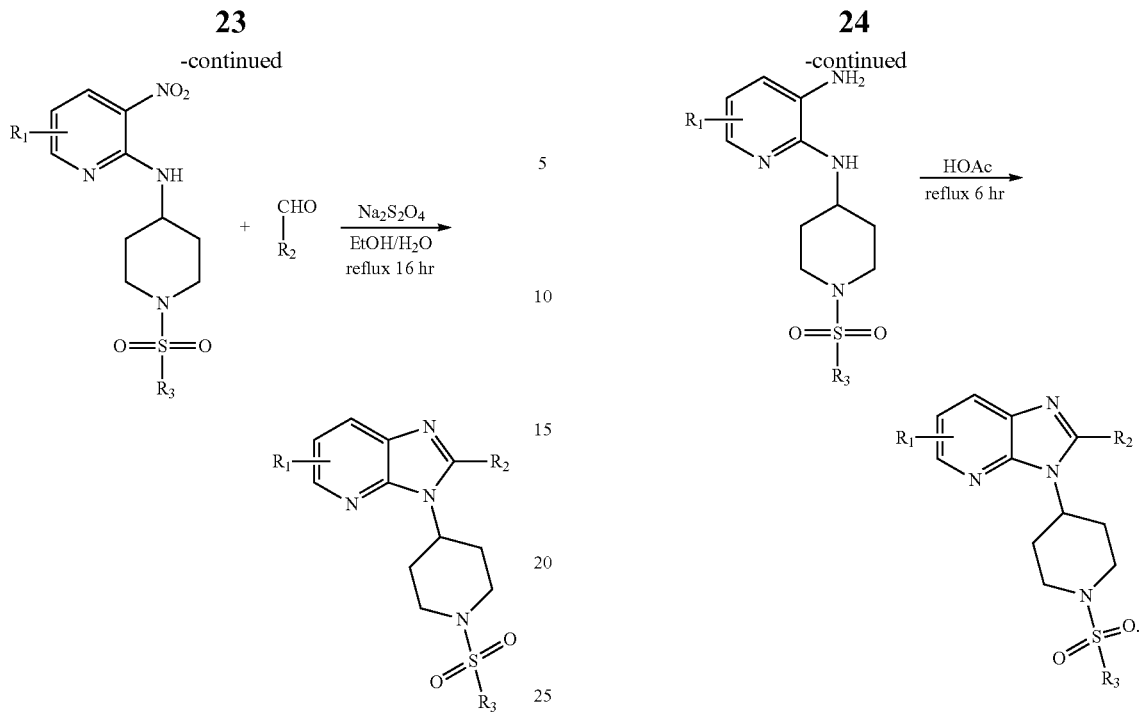

SCHEME 3:

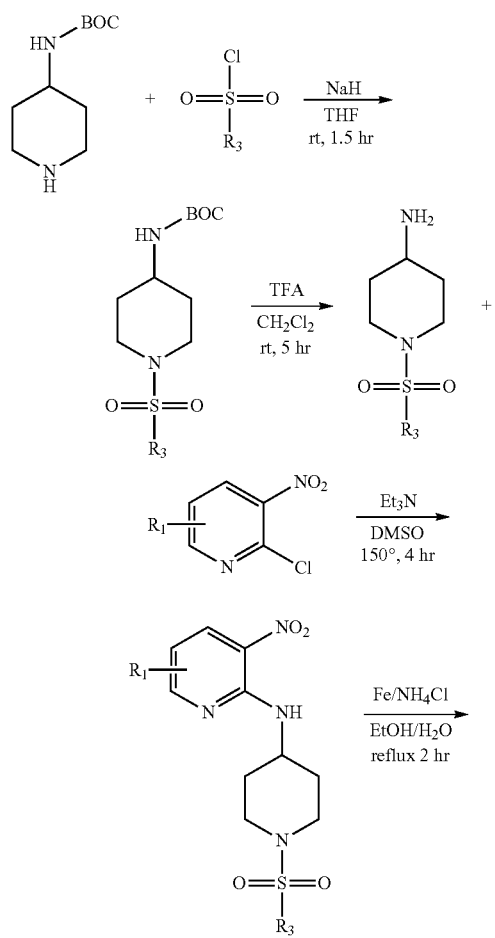

Compounds of the invention are useful as modulators of CFTR and treating diseases or disorders mediated by CFTR such as for the treatment of disease, disorders or conditions such as Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease and Straussler-Scheinker syndrome.

The compounds of the invention may be administered in combination with antibiotics, anti-inflammatory medicines, bronchodilators, or mucus-thinning medicines. In particular antibiotics for the treatment of bacteria mucoid *Pseudomonas* may be used in combination with compounds of the invention. Inhaled antibiotics such as tobramycin, colistin, and aztreonam can be used in combination with treatment with compounds of the invention. Anti-inflammatory medicines may also be used in combination with compounds of the invention to treat CFTR related diseases. Bronchodilators can be used in combination with compounds of the invention to treat CFTR related diseases.

In one embodiment, the invention relates to combination therapy comprising compounds of the invention and other pharmaceutical agents useful for the treatment of CF. In a preferred embodiment, the aminoglycoside gentamicin can be used. In a preferred embodiment, ataluren, Ivacaftor (Kalydeco) or VX-809 may be used in combination with compounds of the invention.

In one embodiment, the invention relates to pharmaceutical compositions comprising compounds of the invention and pharmaceutically acceptable carriers. The compositions may include compounds of the invention, and optionally a pharmaceutically acceptable carrier, adjuvant or vehicle. In certain embodiments, these compositions optionally further comprise one or more additional therapeutic agents useful for the treatment of CFTR mediated diseases or disorders.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha- (α), beta- (β) and gamma- (γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol.

INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to VanDevanter et al., U.S. Pat. No. 5,508,269 to Smith et al., and WO 98/43650 by Montgomery).

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio' radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "substituted" refers to the replacement of one or more hydrogen radicals in a given structure with the radical of a specified substituent including, but not limited to: deutero, halo, alkyl, cycloalkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug", and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

LIST OF ABBREVIATIONS

All temperatures are in degrees Centigrade
rt—room temperature
hr—hours
$Et_3N$—triethylamine
DMSO—dimethylsulfoxide
EtOAc—ethyl acetate
$Na_2SO_4$—sodium sulfate
$Et_2O$—diethyl ether
TFA—trifluoroacetic acid
$CH_2Cl_2$—methylene chloride
$NaHCO_3$—sodium bicarbonate
$H_2O$—water
DIPEA—diisopropylethylamine
HCl—hydrochloric acid
NaH—sodium hydride
THF—tetrahydrofuran
$NH_4Cl$—ammonium chloride
HOAc—acetic acid
n-BuLi—n-butyl lithium
$SO_2Cl_2$—sulfuryl chloride.

EXAMPLES

Example 1

3-(1-(Benzo[d][1,3]dioxol-5-ylsulfonyl)piperidin-4-yl)-2-(2-chlorophenyl)-3H-imidazo[4,5-b]pyridine (8)

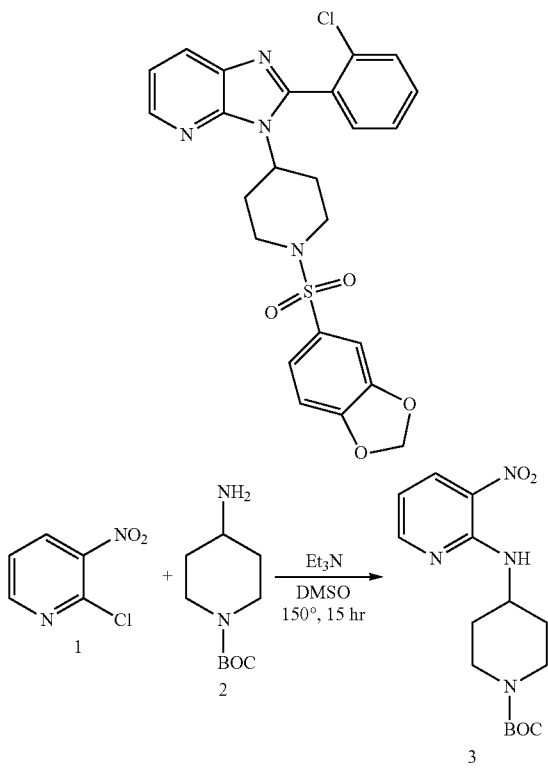

tert-Butyl 4-((3-nitropyridin-2-yl)amino)piperidin-1-carboxylate (3)

Et$_3$N (2.6 mL, 19.26 mmol) was added to a stirred solution of 1 (2.35 g, 14.822 mmol) and 2 (2.97 g, 14.822 mmol) in anhydrous DMSO (30 mL) at room temperature (rt). The resulting reaction mixture was stirred at 150° C. for 15 hr. After the reaction was complete, it was cooled to rt and ice-cold H$_2$O was added. The resulting mixture was extracted with EtOAc; 2×30 mL). The combined organic layers were dried over anhydrous Na$_2$SO$_4$ and concentrated in vacuo to give the crude compound as a thick brown liquid. This was triturated with hexanes to give 3.3 g (69% yield) of 3 as a yellow solid. LCMS m/z 267 [M−56+H], 223 [M−100+H].

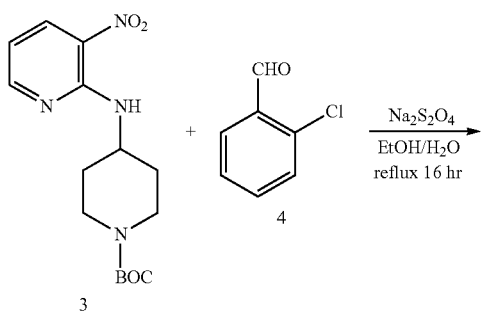

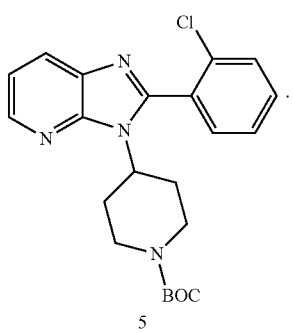

tert-Butyl 4-(2-(2-chlorophenyl)-3H-imidazo[4,5-b]pyridin-3-yl)piperidine-1-carboxylate (5)

Saturated sodium dithionite (8.91 g, 51.18 mmol) solution was added to a stirred solution of 3 (3.3 g, 10.23 mmol) and 4 (1.43 g, 10.237 mmol) in EtOH 33 mL) at rt. The reaction mixture was heated to 110° C. and stirred for 16 hr. After the reaction was complete, the reaction mixture was cooled to rt and ice-cold H$_2$O was added. The resulting mixture was extracted with EtOAc (2×75 mL). The combined organic layers were dried over anhydrous Na$_2$SO$_4$ and concentrated in vacuo to give the crude product. This was washed with Et$_2$O and n-hexane (1:10) to give 2.45 g (58% yield) of pale yellow solid 5 which was used in the next step without any further purification. LCMS m/z 413 [M+H−1], 415 [M+H+1], 313 [M+H−100−1], 315 [M+H−100+1].

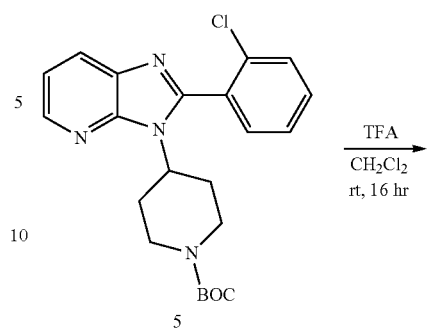

2-(2-Chlorophenyl)-3-(piperidin-4-yl)-3H-imidazo[4,5-b]pyridine (6)

TFA (7.5 mL) was added to a stirred solution of 5 (2.45 g, 5.93 mmol) in anhydrous CH$_2$Cl$_2$ (25 mL) at 0° C. The reaction mixture was allowed to warm to rt and stirred for 16 hr. The reaction mixture was basified with saturated NaHCO$_3$ solution, then extracted with CH$_2$Cl$_2$. The organic layer was washed with H$_2$O, followed by brine solution and dried over anhydrous Na$_2$SO$_4$. The organic layer concentrated in vacuo to give crude 6 as a pale yellow solid. This was triturated with Et$_2$O and n-hexanes (1:10) to give 1.5 g (81% yield) of 6 as a pale yellow solid. LCMS m/z 313 [M+H−1], 315 [M+H+1].

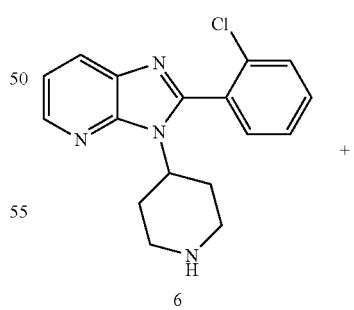

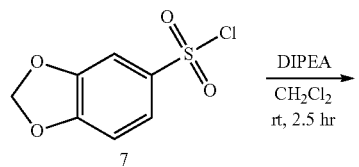

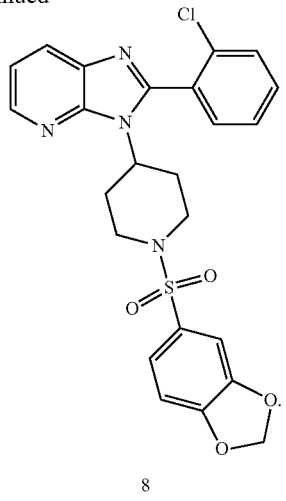

8

3-(1-(Benzo[d][1,3]dioxol-5-ylsulfonyl)piperidin-4-yl)-2-(2-chlorophenyl)-3H-imidazo[4,5-b]pyridine (8)

DIPEA (0.19 mL, 1.15 mmol) was added to a stirred solution of 6 (0.12 g, 0.383 mmol) in anhydrous CH$_2$Cl$_2$ (3 mL) at 0° C. The reaction mixture was stirred at this temperature for 2 hr and then 7 (0.084 g, 0.383 mmol) was added. The resulting mixture was allowed to warm to rt and stirred at rt for 30 min. The reaction mixture was basified using saturated NaHCO$_3$ solution then extracted with CH$_2$Cl$_2$. The organic layer was washed with H$_2$O, followed by brine solution and dried over anhydrous Na$_2$SO$_4$. The organic layer was concentrated in vacuo to give the crude product as a semi-solid. The crude product was purified by flash column chromatography using 100-200 mesh silica gel. The desired product was eluted in 50% EtOAc in pet-ether to obtain 0.075 g (39%) of pure 8 as a pale yellow solid. $^1$H NMR (DMSO-d$_6$) δ 8.42-8.41 (dd, J=4.8 Hz, J=1.6 Hz, 1H), 8.13-8.11 (dd, J=1.4 Hz, J=7.8 Hz, 1H), 7.67-7.59 (m, 3H), 7.54-7.48 (m, 1H), 7.36-7.33 (dd, J=7.8 Hz, J=5.0 Hz, 1H), 7.28-7.26 (dd, J=8.0 Hz, J=1.6 Hz, 1H), 7.21 (d, J=1.6 Hz, 1H), 7.11 (d, J=8.0 Hz, 1H), 6.18 (s, 2H), 4.00-3.90 (m, 1H), 3.80-3.66 (br m, 2H), 3.10-2.85 (br m, 2H), 2.38-2.26 (br m, 2H), 2.02-1.74 (br m, 2H). LCMS m/z 497 [M+H−1], 499 [M+H+1].

Example 2

3-(1-Benzo[d][1,3]dioxol-5-ylsulfonyl(piperidin-4-yl)-2-(2-chlorophenyl)-5-methyl-3H-imidazo[4,5-b]pyridine (13)

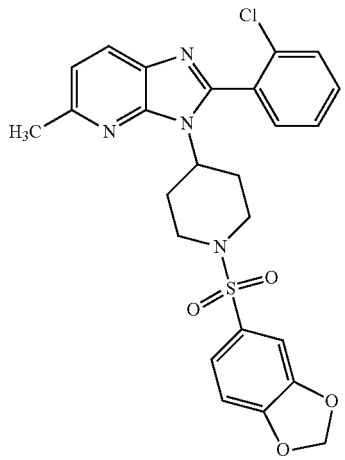

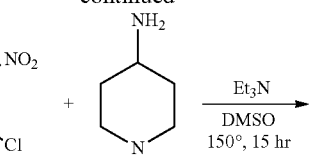

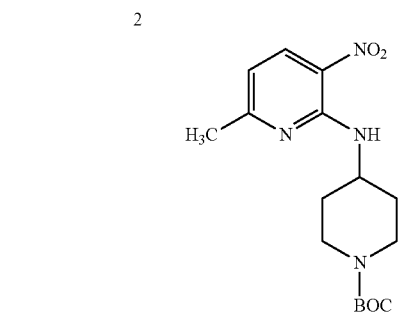

10 tert-Butyl 4-((6-methyl-3-nitropyridin-2-yl)amino)piperidine-1-carboxylate (10)

Et$_3$N (4.52 mL, 74.578 mmol) was added to a stirred solution of 9 (4.29 g, 24.859 mmol), 2 (5.0 g, 24.859 mmol) in anhydrous DMSO (45 mL) at rt. The resulting reaction mixture was stirred at 150° C. for 15 hr. After the reaction was complete, it was cooled to rt and ice-cold H$_2$O was added. The resulting mixture was extracted with EtOAc (2×50 mL). The combined organic layers were dried over anhydrous Na$_2$SO$_4$ and concentrated in vacuo in order to afford crude compound as a thick brown liquid. This was washed with n-hexane to give 4.50 g (54% yield) of 10 as a yellow solid. LCMS m/z 281 [M−56+H], 237 [M−100+H].

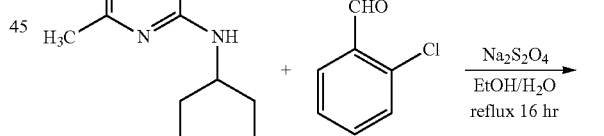

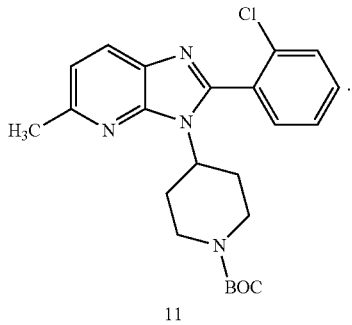

11 tert-Butyl 4-(2-(2-chlorophenyl)-5-methyl-3H-imidazo[4,5-b]pyridin-3-yl)piperidine-1-carboxylate (11)

Sodium dithionite (8.28 g, 47.563 mmol) solution was added to a stirred solution of 10 (3.2 g, 9.512 mmol) and 4 (1.33 g, 9.512 mmol) in EtOH (33 mL) at rt. The reaction mixture was stirred at 110° C. for 16 hr. After the reaction was complete, it was cooled to rt and ice-cold H₂O was added. The resulting mixture was extracted with EtOAc (2×50 mL). The combined organic layers were dried over anhydrous Na₂SO₄ and concentrated in vacuo to give crude product. This was triturated with Et₂O and n-hexane (1:10) to give 2.5 g (65% yield) of 11 as a pale yellow solid. LCMS m/z 427 [M+H−1], 429 [M+H+1], 327 [M+H−100−1], 329 [M+H−100+1].

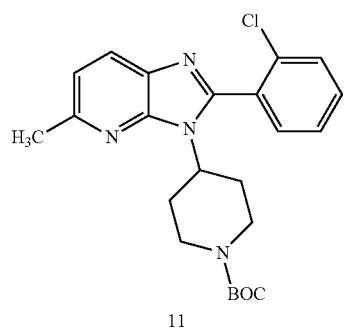

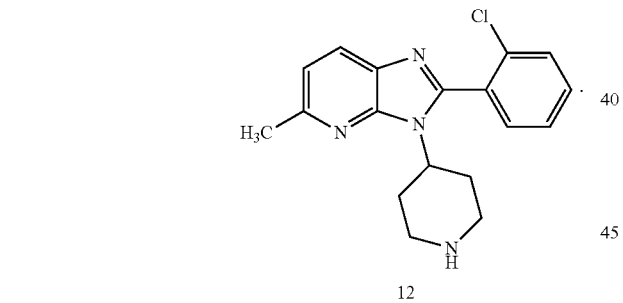

2-(2-Chlorophenyl)-5-methyl-3-(piperidin-4-yl)-3H-imidazo[4,5-b]pyridine (12)

TFA; 9 mL) was added to a stirred solution of 11 (2.5 g, 5.8556 mmol) in anhydrous CH₂Cl₂ (25 mL) at 0° C. The reaction mixture was allowed to warm to rt and stirred for 16 hr. After the reaction was complete, the reaction mixture was basified using saturated NaHCO₃ solution and extracted with CH₂Cl₂ (2×75 mL). The combined organic layers were washed with H₂O and brine solution. The organic layer was dried over anhydrous Na₂SO₄ and concentrated in vacuo to give crude 12 as a pale yellow solid. This was triturated with Et₂O and n-hexane (1:10) to give 1.5 g (78% yield) of 12 as a pale yellow solid. LCMS m/z 327 [M+H−1], 329 [M+H+1].

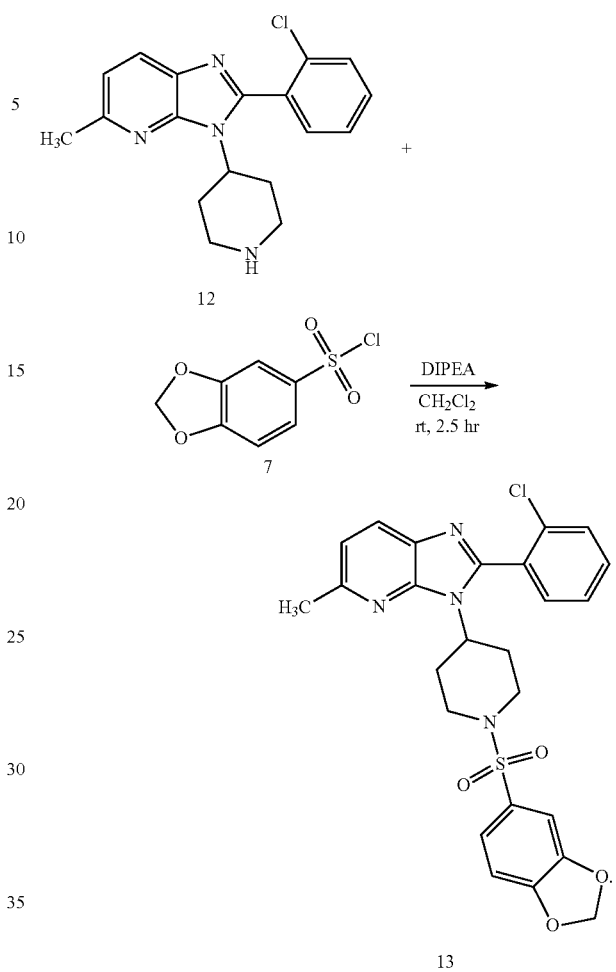

3-(1-Benzo[d][1,3]dioxol-5-ylsulfonyl(piperidin-4-yl)-2-(2-chlorophenyl)-5-methyl-3H-imidazo[4,5-b]pyridine (13)

DIPEA 0.19 mL, 1.1013 mmol) was added to a stirred solution of 12 (0.12 g, 0.3671 mmol) in anhydrous CH₂Cl₂ (3 mL) at 0° C. The reaction mixture was stirred at this temperature for 2 hr. and then 7 (0.081 g, 0.3671 mmol) was added. The resulting mixture was allowed to warm to rt and stirred at rt for 30 min. The reaction mixture was basified using saturated NaHCO₃ solution then extracted with CH₂Cl₂. The organic layer was washed with H₂O, followed by brine solution and dried over anhydrous Na₂SO₄. The organic layer was concentrated in vacuo to give crude product as a semi-solid. The crude product was purified by flash column chromatography using 100-200 mesh silica gel. The desired product was eluted in 50% EtOAc in pet-ether to obtain 0.057 g (30%) of pure 13 as a pale yellow solid. $^1$H NMR (DMSO-$d_6$) δ 7.98 (d, J=8.4 Hz, 1H), 7.66-7.61 (m, 2H), 7.59 (d, J=7.2 Hz, 1H), 7.52-7.48 (m, 1H), 7.27-7.25 (dd, J=8.2 Hz, J=1.8 Hz, 1H), 7.21 (d, J=6.4 Hz, 1H), 7.20 (d, J=2.8 Hz, 1H), 7.10 (d, J=7.6 Hz, 1H), 6.17 (s, 2H), 3.94-3.66 (br m, 1H), 3.60-3.34 (br m, 2H), 3.20-2.85 (br m, 2H), 2.63 (s, 3H), 2.66-2.40 (br m, 2H), 2.04-1.48 (br m, 2H). LCMS m/z 511 [M+H−1], 513 [M+H+1].

Example 3

3-(1-((3-Chloro-4-methoxyphenyl)sulfonyl)piperidin-4-yl)-5-methyl-2-phenyl-3H-imidazo[4,5-b]pyridine (18)

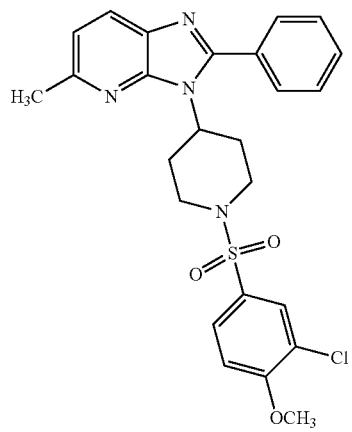

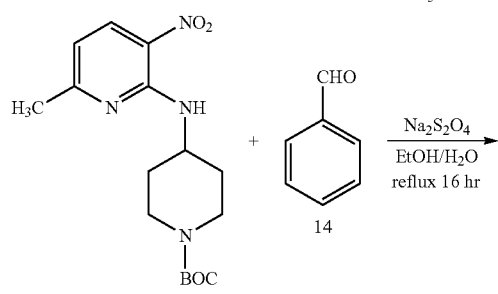

tert-Butyl 4-(5-methyl-2-phenyl-3H-imidazo[4,5-b]pyridin-3-yl)piperidine-1-carboxylate (15)

Sodium dithionite (0.646 g, 3.715 mmol) solution was added to a stirred solution of 10 (0.250 g, 0.743 mmol) and 14 (0.780 g, 0.743 mmol) in EtOH (9 mL) at rt. The reaction mixture was stirred at 110° C. for 16 hr. After the reaction was complete, it was cooled to rt and ice-cold H₂O was added. The resulting mixture was extracted with EtOAc (3×50 mL). The combined organic layers were dried over anhydrous Na₂SO₄ and concentrated in vacuo to give 0.350 g of crude 15. This was used in the next step without any further purification. LCMS m/z 393 [M+H], 293 [M−100+H].

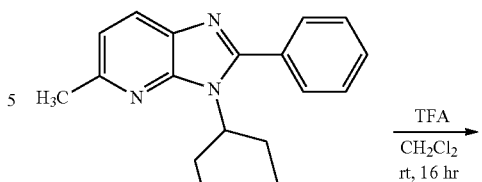

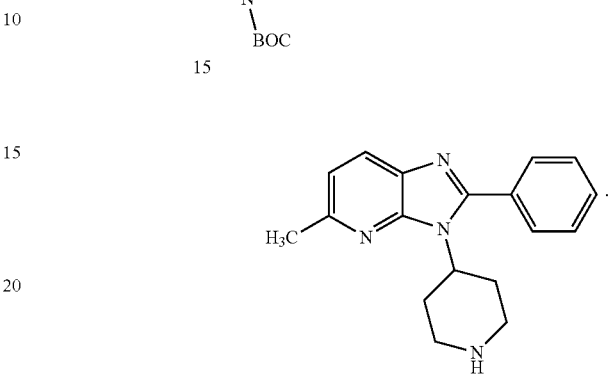

5-Methyl-2-phenyl-3-(piperidin-4-yl)-3H-imidazo[4,5-b]pyridine (16)

TFA (1.5 mL) was added to a stirred solution of 15 (0.35 g, 0.892 mmol) in anhydrous CH₂Cl₂ (10 mL) at 0° C. The reaction mixture was allowed to warm to rt and stirred for 16 hr. The reaction mixture was basified with saturated NaHCO₃ solution, then extracted with CH₂Cl₂ (3×20 mL). The combined organic layers were dried over anhydrous Na₂SO₄ and concentrated in vacuo to give 0.25 g (96% yield) of crude 16 as a pale yellow solid. LCMS m/z 293 [M+H].

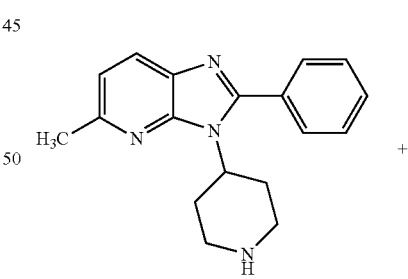

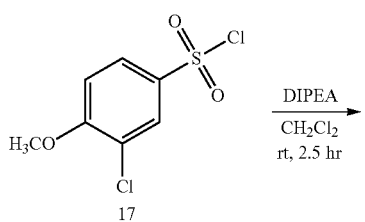

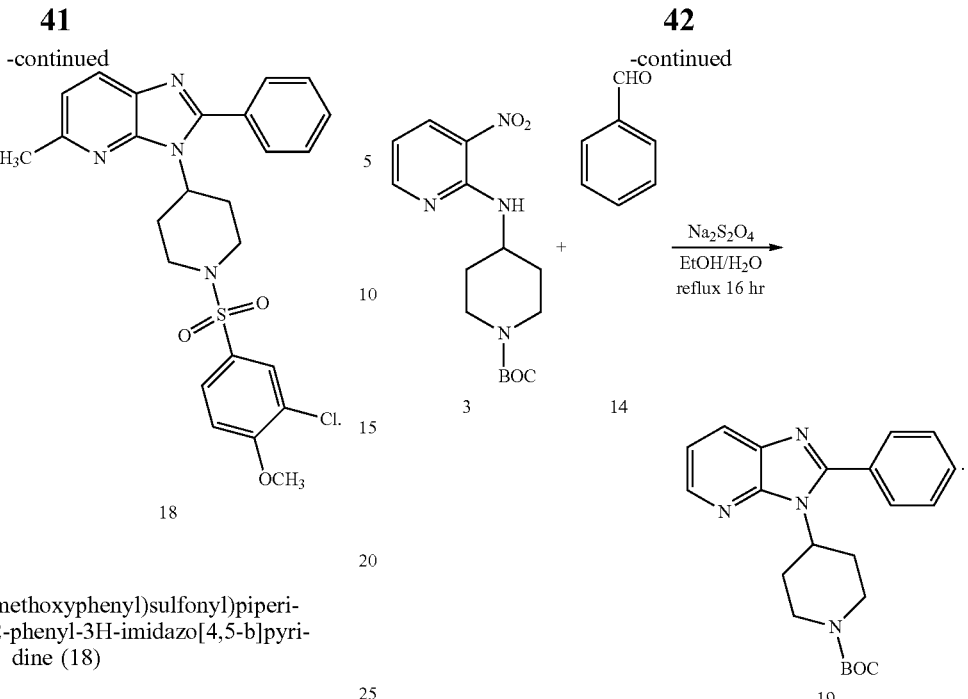

3-(1-((3-Chloro-4-methoxyphenyl)sulfonyl)piperidin-4-yl)-5-methyl-2-phenyl-3H-imidazo[4,5-b]pyridine (18)

DIPEA (0.34 mL, 2.667 mmol) was added to a stirred solution of 16 (0.20 g, 0.684 mmol) in anhydrous CH$_2$Cl$_2$ (5 mL) at 0° C. The reaction mixture was stirred at this temperature for 2 hr and then 17 (0.21 g, 0.889 mmol) was added. The resulting mixture was allowed to warm to rt and stirred at rt for 30 min. After the reaction was complete ice-cold H$_2$O was added and the resulting mixture was extracted with CH$_2$Cl$_2$. The organic layer was washed with saturated NaHCO$_3$ solution followed by brine solution and dried over anhydrous Na$_2$SO$_4$, then concentrated in vacuo to give crude 18. The crude product was purified by flash column chromatography using 100-200 mesh silica gel The desired product was eluted in 50% EtOAc in pet-ether to obtain 0.007 g (21%) of pure 18 as a pale yellow solid. $^1$H NMR (DMSO-d$_6$) δ 7.95 (d, J=10.8 Hz, 1H), 7.75 (d, J=3.2 Hz, 1H), 7.73-7.69 (dd, J=11.6 Hz, J=2.8 Hz, 1H), 7.66-7.62 (m, 2H), 7.56-7.51 (m, 3H), 7.37 (d, J=11.6 Hz, 1H), 7.17 (d, J=10.8 Hz, 1H), 4.34-4.23 (m, 1H), 3.96 (s, 3H), 3.84-3.75 (m, 2H), 3.02-2.90 (m, 2H), 2.61 (s, 3H), 2.48-2.33 (m, 2H), 1.98-1.89 (m, 2H). LCMS m/z 497 [M+H−1], 499 [M+H+1].

Example 4

3-(1-((4-Ethylphenyl)sulfonyl)piperidin-4-yl)-2-phenyl-3H-imidazo[4,5b]pyridine (22)

tert-Butyl 4-(2-phenyl-3H-imidazo[4,5-b]pyridin-3-yl)piperidine-1-carboxylate (19)

Sodium dithionite (22.14 g, 127.18 mmol) solution in H$_2$O (100 mL) was added to a stirred solution of 3 (8.2 g, 25.43 mmol) and benzaldehyde (14) (2.7 mL, 25.43 mmol) in EtOH (300 mL) at rt. The reaction mixture was refluxed for 16 hr. After the reaction was complete, the reaction mixture was cooled to rt and ice-cold H$_2$O was added. The resulting mixture was extracted with EtOAc (3×50 mL). The combined organic layers were dried over anhydrous Na$_2$SO$_4$ and concentrated in vacuo to give 4.2 g (44% yield) of brown liquid 19 which was used in the next step without any further purification. LCMS m/z 379 [M+H], 279 [M−100+H].

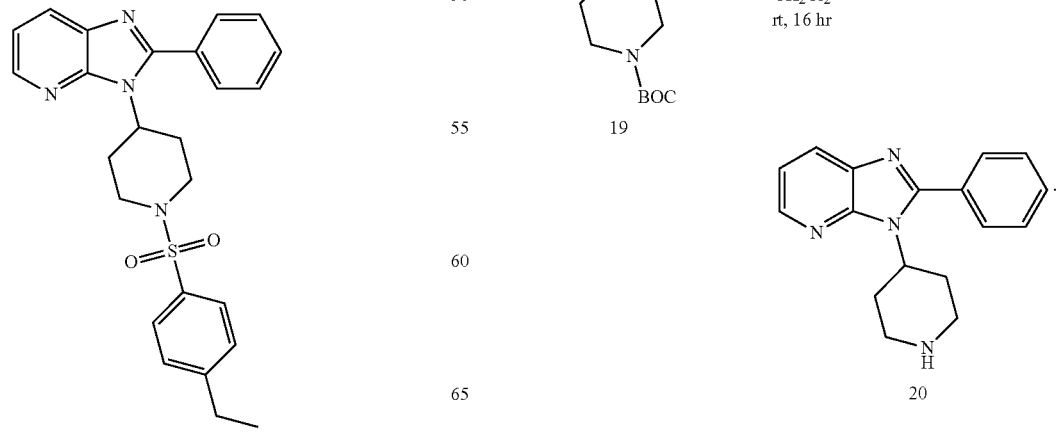

2-Phenyl-3-(piperidin-4-yl)-3H-imidazo[4,5-b]pyridine (20)

TFA (10 mL) was added to a stirred solution of 19 (4.2 g, 11.09 mmol) in anhydrous $CH_2Cl_2$ (45 mL) at 0° C. The reaction mixture was allowed to warm to rt and stirred for 16 hr. The reaction mixture was basified with saturated $NaHCO_3$ solution, then extracted with $CH_2Cl_2$ (3×20 mL). The combined organic layer were dried over anhydrous $Na_2SO_4$ and concentrated in vacuo to give 2.5 g (81% yield) of crude 20 as a yellow solid which was used in the next step without any further purification. LCMS m/z 279 [M+H].

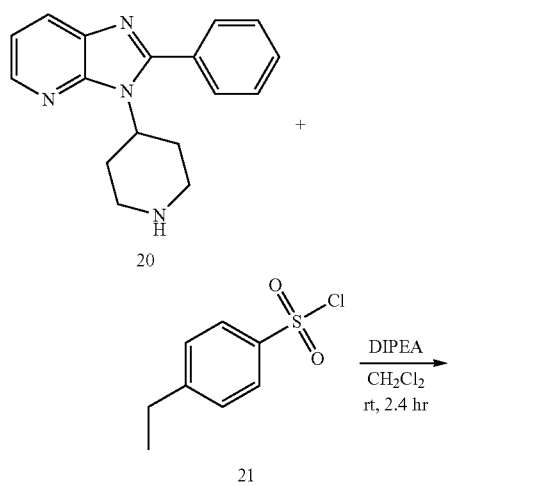

3-(1-((4-Ethylphenyl)sulfonyl)piperidin-4-yl)-2-phenyl-3H-imidazo[4,5-b]pyridine (22)

DIPEA (0.44 mL, 2.67 mmol) was added to a stirred solution of 20 (0.250 g, 0.89 mmol) in anhydrous $CH_2Cl_2$ (2.5 mL) at 0° C. The reaction mixture was warmed to rt and stirred at rt for 2.5 hr, then cooled again to 0° C. 21 (0.18 mL, 1.16 mmol) was added and the resulting mixture was allowed to warm to rt and stirred at rt for 30 min. The reaction mixture was basified using saturated $NaHCO_3$ solution then extracted with $CH_2Cl_2$. The organic layer was dried over anhydrous $Na_2SO_4$ then concentrated in vacuo to give the crude product. The crude product was purified by flash column chromatography using 100-200 mesh silica gel The desired product was eluted in 50% EtOAc in pet-ether to obtain 0.170 g (42%) of pure 22 as a pale yellow solid. $^1$H NMR (DMSO-$d_6$) δ 8.39-8.37 (dd, J=6.4 Hz, J=2.0 Hz, 1H), 8.11-8.07 (dd, J=10.8 Hz, J=2.0 Hz, 1H), 7.70-7.61 (m, 4H), 7.57-7.52 (m, 3H), 7.48 (d, J=11.2 Hz, 2H), 7.35-7.30 (dd, J=10.8 Hz, J=6.4 Hz, 1H), 4.41-4.28 (m, 1H), 3.84-3.74 (m, 2H), 3.08-2.90 (m, 2H), 2.76-2.67 (q, J=10.0 Hz, 2H), 2.42-2.29 (m, 2H), 2.01-1.90 (m, 2H), 1.21 (t, J=10.0 Hz, 3H). LCMS m/z 447 [M+H].

Example 5

3-(1-(Benzo[d][1,3]dioxol-5-ylsulfonyl)piperidin-4-yl)-2-phenyl-3H-imidazo[4,5-b]pyridine (23)

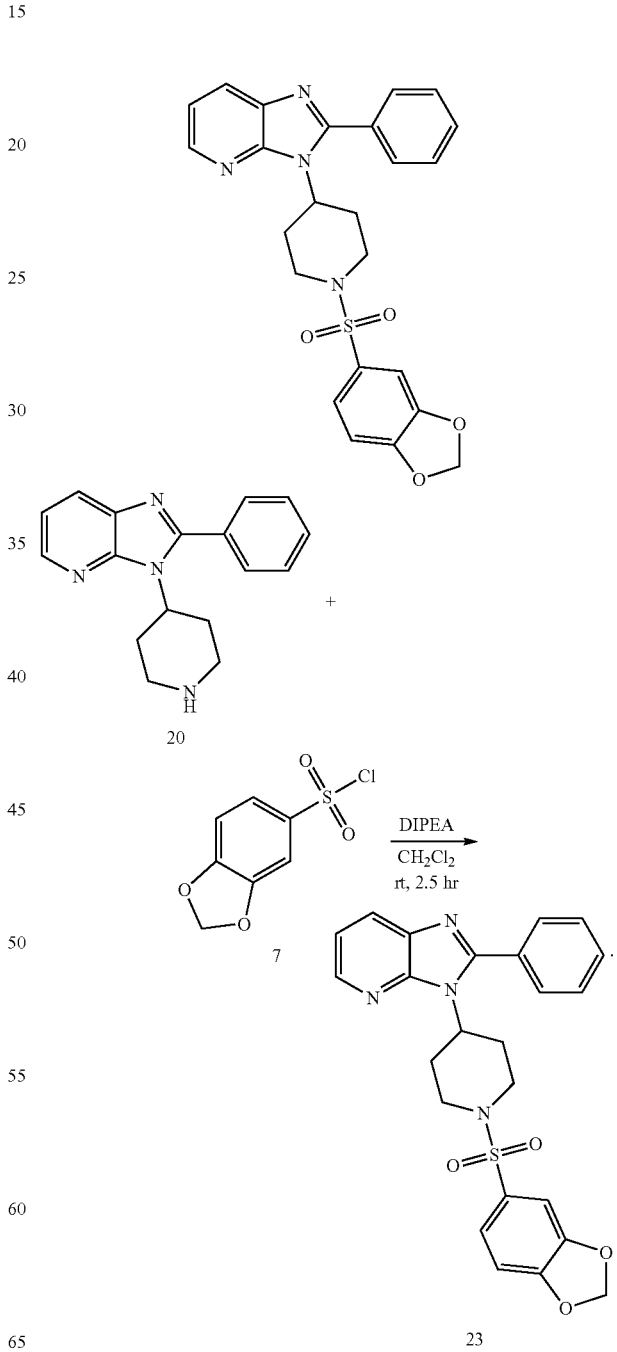

3-(1-(Benzo[d][1,3]dioxol-5-ylsulfonyl)piperidin-4-yl)-2-phenyl-3H-imidazo[4,5-b]pyridine (23)

DIPEA (0.26 mL, 1.61 mmol) was added to a stirred solution of 20 (0.150 g, 0.53 mmol) in anhydrous CH$_2$Cl$_2$ (3.0 mL) at 0° C. The reaction mixture was warmed to rt and stirred at rt for 2.5 hr, then cooled again to 0° C. 7 (0.1545 g, 0.7 mmol) was added and the resulting mixture was allowed to warm to rt and stirred at rt for 30 min. The reaction mixture was basified using saturated NaHCO$_3$ solution then extracted with CH$_2$Cl$_2$. The organic layer was dried over anhydrous Na$_2$SO$_4$ then concentrated in vacuo to give the crude product. The crude product was purified by flash column chromatography using 100-200 mesh silica gel The desired product was eluted in 50% EtOAc in pet-ether to obtain 0.75 g (30%) of pure 23 as an off-white solid. $^1$H NMR (DMSO-d$_6$) δ 8.37-8.35 (dd, J=6.6 Hz, J=1.8 Hz, 1H), 8.09-8.06 (dd, J=10.8 Hz, J=1.2 Hz, 1H), 7.66 (d, J=3.2 Hz, 1H), 7.64 (d, J=4.8 Hz, 1H), 7.55 (d, J=3.2 Hz, 2H), 7.53 (d, J=1.6 Hz, 1H), 7.33-7.29 (dd, J=10.8 Hz, J=6.0 Hz, 1H), 7.30-7.26 (dd, J=10.8 Hz, J=2.0 Hz, 1H), 7.22 (d, J=2.0 Hz, 1H), 7.12 (d, J=10.8 Hz, 1H), 6.17 (s, 2H), 4.39-4.27 (m, 1H), 3.81-3.71 (m, 2H), 3.05-2.88 (m, 2H), 2.46-2.31 (m, 2H), 1.98-1.87 (m, 2H). LCMS m/z 463 [M+H].

Example 6

3-(1-((3-Chloro-4-methoxyphenyl)sulfonyl)piperidin-4-yl)-2-(2-chlorophenyl)-3H-imidazo[4,5-b]pyridine (26)

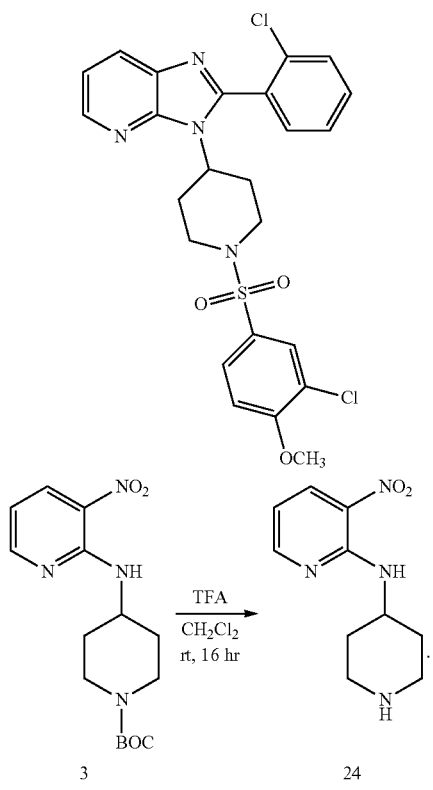

3-Nitro-N-(piperidin-4-yl)pyridin-2-amine (24)

TFA (12.5 mL) was added to a stirred solution of 3 (2.5 g, 7.75 mmol) in anhydrous CH$_2$Cl$_2$ (20 mL) at 0° C. The reaction mixture was allowed to warm to rt and stirred for 16 hr. The reaction mixture was evaporated in vacuo, basified with saturated NaHCO$_3$ solution, then extracted with EtOAc (3×20 mL). The combined organic layers were dried over anhydrous Na$_2$SO$_4$ and concentrated in vacuo to give crude 24 as a yellow solid which was used in the next step without any further purification. LCMS m/z 223 [M+H].

N-(1-((3-Chloro-4-methoxyphenyl)sulfonyl)piperidin-4-yl)-3-nitropyridin-2-amine (25)

To a stirred solution of 24 (1.0 g, 4.499 mmol) in pyridine (12 mL) at 0° C. was added 17 (1.46 g, 5.848 mmol). The resulting mixture was allowed to warm to rt and stirred at rt for 3 hr. After the reaction was complete the reaction mixture was poured into 1N HCl solution and the resulting mixture was extracted with EtOAc. The organic layer was collected, dried over anhydrous Na$_2$SO$_4$ and concentrated in vacuo to give the crude product 25 as a yellow solid which was used in the next step without any further purification. LCMS m/z 427 [M+H−1], 429 [M+H+1].

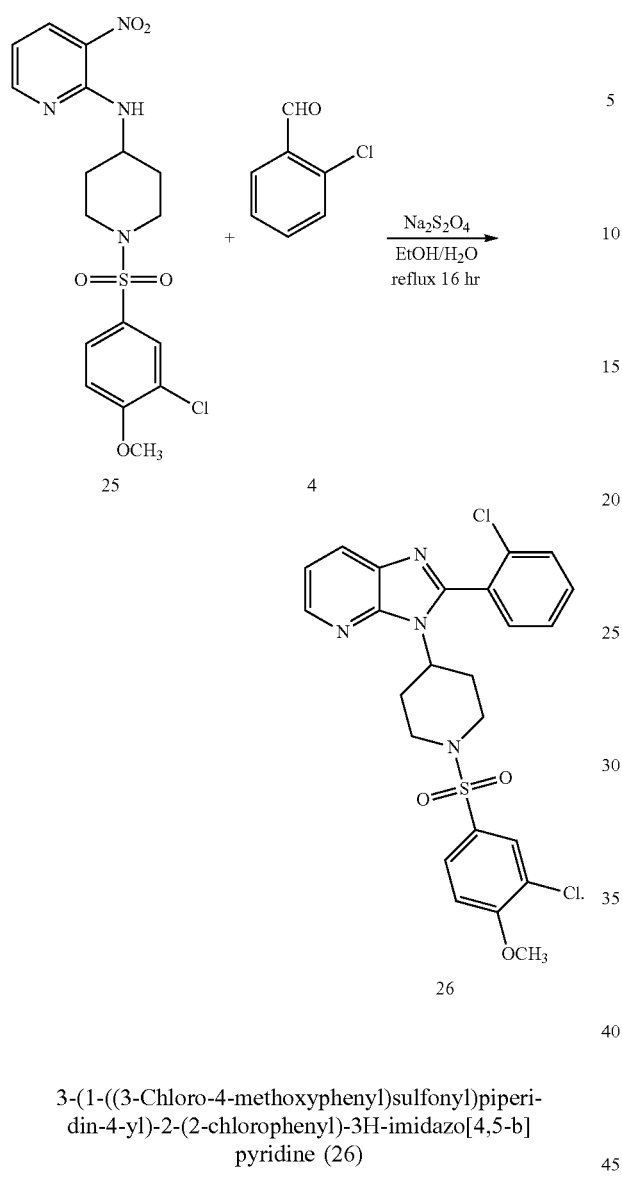

25

4

3-(1-((3-Chloro-4-methoxyphenyl)sulfonyl)piperidin-4-yl)-2-(2-chlorophenyl)-3H-imidazo[4,5-b]pyridine (26)

Saturated sodium dithionite (407.8 mg, 2.342 mmol) solution was added to a stirred solution of 25 (200 mg, 0.468 mmol) and 4 (65.8 g, 0.468 mmol) in EtOH (10 mL) at rt. The reaction mixture was heated to 110° C. and stirred for 16 hr. After the reaction was complete, the reaction mixture was cooled to rt and ice-cold H$_2$O was added. The resulting mixture was extracted with EtOAc (3×50 mL). The combined organic layers were dried over anhydrous Na$_2$SO$_4$ and concentrated in vacuo to give the crude product. This was purified by flash column chromatography using 100-200 mesh silica gel. The desired product was eluted in 40% EtOAc in pet-ether to give 0.060 g (27% yield) of off-white solid 26. $^1$H NMR (DMSO-d$_6$) δ 8.39-8.38 (dd, J=4.4 Hz, J=0.8 Hz, 1H), 8.13-8.10 (dd, J=7.8 Hz, J=1.2 Hz, 1H), 7.74 (d, J=2.0 Hz, 1H), 7.72-7.68 (m, 1H), 7.67-7.64 (m, 1H), 7.63-7.58 (m, 2H), 7.53-7.48 (m, 1H), 7.36 (d, J=8.4 Hz, 1H), 7.35 (d, J=7.6 Hz, 1H), 3.96 (s, 3H), 4.01-3.91 (br m, 1H), 3.84-3.70 (br m, 2H), 3.08-2.93 (br m, 2H), 2.44-2.36 (br m, 2H), 2.00-1.74 (br m, 2H). LCMS m/z 517 [M+H−1], 519 [M+H+1], 521 [M+H+3].

Example 7

3-(1-((3-Chloro-4-methylphenyl)sulfonyl)piperidin-4-yl)-2-(2-chlorophenyl)-5-methyl-3H-imidazo[4,5-b]pyridine (28)

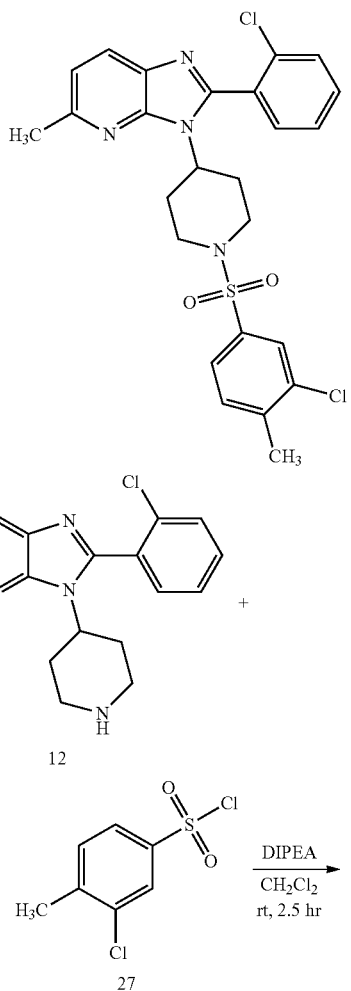

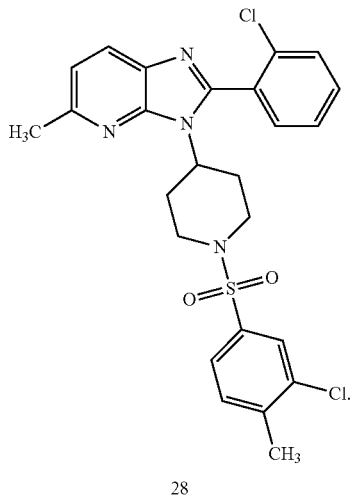

3-(1-((3-Chloro-4-methylphenyl)sulfonyl)piperidin-4-yl)-2-(2-chlorophenyl)-5-methyl-3H-imidazo[4,5-b]pyridine (28)

DIPEA (0.19 mL, 1.101 mmol) was added to a stirred solution of 12 (0.12 g, 0.367 mmol) in anhydrous $CH_2Cl_2$ (3 mL) at 0° C. The reaction mixture was stirred at this temperature for 2 hr and then 27 (0.082 g, 0.367 mmol) was added. The resulting mixture was allowed to warm to rt and stirred at rt for 30 min. After the reaction was complete, ice-cold $H_2O$ was added and the resulting mixture was extracted with $CH_2Cl_2$. The organic extract was washed with saturated $NaHCO_3$, followed by brine solution and dried over anhydrous $Na_2SO_4$, then concentrated in vacuo to give the crude product as a semi-solid. The crude product was purified by flash column chromatography using 100-200 mesh silica gel. The desired product was eluted in 40% EtOAc in pet-ether to obtain 0.041 g (22%) of pure 28 as a pale yellow solid. $^1$H NMR (DMSO-$d_6$) δ 7.98-7.96 (d, J=8 Hz, 1H), 7.70 (s, 1H), 7.64-7.57 (m, 5H), 7.51-7.47 (t, J=7.2 Hz, 1H), 7.21-7.19 (d, J=8.4 Hz, 1H), 3.92-3.89 (d, J=12 Hz 1H), 3.76 (br s, 2H), 3.00 (br s, 2H), 2.62 (br s, 3H), 2.41 (br s, 3H), 2.33-2.28 (br d, J=19.6 Hz, 2H), 1.95-1.84 (br d, J=45.8 Hz, 2H). LCMS m/z 515 [M+H−1], 517 [M+H+1], 519 [M+H+3].

Example 8

2-(2-Chlorophenyl)-3-(1-((3-fluoro-4-methyoxyphenyl)sulfonyl)piperidin-4-yl)-5-methyl-3H-imidazo[4,5-b]pyridine (30)

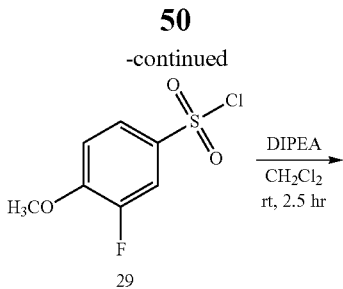

2-(2-Chlorophenyl)-3-(1-((3-fluoro-4-methyoxyphenyl)sulfonyl)piperidin-4-yl)-5-methyl-3H-imidazo[4,5-b]pyridine (30)

DIPEA (0.19 mL, 1.101 mmol) was added to a stirred solution of 12 (0.12 g, 0.367 mmol) in anhydrous $CH_2Cl_2$ (3 mL) at 0° C. The reaction mixture was stirred at this temperature for 2 hr and then 29 (0.082 g, 0.367 mmol) was added. The resulting mixture was allowed to warm to rt and stirred at rt for 30 min. After the reaction was complete, ice-cold $H_2O$ was added and the resulting mixture was extracted with $CH_2Cl_2$. The organic extract was washed with saturated $NaHCO_3$, followed by brine solution and dried over anhydrous $Na_2SO_4$, then concentrated in vacuo to give the crude product as a semi-solid. The crude product was purified by flash column chromatography using 100-200 mesh silica gel. The desired product was eluted in 40% EtOAc in pet-ether to obtain 0.040 g (21%) of pure 30 as a pale yellow solid. $^1$H NMR (DMSO-$d_6$) δ 7.98-7.96 (d, J=8.4 Hz, 1H), 7.65-7.47 (m, 6H), 7.40-7.36 (t, J=8.4 Hz, 1H), 7.21-7.19 (d, J=8 Hz, 1H), 3.93-3.86 (m, 4H), 3.74 (br s, 2H), 3.00 (br s, 2H), 2.62 (s, 3H), 2.33-2.32 (t, J=1.6 Hz, 2H), 1.94-1.82 (br d, J=48.8 Hz, 2H). LCMS m/z 515 [M+H−1], 517 [M+H+1].

Example 9

2-(3-(1-((3-Chloro-4-methoxyphenyl)sulfonyl)piperidin-4-yl)-3H-imidazo[4,5-b]pyridin-2-yl)phenol (32)

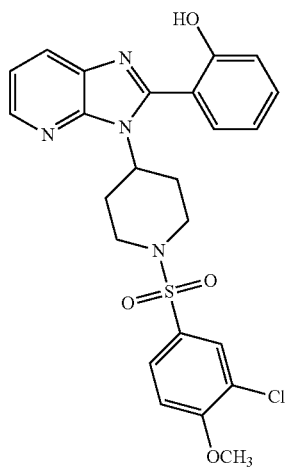

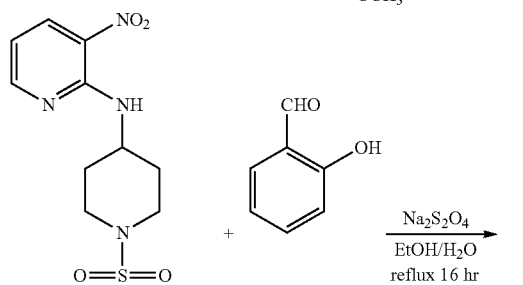

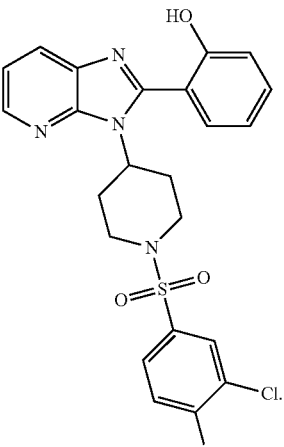

2-(3-(1-((3-Chloro-4-methoxyphenyl)sulfonyl)piperidin-4-yl)-3H-imidazo[4,5-b]pyridin-2-yl)phenol (32)

Saturated sodium dithionite (203 mg, 1.171 mmol) solution was added to a stirred solution of 25 (100 mg, 0.234 mmol) and 31 (0.023 mL, 0.234 mmol) in EtOH (10 mL) at rt. The reaction mixture was heated to 110° C. and stirred for 16 hr. After the reaction was complete, the reaction mixture was cooled to rt and ice-cold $H_2O$ was added. The resulting mixture was extracted with EtOAc (3×50 mL). The combined organic layers were dried over anhydrous $Na_2SO_4$ and concentrated in vacuo to give the crude product. This was purified by flash column chromatography using 100-200 mesh silica gel The desired product was eluted in 40% EtOAc in pet-ether to give 0.023 g (20% yield) of off-white solid 32. $^1$H NMR (DMSO-$d_6$) δ 10.15 (br s, 1H), 8.32-8.31 (d, J=4.8 Hz, 1H), 8.06-8.03 (d, J=6.6 Hz, 1H), 7.76-7.76 (d, J=1.8 Hz, 1H), 7.73-7.72 (d, J=2.25 Hz, 1H), 7.38-7.27 (m, 4H), 6.98-6.91 (dd, J=7.2 Hz, 2H), 4.08-4.04 (m, 1H), 3.970 (s, 3H), 3.84-3.80 (d, J=12.3 Hz, 2H), 2.95-2.84 (m, 2H), 2.39-2.27 (q, J=11.85 Hz, 2H) 1.89-1.86 (d, J=10.2 Hz, 2H). LCMS m/z 499 [M+H−1], 501 [M+H+1].

Example 10

3-(1-((3-Chloro-4-methylphenyl)sulfonyl)piperidin-4-yl)-2-(2-chlorophenyl)-3H-imidazo[4,5-b]pyridine (33)

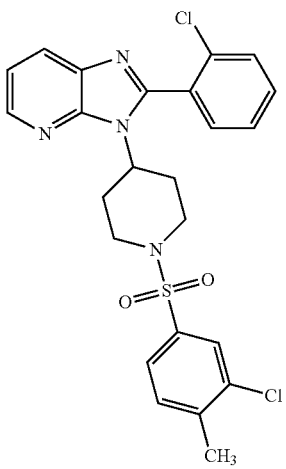

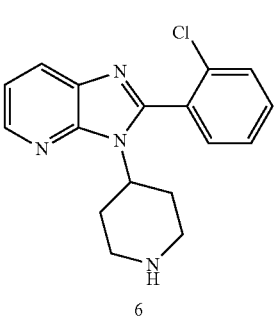

Example 11

3-(1-((3-Chloro-4-methoxyphenyl)sulfonyl)piperidin-4-yl)-2-(2-fluorophenyl)-3H-imidazo[4,5-b]pyridine (37)

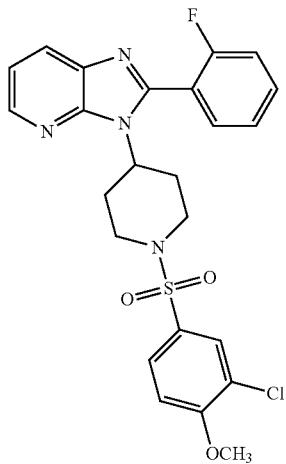

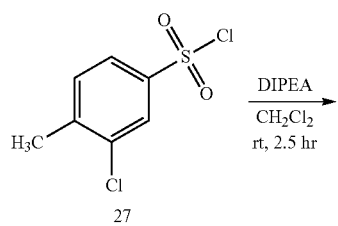

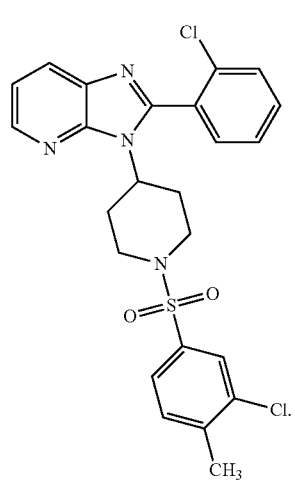

3-(1-((3-Chloro-4-methylphenyl)sulfonyl)piperidin-4-yl)-2-(2-chlorophenyl)-3H-imidazo[4,5-b]pyridine (33)

DIPEA (0.2 mL, 1.150 mmol) was added to a stirred solution of 6 (0.12 g, 0.383 mmol) in anhydrous CH$_2$Cl$_2$ (3 mL) at 0° C. The reaction mixture was stirred at this temperature for 2 hr and then 27 (0.18 mL, 0.498 mmol) was added. The resulting mixture was allowed to warm to rt and stirred at rt for 30 min. The reaction mixture was washed with saturated NaHCO$_3$, H$_2$O was added, and the resulting mixture was extracted with CH$_2$Cl$_2$. The organic layer was dried over anhydrous Na$_2$SO$_4$, then concentrated in vacuo to give the crude product. This was purified by flash column chromatography using 100-200 mesh silica gel. The desired product was eluted in 50% EtOAc in pet-ether to obtain 0.93 g (48%) of pure 33 as an off-white solid. $^1$H NMR (DMSO-d$_6$) δ 8.41-8.39 (dd, J=4.8 Hz, 1H), 8.13-8.10 (dd, J=8.1 Hz, 1H), 7.71 (s, 1H), 7.67-7.58 (m, 5H), 7.53-7.50 (dd, J=6.75 Hz, 1H), 7.38-7.32 (dd, J=4.8 Hz, 1H), 4.02-3.94 (t, J=12 Hz, 1H), 3.80-3.77 (d, J=8.1 Hz, 2H), 3.0 (bs, 2H), 2.425 (br s, 5H), 2.16 (br s, 2H). LCMS m/z 501 [M+H−1], 503 [M+H+1] 505 [M+H+3].

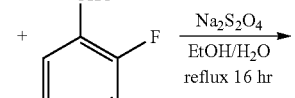

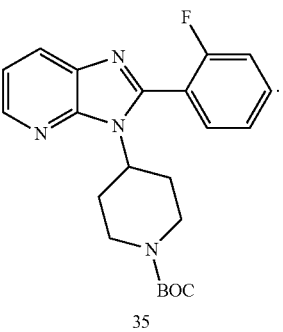

tert-Butyl 4-(2-(2-fluorophenyl)-3H-imidazo[4,5-b]pyridin-3-yl)piperidine-1-carboxylate (35)

Saturated sodium dithionite (1.0 g, 6.20 mmol) solution was added to a stirred solution of 3 (0.4 g, 1.240 mmol) and 34 (0.154 g, 1.240 mmol) in EtOH (10 mL) and H$_2$O (2 mL) at rt. The reaction mixture was heated to 110° C. and stirred for 16 hr. After the reaction was complete, the reaction mixture was cooled to rt and ice-cold H$_2$O was added. The resulting mixture was extracted with EtOAc (2×75 mL). The combined organic layers were dried over anhydrous Na$_2$SO$_4$ and concentrated in vacuo to give the crude product. This was washed with Et$_2$O and n-hexane (1:10) to give 0.2 g (41% yield) of pale yellow solid 35 which was used in the next step without any further purification. LCMS m/z 397 [M+H].

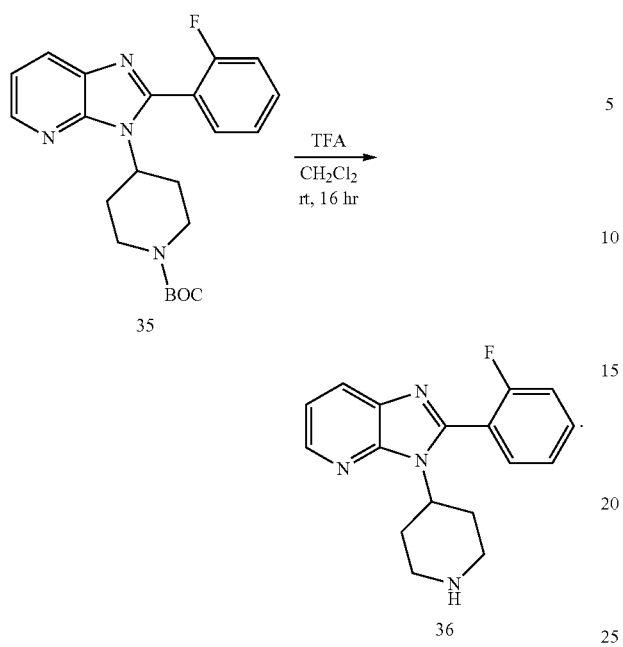

35

2-(2-Fluorophenyl)-3-(piperidin-4-yl)-3H-imidazo[4,5-b]pyridine (36)

TFA (0.6 mL) was added to a stirred solution of 35 (0.2 g, 0.5044 mmol) in anhydrous CH$_2$C$_2$ (2 mL) at 0° C. The reaction mixture was allowed to warm to rt and stirred for 16 hr. The reaction mixture was basified with saturated NaHCO$_3$ solution then extracted with CH$_2$Cl$_2$. The organic layer was washed with H$_2$O, followed by brine solution and dried over anhydrous Na$_2$SO$_4$. The organic layer concentrated in vacuo to give 0.1 g (67% yield) of crude 36 as a pale yellow solid which was used in the next step without any further purification. LCMS m/z 297 [M+H].

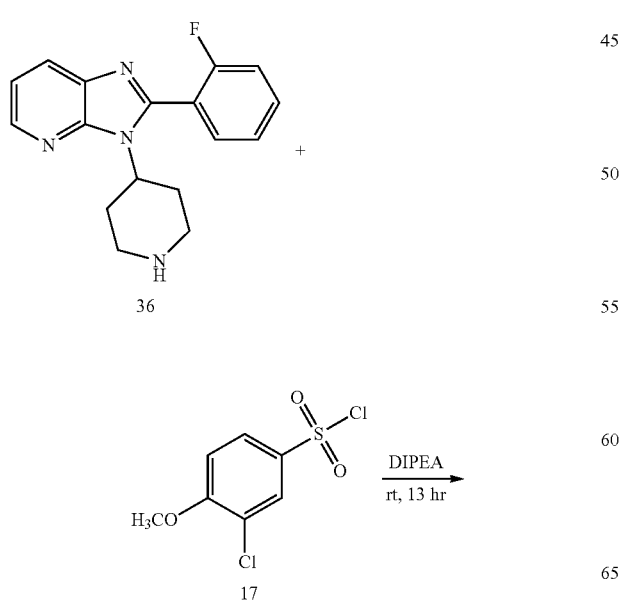

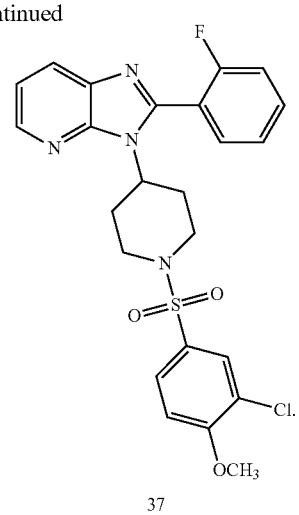

37

3-(1-((3-Chloro-4-methoxyphenyl)sulfonyl)piperidin-4-yl)-2-(2-fluorophenyl)-3H-imidazo[4,5-b]pyridine (37)

DIPEA (0.17 mL, 1.012 mmol) was added to a stirred solution of 36 (0.1 g, 0.337 mmol) in anhydrous CH$_2$Cl$_2$ (3 mL) at 0° C. The reaction mixture was stirred at this temperature for 2 hr and then 17 (0.1 mL, 0.438 mmol) was added. The resulting mixture was allowed to warm to rt and stirred at rt for 30 min. The reaction mixture was washed with saturated NaHCO$_3$, H$_2$O was added, and the resulting mixture was extracted with CH$_2$Cl$_2$. The organic layer was dried over anhydrous Na$_2$SO$_4$, then concentrated in vacuo to give the crude product. This was purified by flash column chromatography using 100-200 mesh silica gel. The desired product was eluted in 50% EtOAc in pet-ether to obtain 0.12 g (7%) of pure 37 as a pale yellow solid. $^1$H NMR (DMSO-d$_6$) 8.39-8.38 (d, J=3.9 Hz, 1H), 8.13-8.11 (d, J=6.9 Hz, 1H), 7.75-7.61 (m, 4H), 7.44-7.33 (m, 4H), 4.12 (br s, 1H), 3.96 (s, 3H), 3.81-3.77 (d, J=12 Hz, 2H), 2.96-2.85 (q, J=11.7 Hz, 2H), 2.44 (br s, 2H), 1.86-1.83 (d, J=10.8 Hz, 2H). LCMS m/z 501 [M+H−1], 503 [M+H+1].

Example 12

3-(1-((3-Chloro-4-methoxyphenyl)sulfonyl)piperidin-4-yl)-2-(2,4-dichlorophenyl)-3H-imidazo[4,5-b]pyridine (43)

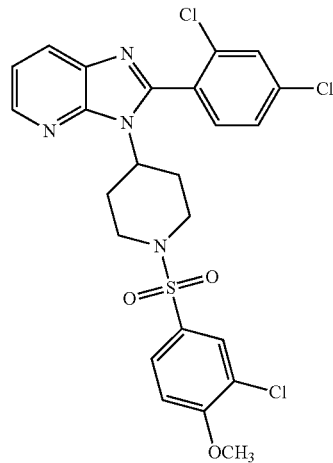

-continued

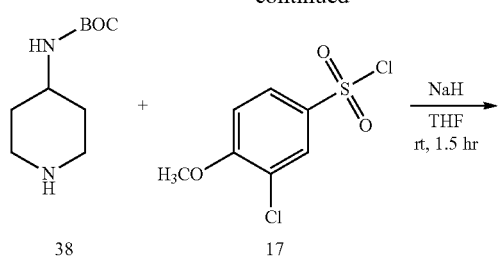

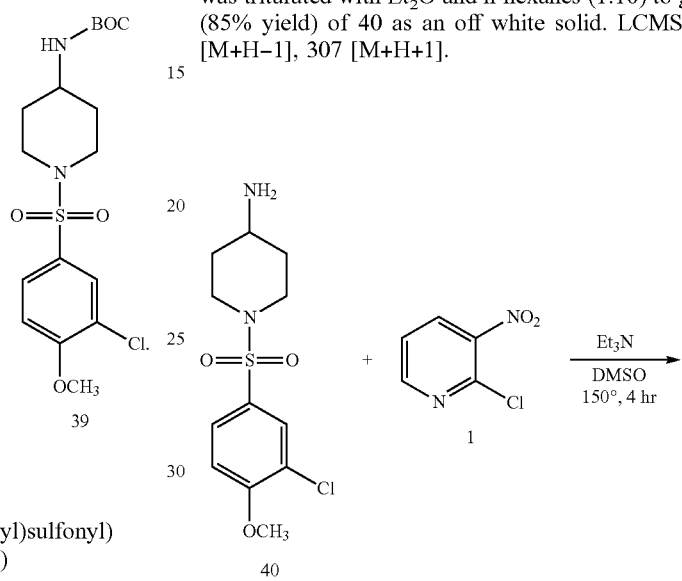

tert-Butyl (1-((3-chloro-4-methoxyphenyl)sulfonyl)piperidin-4-yl)carbamate (39)

NaH (1.44 g, 29.94 mmol) was added to a stirred solution of 38 (3.0 g, 14.97 mmol) in anhydrous THF (30 mL) at 0° C. The reaction mixture was stirred for 15 min, then 17 (3.67 g, 14.97 mmol) was added dropwise. The resulting mixture was warmed to rt and stirred at rt for 1 hr. Ice-cold H$_2$O was added and the resulting mixture was extracted with EtOAc. The combined organic layers were dried over Na$_2$SO$_4$ and concentrated in vacuo to give the crude product as an off white solid. This was washed with n-hexane to give pure 39 (3.3 g, 69% yield) as an off white solid. LCMS m/z 305 [M+H−100−1], 307 [M+H−100+1], 405 [M+H−1], 407 [M+H+1].

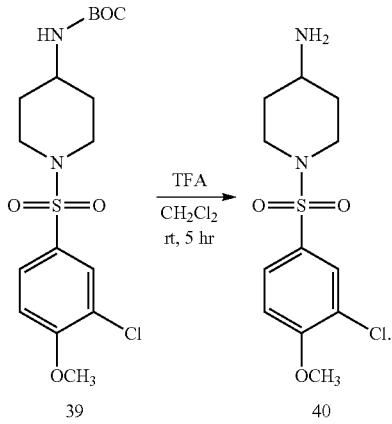 [SMILES: COc1ccc(S(=O)(=O)N2CCC(NC(=O)OC(C)(C)C)CC2)cc1Cl ; COc1ccc(S(=O)(=O)N2CCC(N)CC2)cc1Cl]

1-((3-Chloro-4-methoxyphenyl)sulfonyl)piperidin-4-amine (40)

TFA (15 mL) was added to a stirred solution of 39 (5 g, 12.34 mmol) in anhydrous CH$_2$Cl$_2$ (50 mL) at 0° C. The reaction mixture was allowed to warm to rt and stirred for 5 hr. The reaction mixture was basified with saturated NaHCO$_3$ solution, then extracted with CH$_2$Cl$_2$. The organic layer was washed with H$_2$O, followed by brine solution and dried over anhydrous Na$_2$SO$_4$. The organic layer concentrated in vacuo to give crude 40 as a pale yellow solid. This was triturated with Et$_2$O and n-hexanes (1:10) to give 3.2 g (85% yield) of 40 as an off white solid. LCMS m/z 305 [M+H−1], 307 [M+H+1].

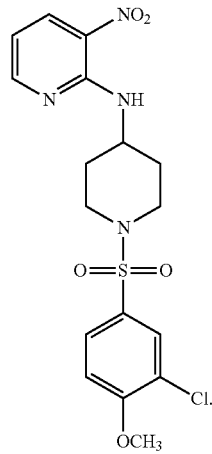

N-(1-((3-Chloro-4-methoxyphenyl)sulfonyl)piperidin-4-yl)-3-nitropyridin-2-amine (25)

Et$_3$N (1.9 mL, 13.64 mmol) was added to a stirred solution of 40 (3.2 g, 10.49 mmol) and 1 (1.65 g, 10.49 mmol) in anhydrous DMSO (160 mL) at rt. The resulting reaction mixture was stirred at 150° C. for 4 hr. After the reaction was complete, it was cooled to rt and poured into brine solution and the resulting mixture was extracted with EtOAc. The combined organic layers were dried over anhydrous Na$_2$SO$_4$ and concentrated in vacuo to give the crude compound as a yellow solid. This was triturated with Et$_2$O and hexanes (1:10) to give 4.1 g (91% yield) of 25 as a yellow solid. LCMS m/z 427 [M+H−1], 429 [M+H+1].

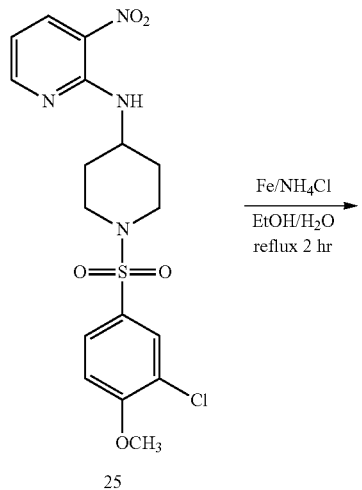

25

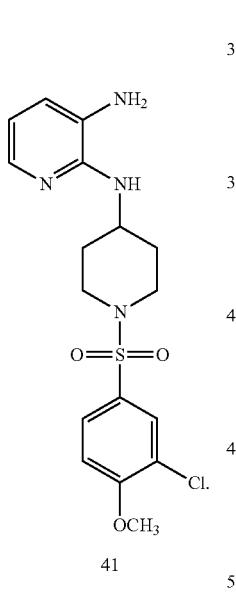

41

N$^2$-(1-((3-Chloro-4-methoxyphenyl)sulfonyl)piperidin-4-yl)pyridine-2,3-diamine (41)

A mixture of 25 (4.1 g, 9.60 mmol), iron powder (2.68 g, 48.02 mmol) and NH$_4$Cl (0.77 g, 14.40 mmol) in EtOH (40 mL) and H$_2$O (10 mL) was refluxed for 2 hr. The reaction mixture was filtered through a pad of Celite and the filtrate was concentrated to remove the EtOH. The remaining aqueous mixture was diluted with H$_2$O and extracted with EtOAc. The organic layer was dried over anhydrous Na$_2$SO$_4$ and concentrated in vacuo to give 41 (3.0 g, 79% yield) as a brown solid which was used in the next step without any further purification. LCMS m/z 397 [M+H−1], 399 [M+H+1].

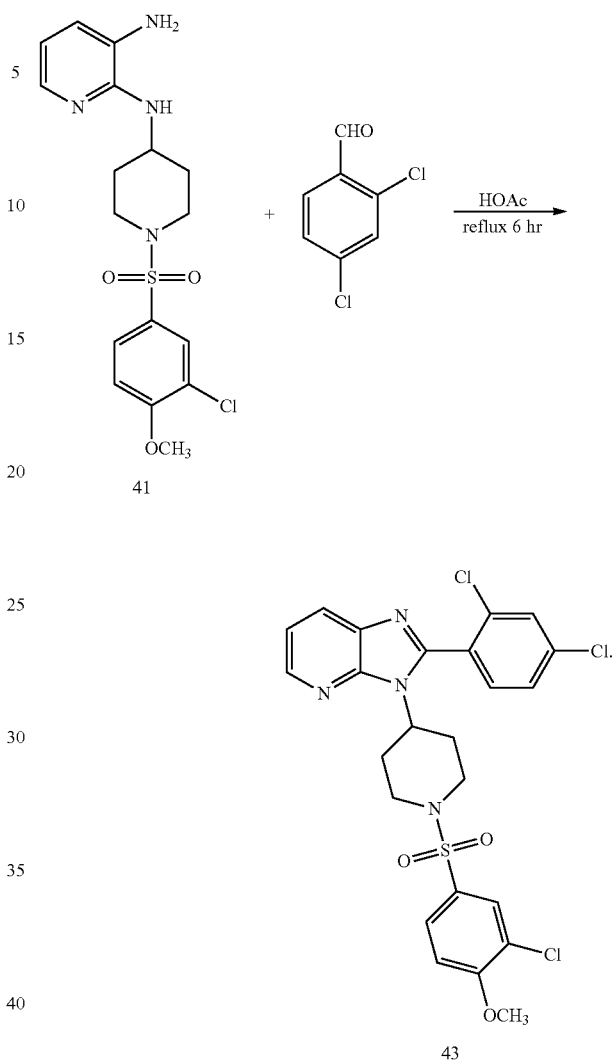

3-(1-((3-Chloro-4-methoxyphenyl)sulfonyl)piperidin-4-yl)-2-(2,4-dichlorophenyl)-3H-imidazo[4,5-b]pyridine (43)

A solution of 41 (0.2 g, 0.503 mmol) and 42 (0.0881 g, 0.503 mmol) in HOAc (6 mL) was heated refluxed for 6 hr. After the reaction was complete, the reaction mixture was cooled to rt basified with saturated NaHCO$_3$ solution. The resulting mixture was extracted with EtOAc and the organic layer was dried over anhydrous Na$_2$SO$_4$ then concentrated in vacuo to give the crude product as a yellow solid. This was purified by flash column chromatography using 100-200 mesh silica gel. The desired product was eluted in 50% EtOAc in pet-ether to obtain 0.059 g (21%) of pure 43 as a pale yellow solid. $^1$H NMR (DMSO-d$_6$) δ 8.41-8.39 (dd, J=4.65 Hz, 1H), 8.14-8.11 (dd, J=8.1 Hz, 1H), 7.85-7.84 (d, J=1.8 Hz, 1H), 7.75-7.57 (m, 4H), 7.38-7.33 (m, 2H), 4.02-3.96 (m, 1H), 3.96 (s, 3H), 3.77-3.74 (d, J=9.9 Hz, 2H), 3.0 (br s, 2H), 2.42 (br s, 2H), 1.87 (br s, 2H). LCMS m/z 551 [M+H−1], 553 [M+H+1], 555 [M+H+3], 557 [M+H+5].

Example 13

2-(3-Chloropyridin-4-yl)-3-(1-((2,2-difluorobenzo[d][1,3]dioxol-5-yl)sulfonyl)piperidin-4-yl)-5-methyl-3H-imidazo[4,5-b]pyridine (51)

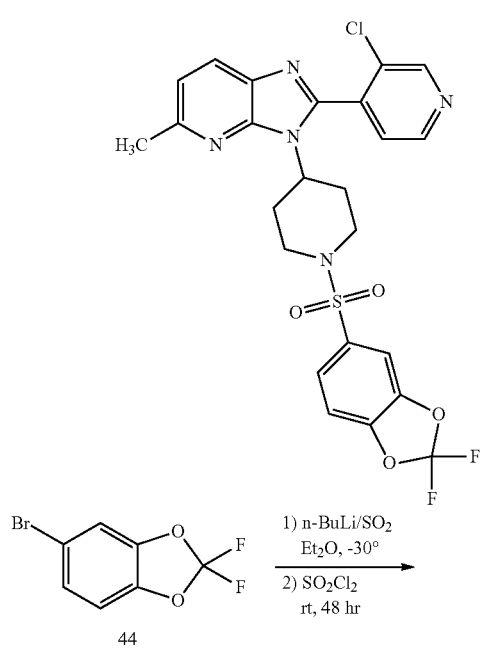

2,2-Difluorobenzo[d][1,3]dioxole-5-sulfonyl chloride (45)

N-BuLi (1.6 M) (16.8 mL, 42.194 mmol) was added dropwise to a stirred solution of 44 (10 g, 42.194 mmol) in anhydrous Et$_2$O (100 mL) at −30° C. The reaction mixture was stirred for 10 min and then SO$_2$Cl$_2$ (3.41 mL, 42.19 mmol) was added dropwise. The resulting mixture was stirred at −30° C. for 1 hr, then warmed to rt and stirred at rt for 48 hr. The resulting reaction mixture was used in the next step without workup or purification. $^1$H NMR (DMSO-d$_6$) δ 7.92-7.89 (dd, J=8.4 HZ, J=2.0 Hz, 1H), 7.76 (d, J=2.0 Hz, 1H), 7.30 (d, J=8.8 Hz, 1H). IR (KBr pellet) 1387, 1167 cm$^{-1}$.

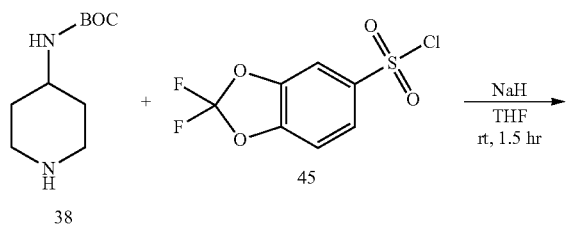

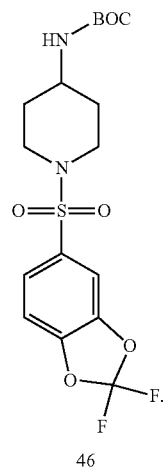

tert-Butyl (1-((2,2-difluorobenzo[d][1,3]dioxol-5-yl)sulfonyl)piperidin-4-yl)carbamate (46)

NaH (3.5 g, 74.89 mmol) was added to a stirred solution of 38 (7.5 g, 37.44 mmol) in anhydrous THF (80 mL) at 0° C. The reaction mixture was stirred for 15 min, then 45 (9.31 g, 37.44 mmol) was added dropwise. The resulting mixture was warmed to rt and stirred at rt for 1 hr. Ice-cold H$_2$O was added and the resulting mixture was extracted with EtOAc. The combined organic layers were dried over Na$_2$SO$_4$ and concentrated in vacuo to give the product 46 (8 g, 51% yield) as an off white solid, which was suitable for use in the next step without purification. LCMS m/z 419 [M−H].

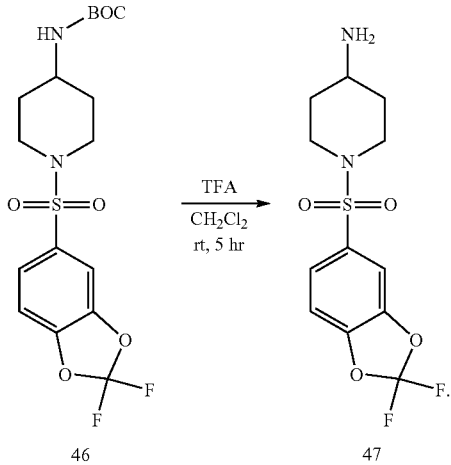 [SMILES: CC(C)(C)OC(=O)NC1CCN(S(=O)(=O)c2ccc3c(c2)OC(F)(F)O3)CC1 ; NC1CCN(S(=O)(=O)c2ccc3c(c2)OC(F)(F)O3)CC1]

1-((2,2-difluorobenzo[d][1,3]dioxol-5-yl)sulfonyl0piperidin-4-amine (47)

TFA (24 mL) was added to a stirred solution of 46 (8 g, 19.02 mmol) in anhydrous CH$_2$Cl$_2$ (80 mL) at 0° C. The reaction mixture was allowed to warm to rt and stirred for 5 hr. The reaction mixture was basified with saturated NaHCO$_3$ solution, then extracted with CH$_2$Cl$_2$. The organic layer was washed with H$_2$O, followed by brine solution and dried over anhydrous Na$_2$SO$_4$. The organic layer concentrated in vacuo to give 47 (5 g, 83% yield) as an off white solid. This was used in the next step as is without any further purification. LCMS m/z 321 [M+H].

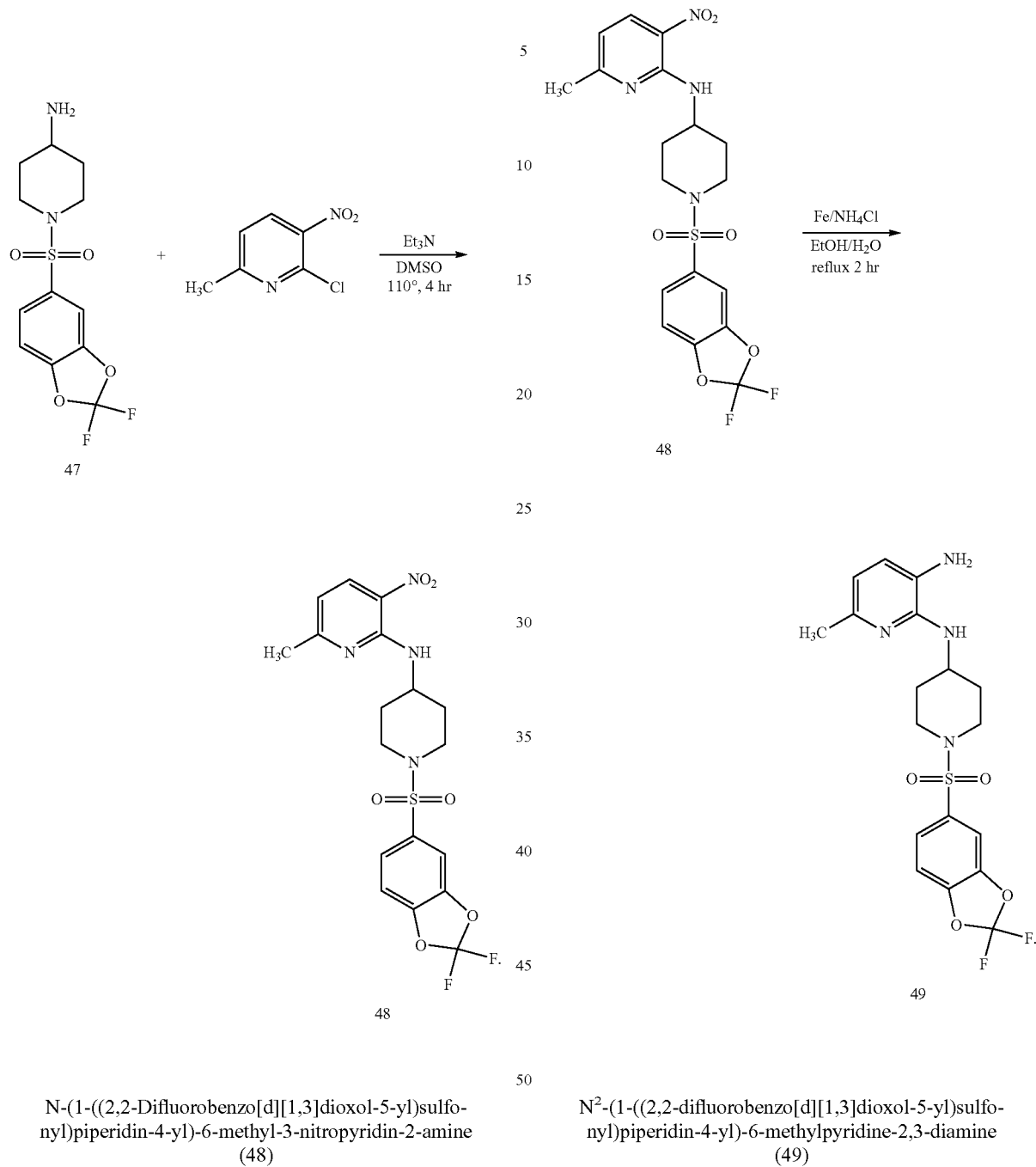

N-(1-((2,2-Difluorobenzo[d][1,3]dioxol-5-yl)sulfonyl)piperidin-4-yl)-6-methyl-3-nitropyridin-2-amine (48)

Et₃N (2.8 mL, 20.31 mmol) was added to a stirred solution of 47 (5 g, 15.62 mmol) and 9 (2.6 g, 15.62 mmol) in anhydrous DMSO (26 mL) at rt. The resulting reaction mixture was stirred at 110° C. for 4 hr. After the reaction was complete, it was cooled to rt and poured into brine solution and the resulting mixture was extracted with EtOAc. The combined organic layers were dried over anhydrous Na₂SO₄ and concentrated in vacuo to give 48 (2.5 g, 85% yield) as a yellow solid. This was used in the next step as is without any further purification. LCMS m/z 457 [M+H].

N²-(1-((2,2-difluorobenzo[d][1,3]dioxol-5-yl)sulfonyl)piperidin-4-yl)-6-methylpyridine-2,3-diamine (49)

A mixture of 48 (2.5 g, 5.4774 mmol), iron powder (1.52 g, 27.38 mmol) and NH₄Cl (0.43 g, 8.216 mmol) in EtOH (25 mL) and H₂O (7 mL) was refluxed for 2 hr. The reaction mixture was filtered through a pad of Celite and the filtrate was concentrated to remove the EtOH. The remaining aqueous mixture was diluted with H₂O and extracted with EtOAc. The organic layer was dried over anhydrous Na₂SO₄ and concentrated in vacuo to give 49 (1.5 g, 64% yield) as a brown liquid which was used in the next step without any further purification. LCMS m/z 427 [M+H].

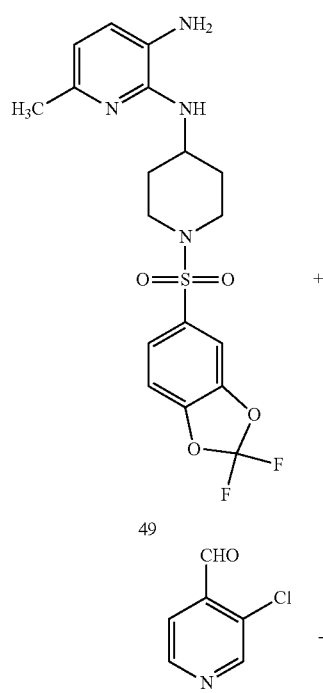

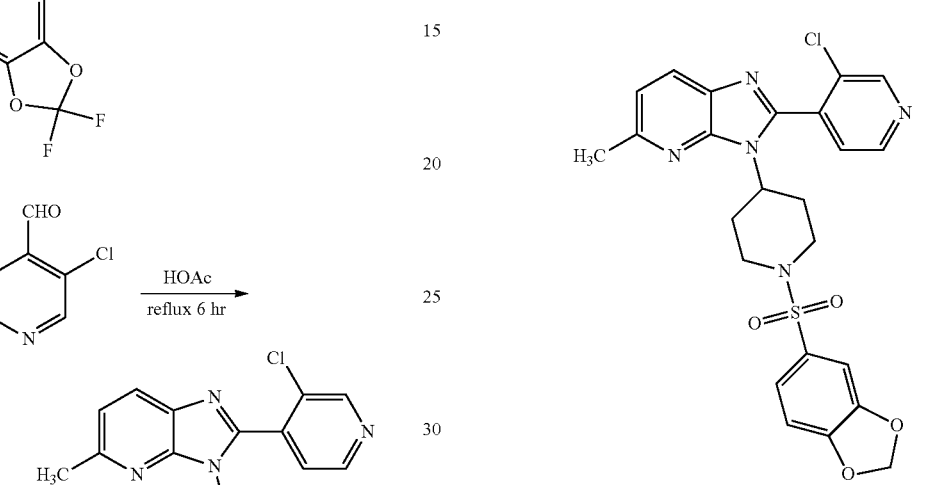

Hz, 1H), 7.85 (s, 1H), 7.76-7.65 (m, 3H), 7.25-7.23 (d, J=8.1 Hz, 1H), 3.98-3.87 (m, 1H), 3.77-3.73 (d, J=11.1 Hz, 2H), 2.96-288 (t, J=11.4 Hz, 2H), 2.63-2.62 (d, J=4.8 Hz, 2H), 2.42 (s, 3H), 1.96-1.89 (t, J=10.8 Hz, 2H). LCMS m/z 548 [M+H−1], 550 [M+H+1].

Example 14

3-(1-(Benzo[d][1,3]dioxol-5-ylsulfonyl)piperidin-4-yl)-2-(3-chloropyridin-4-yl)-5-methyl-3H-imidazo[4,5-b]pyridine (56)

2-(3-Chloropyridin-4-yl)-3-(1-((2,2-difluorobenzo[d][1,3]dioxol-5-yl)sulfonyl)piperidin-4-yl)-5-methyl-3H-imidazo[4,5-b]pyridine (51)

A solution of 49 (0.100 g, 0.234 mmol) and 50 (0.0332 g, 0.2343 mmol) in HOAc (3 mL) was heated refluxed for 6 hr. After the reaction was complete, the reaction mixture was cooled to rt basified with saturated NaHCO₃ solution. The resulting mixture was extracted with EtOAc and the organic layer was dried over anhydrous Na₂SO₄ then concentrated in vacuo to give the crude product as a yellow solid. This was purified by flash column chromatography using 100-200 mesh silica gel. The desired product was eluted in 50% EtOAc in pet-ether to obtain 0.015 g (12%) of pure 51 as an off white solid. ¹H NMR (DMSO-d₆) δ 8.88-8.85 (d, J=9.9 Hz, 1H), 8.73-8.71 (d, J=4.8 Hz, 1H), 8.04-8.01 (d, J=8.1 tert-Butyl (1-(benzo[d][1,3]dioxol-5-ylsulfonyl)piperidin-4-yl)carbamate (52)

NaH (0.23 g, 4.9939 mmol) was added to a stirred solution of 38 (0.5 g, 2.49 mmol) in anhydrous THF (15 mL) at 0° C. The reaction mixture was stirred for 15 min, then 7 (0.55 g, 2.49 mmol) was added dropwise. The resulting mixture was warmed to rt and stirred at rt for 1 hr. Ice-cold H₂O was added and the resulting mixture was extracted with EtOAc. The combined organic layers were dried over Na₂SO₄ and concentrated in vacuo to give the product as an off white solid. This was washed with n-hexane to give pure 52 (0.8 g, 83% yield) as an off white solid. LCMS m/z 385 [M+H].

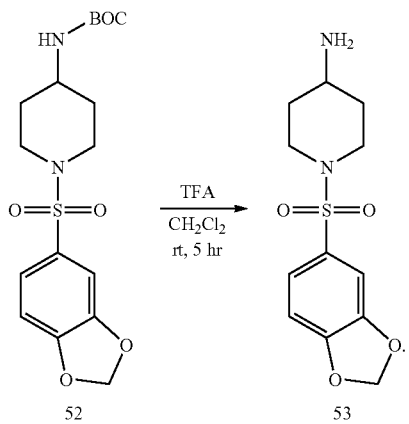 [SMILES: CC(C)(C)OC(=O)NC1CCN(S(=O)(=O)c2ccc3c(c2)OCO3)CC1 ; NC1CCN(S(=O)(=O)c2ccc3c(c2)OCO3)CC1]

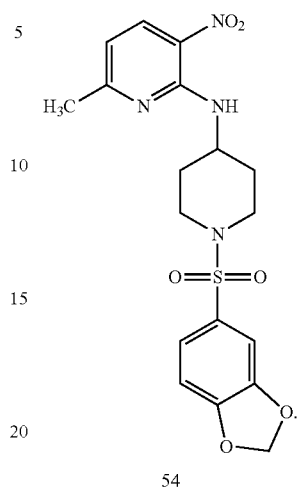

54

N-(1-(Benzo[d][1,3]dioxol-5-ylsulfonyl)piperidin-4-yl)-6-methyl-3-nitropyridin-2-amine (54)

1-(Benzo[d][1,3]dioxol-5-yl)sulfonyl)piperidin-4-amine (53)

TFA (2 mL) was added to a stirred solution of 52 (0.8 g, 2.08 mmol) in anhydrous CH₂Cl₂ (10 mL) at 0° C. The reaction mixture was allowed to warm to rt and stirred for 5 hr. The reaction mixture was basified with saturated NaHCO₃ solution, then extracted with CH₂Cl₂. The organic layer was washed with H₂O, followed by brine solution and dried over anhydrous Na₂SO₄. The organic layer concentrated in vacuo to give 53 (0.4 g, 68% yield) as an off white solid. This was used in the next step as is without any further purification. LCMS m/z 285 [M+H].

Et₃N (0.25 mL, 1.828 mmol) was added to a stirred solution of 53 (0.4 g, 1.406 mmol) and 9 (0.24 g, 1.406 mmol) in anhydrous DMSO (15 mL) at rt. The resulting reaction mixture was stirred at 150° C. for 4 hr. After the reaction was complete, it was cooled to rt and poured into brine solution and the resulting mixture was extracted with EtOAc. The combined organic layers were dried over anhydrous Na₂SO₄ and concentrated in vacuo to give the crude product as a yellow solid. This was washed with Et₂O and n-hexane (1:10) to give 0.5 g (85% yield) of 54 as a yellow solid. LCMS m/z 421 [M+H].

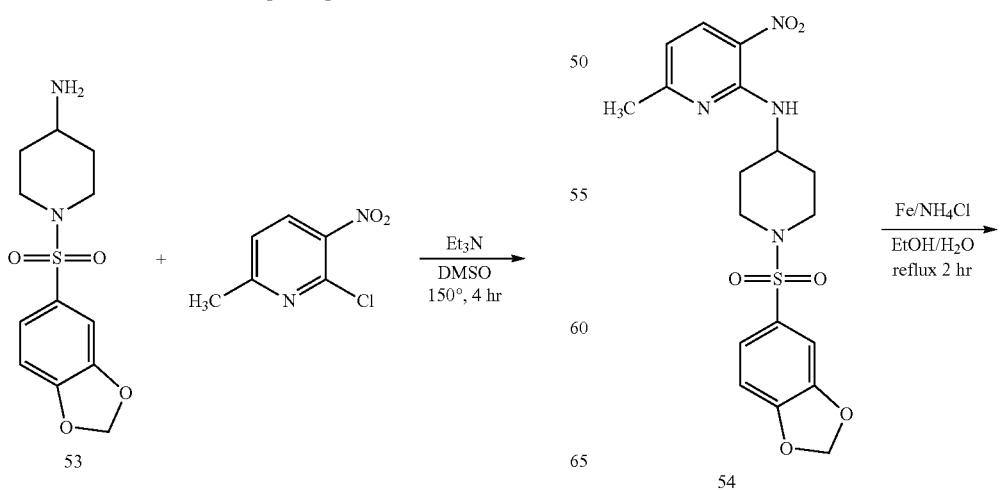

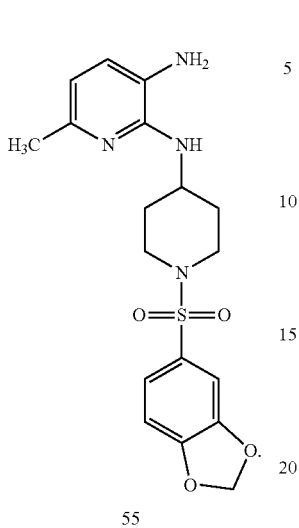

N²-(1-(Benzo[d][1,3]dioxol-5-ylsulfonyl)piperidin-4-yl)-6-methylpyridine-2,3-diamine (55)

A mixture of 54 (0.5 g, 1.233 mmol), iron powder (0.34 g, 6.166 mmol) and NH₄Cl (0.099 g, 1.849 mmol) in EtOH (10 mL) and H₂O (3 mL) was refluxed for 2 hr. The reaction mixture was filtered through a pad of Celite and the filtrate was concentrated to remove the EtOH. The remaining aqueous mixture was diluted with H₂O and extracted with EtOAc. The organic layer was dried over anhydrous Na₂SO₄ and concentrated in vacuo to give 55 (0.15 g, 31% yield) as a brown solid which was used in the next step without any further purification. LCMS m/z 391 [M+H].

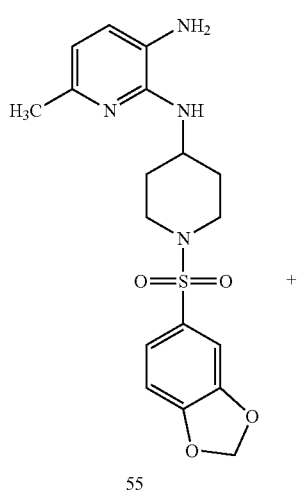

55

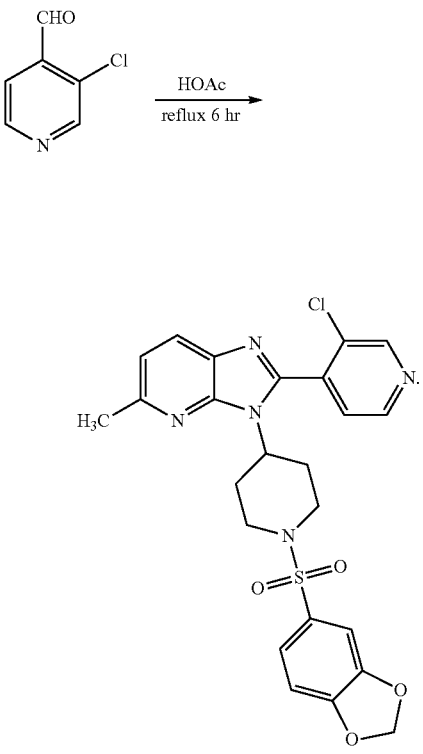

56

3-(1-(Benzo[d][1,3]dioxol-5-ylsulfonyl)piperidin-4-yl)-2-(3-chloropyridin-4-yl)-5-methyl-3H-imidazo[4,5-b]pyridine (56)

A solution of 55 (0.075 g, 0.192 mmol) and 50 (0.0272 g, 0.192 mmol) in HOAc (3 mL) was heated refluxed for 6 hr. After the reaction was complete, the reaction mixture was cooled to rt basified with saturated NaHCO₃ solution. The resulting mixture was extracted with EtOAc and the organic layer was dried over anhydrous Na₂SO₄ then concentrated in vacuo to give the crude product as a yellow solid. This was purified by flash column chromatography using 100-200 mesh silica gel. The desired product was eluted in 50% EtOAc in pet-ether to obtain 0.011 g (11%) of pure 56 as a pale yellow solid. ¹H NMR (DMSO-d₆) δ 8.84 (s, 1H), 8.70-8.68 (d, J= 4.8 Hz, 1H), 8.03-8.01 (d, J=8.1 Hz, 1H), 7.68-7.66 (d, J=4.8 Hz, 1H), 7.29-7.21 (m, 3H), 7.13-7.10 (d, J=8.4 Hz, 1H), 6.17 (s, 2H), 3.98 (br s, 1H), 3.73-3.69 (d, J=11.1 Hz, 2H), 2.86 (br s, 2H), 2.64 (s, 3H), 2.38-2.26 (m, 2H), 1.91-1.88 (d, J=11.4 Hz, 2H). LCMS m/z 512 [M+H−1], 514 [M+H+1].

Example 15

2-(2-Chloropyridin-3-yl)-3-(1-((2,2-difluorobenzo[d][1,3]dioxol-5-yl)sulfonyl)piperidin-4-yl)-5-methyl-3H-imidazo[4,5-b]pyridine (58)

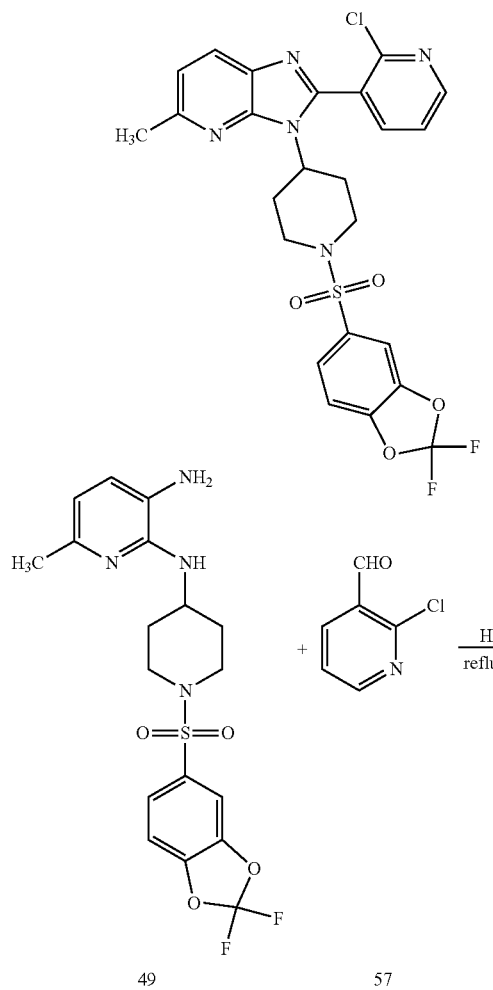

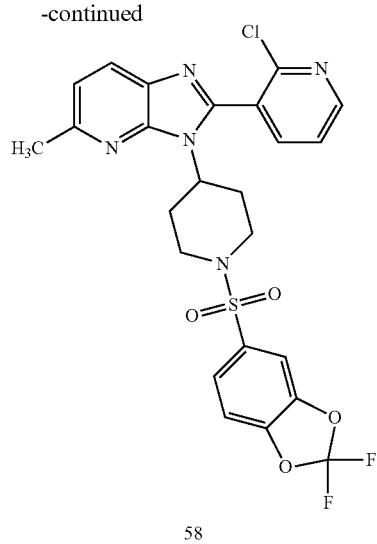

2-(2-Chloropyridin-3-yl)-3-(1-((2,2-difluorobenzo[d][1,3]dioxol-5-yl)sulfonyl)piperidin-4-yl)-5-methyl-3H-imidazo[4,5-b]pyridine (58)

A solution of 49 (0.100 g, 0.234 mmol) and 57 (0.0332 g, 0.2343 mmol) in HOAc (3 mL) was heated refluxed for 6 hr. After the reaction was complete, the reaction mixture was cooled to rt basified with saturated $NaHCO_3$ solution. The resulting mixture was extracted with EtOAc and the organic layer was dried over anhydrous $Na_2SO_4$ then concentrated in vacuo to give the crude product as a yellow solid. This was purified by preparative HPLC to give 0.014 g (12%) of pure 58 as an off white solid. $^1$H NMR (DMSO-$d_6$) δ 8.61-8.64 (dd, J=11.4 Hz, 1H), 8.10-8.12 (d, J=7.2 Hz, 1H), 7.99-8.01 (d, J=8Hz, 1H), 7.84 (s, 1H), 7.57-7.65 (m, 3H), 7.22-7.23 (d, J= 7.6Hz, 1H), 4.01 (m, 1H), 3.74-3.78 (m, 2H), 2.92-3.01 (m, 2H), 2.63, (s, 3H), 2.45 (m, 2H), 1.91 (m, 2H). LCMS m/z 548 [M+H−1], 550 [M+H+1].

TABLE 2

Additional examples were prepared as according to the described methods above, or similar methods, or were purchased from commercial vendors.

| No. | | Example | LCMS m/z [M + H] | SCHEME |
|---|---|---|---|---|
| 1. | | Example 16 | m/z 483 [M + H − 1], 485 [M + H + 1] | 1 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 2. | (2-phenyl-imidazo[4,5-b]pyridine with N-piperidinyl-sulfonyl-4-methylphenyl) | Example 17 | m/z 433 [M + H] | Commercial |
| 3. | (2-phenyl-imidazo[4,5-b]pyridine with N-piperidinyl-sulfonyl-3-fluoro-4-methoxyphenyl) | Example 18 | m/z 467 [M + H] | 1 |
| 4. | (2-phenyl-imidazo[4,5-b]pyridine with N-piperidinyl-sulfonyl-4-methoxyphenyl) | Example 19 | m/z 449 [M + H] | 1 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 5. | [2-phenyl-imidazo[4,5-b]pyridine linked to piperidine-N-sulfonyl-(3-chloro-4-methylphenyl)] | Example 20 | m/z 467 [M +H − 1], 469 [M + H +1] | 1 |
| 6. | [2-phenyl-imidazo[4,5-b]pyridine linked to piperidine-N-carbonyl-(3-chloro-4-methoxyphenyl)] | Example 21 | m/z 447 [M + H − 1], 449 [M + H + 1] | 1a |
| 7. | [2-(2-chlorophenyl)-imidazo[4,5-b]pyridine linked to piperidine-N-sulfonyl-(3-chloro-4-methoxyphenyl)] | Example 6 | m/z 517 [M + H − 1], 519 [M + H + 1], 521 [M + H + 3] | 2 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 8. | | Example 22 | m/z 517 [M + H − 1], 519 [M + H + 1], 521 [M + H + 3] | 2 |
| 9. | | Example 23 | m/z 497 [M + H − 1], 499 [M + H + 1] | 2 |
| 10. | | Example 24 | m/z 497 [M + H − 1], 499 [M + H + 1] | 2 |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 11. | 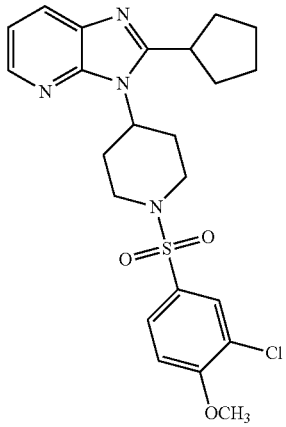 [SMILES: COc1ccc(S(=O)(=O)N2CCC(n3c(C4CCCC4)nc4cccnc43)CC2)cc1Cl] | Example 25 | m/z 475 [M + H − 1], 477 [M + H + 1] | 2 |
| 12. | 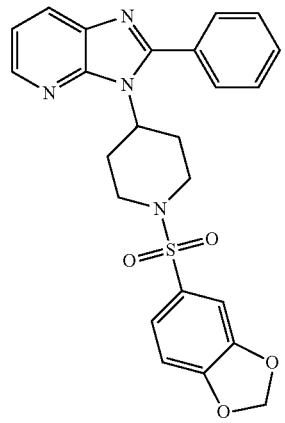 [SMILES: O=S(=O)(c1ccc2c(c1)OCO2)N1CCC(n2c(-c3ccccc3)nc3cccnc32)CC1] | Example 5 | m/z 463 [M + H] | 1 |
| 13. | 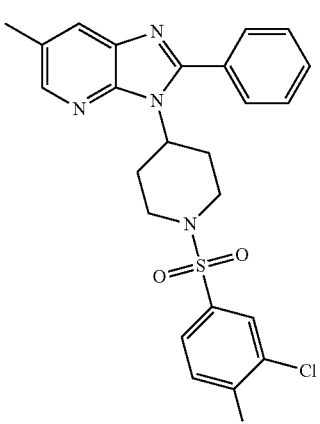 | Example 26 | m/z 497 [M + H − 1], 499 [M + H + 1] | 1 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 14. | Example 3 | m/z 497 [M + H − 1], 499 [M + H + 1] | 1 |
| 15. | Example 27 | m/z 484 [M + H − 1], 486 [M + H + 1] | 2 |
| 16. | Example 28 | m/z 484 [M + H − 1], 486 [M + H + 1] | 2 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 17. | (2-(4-chlorophenyl)-imidazo[4,5-b]pyridine with piperidine-N-sulfonyl-3-chloro-4-methoxyphenyl) | Example 29 | m/z 517 [M + H − 1], 519 [M + H + 1], 521 [M + H + 3] | 2 |
| 18. | (2-(2-methylphenyl)-imidazo[4,5-b]pyridine with piperidine-N-sulfonyl-3-chloro-4-methoxyphenyl) | Example 30 | m/z 497 [M + H − 1], 499 [M + H + 1] | 2 |
| 19. | (2-cyclohexyl-imidazo[4,5-b]pyridine with piperidine-N-sulfonyl-3-chloro-4-methoxyphenyl) | Example 31 | m/z 489 [M + H − 1], 491 [M + H + 1] | 2 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 20. | Example 32 | m/z 473 [M + H − 1], 475 [M + H + 1] | 2 |
| 21. | Example 33 | m/z 523 [M + H − 1], 525 [M + H + 1] | 2 |
| 22. | Example 34 | m/z 523 [M + H − 1], 525 [M + H + 1] | 2 |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 23. | 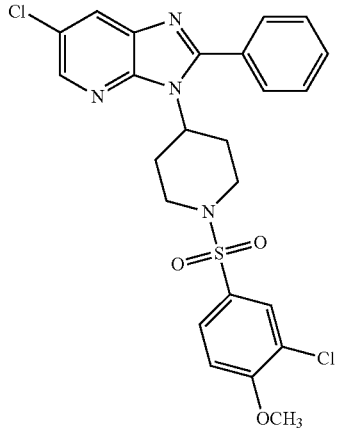 [SMILES: COc1ccc(S(=O)(=O)N2CCC(n3c(-c4ccccc4)nc4cc(Cl)cnc43)CC2)cc1Cl] | Example 35 | m/z 517 [M + H − 1], 519 [M + H + 1], 521 [M + H + 3] | 3 |
| 24. | 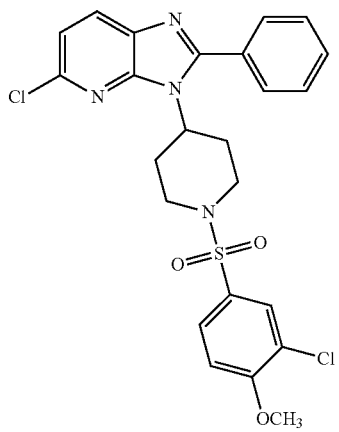 [SMILES: COc1ccc(S(=O)(=O)N2CCC(n3c(-c4ccccc4)nc4ccc(Cl)nc43)CC2)cc1Cl] | Example 36 | m/z 517 [M + H − 1], 519 [M + H + 1], 521 [M + H + 1] | 3 |
| 25. | 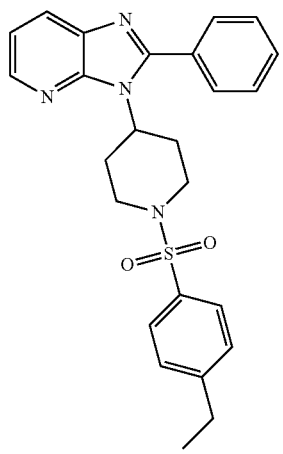 [SMILES: CCc1ccc(S(=O)(=O)N2CCC(n3c(-c4ccccc4)nc4cccnc43)CC2)cc1] | Example 4 | m/z 447 [M + H] | 1 |

TABLE 2-continued
Additional examples were prepared as according to the described methods above, or similar methods, or were purchased from commercial vendors.
| No. | | Example | LCMS m/z [M + H] | SCHEME |
|---|---|---|---|---|
| 26. | 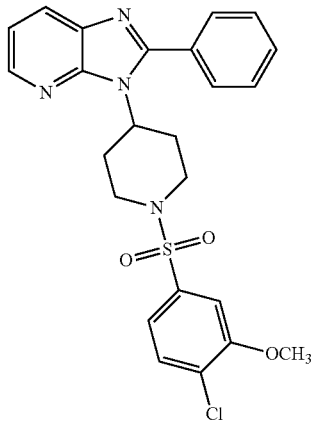 [SMILES: COc1cc(S(=O)(=O)N2CCC(n3c(-c4ccccc4)nc4cccnc43)CC2)ccc1Cl] | Example 37 | m/z 483 [M + H − 1], 485 [M + H + 1] | 1 |
| 27. | 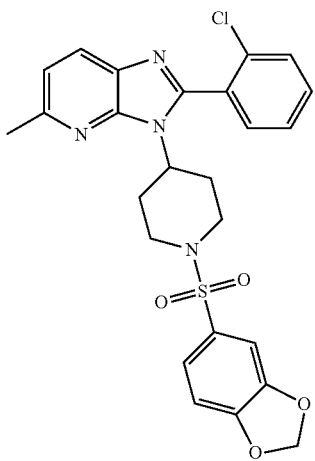 [SMILES: Cc1ccc2nc(-c3ccccc3Cl)n(C3CCN(S(=O)(=O)c4ccc5c(c4)OCO5)CC3)c2n1] | Example 2 | m/z 511 [M + H − 1], 513 [M + H + 1] | 1 |
| 28. | 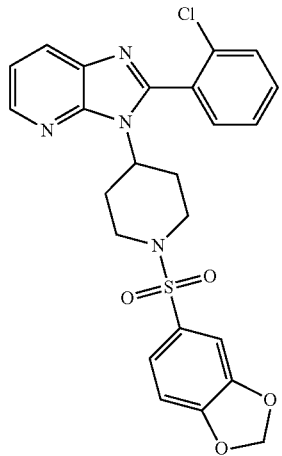 [SMILES: O=S(=O)(c1ccc2c(c1)OCO2)N1CCC(n2c(-c3ccccc3Cl)nc3cccnc32)CC1] | Example 1 | m/z 497 [M + H − 1], 499 [M + H + 1] | 1 |

TABLE 2-continued

Additional examples were prepared as according to the described methods above, or similar methods, or were purchased from commercial vendors.

| No. | Structure | Example | LCMS m/z [M + H] | SCHEME |
|---|---|---|---|---|
| 29. | | Example 7 | m/z 515 [M + H − 1], 517 [M + H + 1], 519 [M + H + 3] | 1 |
| 30. | | Example 8 | m/z 515 [M + H − 1], 517 [M + H + 1] | 1 |
| 31. | | Example 9 | m/z 499 [M + H − 1], 501 [M + H + 1] | 2 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 32. | Example 10 | m/z 501 [M + H − 1], 503 [M + H + 1], 505 [M + H + 3] | 1 |
| 33. | Example 11 | m/z 501 [M + H − 1], 503 [M + H + 1] | 1 |
| 34. | Example 12 | m/z 551 [M + H − 1], 553 [M + H + 1], 555 [M + H + 3], 557 [M + H + 5] | 3 |

TABLE 2-continued

Additional examples were prepared as according to the described methods above, or similar methods, or were purchased from commercial vendors.

| No. | Example | LCMS m/z [M + H] | SCHEME |
|---|---|---|---|
| 35. | Example 13 | m/z 548 [M + H − 1], 550 [M + H + 1] | 3 |
| 36. | Example 14 | m/z 512 [M + H − 1], 514 [M + H + 1] | 3 |
| 37. | Example 15 | m/z 548 [M + H − 1], 550 [M + H + 1] | 3 |

Assays for Detecting and Measuring the Effect of Compounds on dF508-CFTR Channels CFRT-YFP High Throughput Assay-CFTR Corrector Protocol:

This protocol is designed to selectively screen small molecule compounds for F508del CFTR corrector activities in the HTS YFP flux assay. In this protocol, the cells are incubated with testing compounds for 24 hours, washed with PBS, stimulated with forskolin and a standard potentiator, and read on a 384-well HTS plate reader, such as the Hamamatsu FDDD-6000.

YFP fluorescence intensity is acquired at high speed before and after iodide buffer is injected to the assay cells. Iodide enters the cells via active CFTR channels in the plasma membrane, and quenches the YFP fluorescence. The rate of fluorescence quenching is proportionally related to the total CFTR activities in the cell membrane. dF508-CFTR corrector accelerates YFP quenching by increasing the number of CFTR molecules in the testing cell plasma membrane.

This method was initially developed for bench top plate readers (Galietta et al., 2001), and was adapted to the HTS format (Sui et al. Assay Drug Dev. Technol. 2010).

Fisher Rat Thyroid (FRT) cells stably expressing both human ΔF508-CFTR and a halide-sensitive yellow fluorescent protein (YFP-H148Q/I152L 25,22) (Galietta et al., Am. J. Physiol Cell Physiol, 281(5), C1734, 2001) were cultured on plastic surface in Coon's modified Ham's F12 medium supplemented with FBS 10%, L-glutamine 2 mM, penicillin 100 U/ml, and streptomycin 100 µg/ml. G418 (0.75-1.0 mg/ml) and zeocin (3.2 ug/ml) were used for selection of FRT cells expressing ΔF508-CFTR and YFP. For primary screening, FRT cells were plated into 384-well black wall, transparent bottom microtiter plates (Costar; Corning Inc.) at a cell density of 20,000-40,000 per well. Test compound was applied to the cells at varying concentrations ranging from 2 nM-40 nM in either a 2-fold or 3-fold dilution series. Cells were incubated in a cell culture incubator at 37° C. with 5% $CO_2$ for 24-26 h. Assay plates were washed with DPBS media (Thermo, cat #SH30028.02) to remove unbound cells and compound. Stimulation media (25 µL) containing 20 µM Forskolin & 30 µM P3 [6-(Ethyl-phenyl-sulfonyl)-4-oxo-1,4-dihydro-quinoline-3-carboxylic acid 2-methoxy-benzylamide] in Hams F-12 coon's modified media was added to the plate wells and incubated at room temperature for 60-120 min. 25 µL of HEPES-PBS -I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al. (2010).

CFRT-YFP High Throughput Assay-CFTR Potentiator Protocol:

This protocol is designed to selectively screen small molecule compounds for F508del CFTR potentiator activities in the HTS YFP flux assay. In this protocol, the cells are incubated at 27° C. for 24 hours with homogeneously boosted dF508-CFTR expression in the cell membrane by the low temperature, washed with PBS, stimulated with forskolin, and read on a 384-well HTS plate reader, such as the Hamamatsu FDDD-6000.

YFP fluorescence intensity is acquired at high speed before and after iodide buffer is injected to the assay cells. Iodide enters the cells via active CFTR channels in the plasma membrane, and quenches the YFP fluorescence. The rate of fluorescence quenching is proportionally related to the total CFTR activities in the cell membrane. dF508del-CFTR potentiators accelerate YFP quenching by increasing CFTR activities in the testing cell plasma membrane.

This method was initially developed for bench top plate readers (Galietta et al., 2001), and was adapted to the HTS format (Sui et al. Assay Drug Dev. Technol. 2010).

Fisher Rat Thyroid (FRT) cells stably expressing both human ΔF508-CFTR and a halide-sensitive yellow fluorescent protein (YFP-H148Q/I152L 25,22) (Galietta et al., Am. J. Physiol Cell Physiol, 281(5), C1734, 2001) were cultured on plastic surface in Coon's modified Ham's F12 medium supplemented with FBS 10%, L-glutamine 2 mM, penicillin 100 U/ml, and streptomycin 100 µg/ml. G418 (0.75-1.0 mg/ml) and zeocin (3.2 ug/ml) were used for selection of FRT cells expressing ΔF508-CFTR and YFP. For primary screening, FRT cells were plated into 384-well black wall, transparent bottom microtiter plates (Costar; Corning Inc.) at a cell density of 20,000-40,000 per well. Cells were incubated in a cell culture incubator at 37° C. with 5% $CO_2$ for 24-26 h. Assay plates were washed with DPBS media (Thermo, cat #SH30028.02) to remove unbound cells. Test compound was applied to the cells at varying concentrations ranging from 2 nM-40 nM in either a 2-fold or 3-fold dilution series in DPBS and stimulated with 20 µM Forskolin (final concentration) in Hams F-12 coon's modified media. Plates were incubated at room temperature for 60-120 min. 25 µL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al (2010).

REFERENCES

Galietta, L. J., Jayaraman, S., and Verkman, A. S. Cell-based assay for high-throughput quantitative screening of CFTR chloride transport agonists, Am. J. Physiol Cell Physiol, 281(5), C1734, 2001.

Sui J, Cotard S, Andersen J, Zhu P, Staunton J, Lee M, Lin S. (2010) Optimization of a Yellow fluorescent protein-based iodide influx high-throughput screening assay for cystic fibrosis transmembrane conductance regulator (CFTR) modulators., Assay Drug Dev Technol., 2010 December; 8(6):656-68.

Cell Culture:

Primary CF airway epithelial cells were obtained from the UNC Cystic Fibrosis Tissue Procurement and Cell Culture Core. The cells are grown at 37° C. in a Heracell 150i incubator using growth media (BEGM, Fischer). Cells were then transferred to differentiation media (ALI, UNC) for a minimum of 4 weeks on coated Costar snapwells. Two days before the Ussing assay the mucus on the apical surface of the cells was aspirated after incubating with 200 µL of differentiation Media for at least thirty (30) minutes. One day before the Ussing assay test compounds were added to the basolateral surface of the cells at various test concentrations dissolved in DMSO. The same concentrations of correctors was added to 3 or 4 wells giving a n=3 or n=4 protocol.

Ussing Assay:

Ussing chambers and the associated voltage clamp were obtained from Physiologic Instruments, (San Diego, Calif.). Ussing assays were performed at the 37° C. HEPES buffered physiological saline (HB-PS) was used in apical and basolateral chambers with glucose added to the basolateral solutions. Epithelia were equilibrated for 15 minutes in the chambers while the bath temperature and transepithelial voltage stabilizes adjusts before application of voltage clamp.

Compounds were added in the following order.

| Step | Chamber |
|---|---|
| 3.0 uM Benzamil for 20 minutes | apical addition only |
| 10 uM Forskolin for 20 minutes | apical + basolateral addition |
| 10 uM Genestein for 20 minutes | apical + basolateral addition |
| 10 uM CFTR-172 for 20 minutes | apical + basolateral addition |
| 20 uM Bumetanide for 30 minutes | basolateral addition only |

The short circuit current and resistances (typically >300 Ω-cm2) from each chamber was recorded every 10 seconds on stored on a PC using Acquire and Analyze (Physiologic Instruments).

Analysis:

Efficacy of test compounds was compared using the average of the forskolin response and the CFTR-172 response of the test compound divided by the average of the forskolin response and the CFTR-172 elicited by the positive control. Normalized scores were tabulated for all compounds and concentrations.

TABLE 3

CFTR-YFP Corrector Protocol:

| No. | Example | $EC_{50}$ | $E_{MAX}$ |
|---|---|---|---|
| 1. | Example 16 | II | III |
| 2. | Example 17 | III | II |
| 3. | Example 18 | III | II |
| 4. | Example 19 | III | II |
| 5. | Example 20 | III | II |
| 6. | Example 21 | I | I |
| 7. | Example 6 | III | II |
| 8. | Example 22 | III | II |
| 9. | Example 23 | III | III |
| 10. | Example 24 | III | II |
| 11. | Example 25 | III | II |
| 12. | Example 5 | III | II |
| 13. | Example 26 | III | II |
| 14. | Example 3 | III | II |
| 15. | Example 27 | III | II |
| 16. | Example 28 | III | II |
| 17. | Example 29 | III | I |
| 18. | Example 30 | III | II |
| 19. | Example 31 | III | II |
| 20. | Example 32 | I | II |
| 21. | Example 33 | II | II |
| 22. | Example 34 | III | II |
| 23. | Example 35 | III | II |
| 24. | Example 36 | III | I |
| 25. | Example 4 | I | II |
| 26. | Example 37 | III | II |
| 27. | Example 2 | III | II |
| 28. | Example 1 | III | II |
| 29. | Example 7 | III | II |
| 30. | Example 8 | III | II |
| 31. | Example 9 | III | II |
| 32. | Example 10 | III | II |
| 33. | Example 11 | III | II |
| 34. | Example 12 | III | I |
| 35. | Example 13 | III | II |
| 36. | Example 14 | I | I |
| 37. | Example 15 | III | II |

$EC_{50}$: "III" refers to an $EC_{50}$ <10 μM, "II" refers to $EC_{50}$ range of 10-20 μM, "I" refers to $EC_{50}$ >20 μM.
% Efficacy is reported as the $E_{MAX}$ normalized to the positive control. "III" refers to $E_{MAX}$ >80%, "II" refers to a range of 80%-30%, "I" refers to a range of 30%-10%.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed:

1. A pharmaceutical composition comprising a compound of Formula V or a pharmaceutically acceptable salt, or ester thereof:

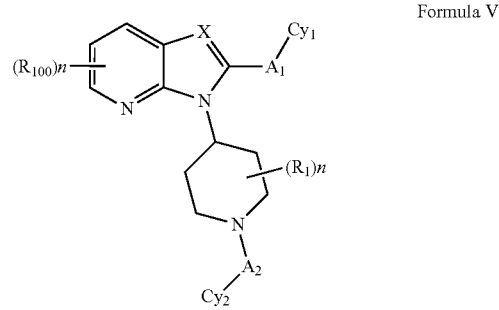

Formula V and a pharmaceutically acceptable carrier or excipient, wherein n is 0, 1, 2, or 3;

X is N;

$A_1$ is absent;

$A_2$ is —S(O)$_2$—;

$Cy_1$ is selected from:

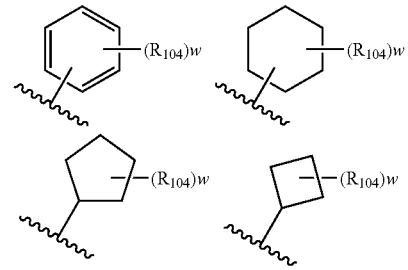

101

-continued

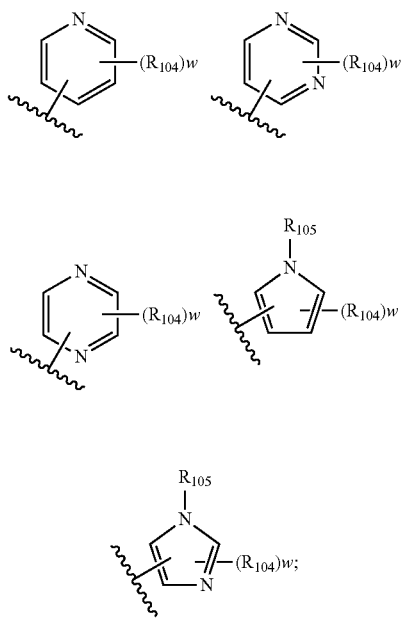

wherein w is 0 to 4, each $R_{104}$ and $R_{105}$ is independently selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, substituted heteroaryl, —$OR_{100}$, —$SR_{100}$, —$S(O)_2N(R_{100})(R_{101})$ —$NR_{100}R_{101}$, —$C(O)R_{100}$, —$C(O)OR_{100}$, —$C(O)NR_{100}R_{101}$, —$N(R_{100})C(O)R_{101}$, —$CF_3$, —CN, —$NO_2$, —$N_3$, acyl, alkoxy, substituted alkoxy, alkylamino, substituted alkylamino, dialkylamino, substituted dialkylamino, alkylthio and substituted alkylthio;

alternatively, two $R_{104}$ groups or an $R_{104}$ group with an $R_{105}$ group together with the atoms to which they are attached and any intervening atoms form an additional optionally substituted 3, 4, 5, 6 or 7 membered ring;

$R_{100}$ and $R_{101}$ are each independently hydrogen, deuterium, halogen, alkyl, cycloalkyl, substituted alkyl, alkenyl, substituted alkenyl, alkynyl, substituted alkynyl, aliphatic, substituted aliphatic, aryl and substituted aryl, heterocycle, substituted heterocycle, heteroaryl or substituted heteroaryl; alternatively, $R_{100}$ and $R_{101}$ together with the atoms to which they are attached and any intervening atoms form an optionally substituted, 3, 4, 5, 6 or 7 membered ring; and $Cy_2$ is substituted or unsubstituted phenyl.

2. The pharmaceutical composition of claim 1 wherein the compound of Formula V is selected from Table 4 or a pharmaceutically acceptable salt thereof:

102

TABLE 4

Compound No.

1.

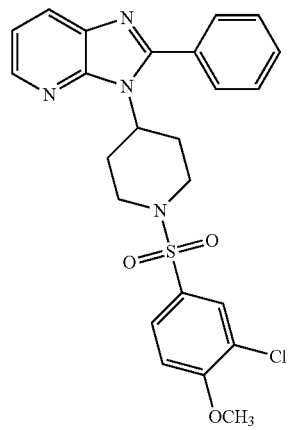 [SMILES: COc1ccc(S(=O)(=O)N2CCC(n3c(-c4ccccc4)nc4cccnc43)CC2)cc1Cl]

2.

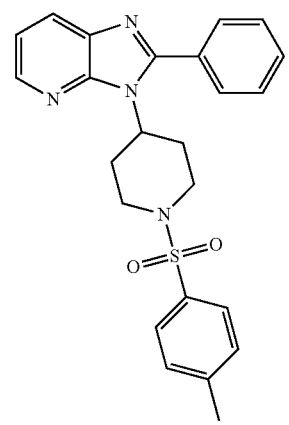 [SMILES: Cc1ccc(S(=O)(=O)N2CCC(n3c(-c4ccccc4)nc4cccnc43)CC2)cc1]

3.

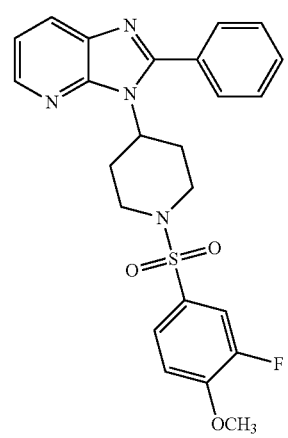 [SMILES: COc1ccc(S(=O)(=O)N2CCC(n3c(-c4ccccc4)nc4cccnc43)CC2)cc1F]

TABLE 4-continued
Compound No.
4. 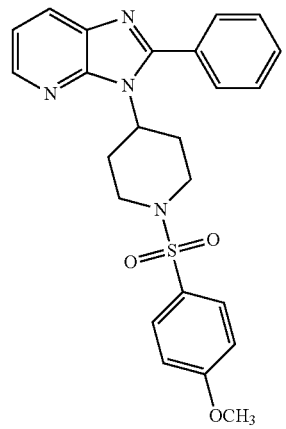 [SMILES: COc1ccc(S(=O)(=O)N2CCC(n3c(-c4ccccc4)nc4cccnc43)CC2)cc1]
5. 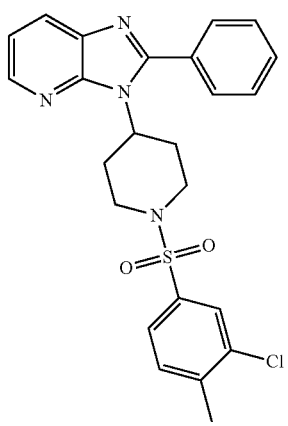 [SMILES: Cc1ccc(S(=O)(=O)N2CCC(n3c(-c4ccccc4)nc4cccnc43)CC2)cc1Cl]
7. 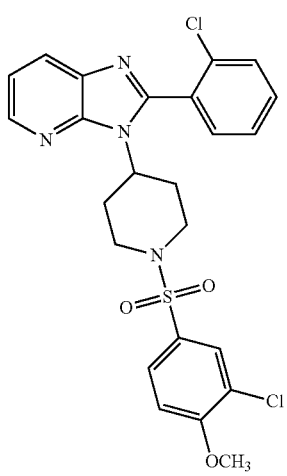 [SMILES: COc1ccc(S(=O)(=O)N2CCC(n3c(-c4ccccc4Cl)nc4cccnc43)CC2)cc1Cl]
TABLE 4-continued
Compound No.
8. 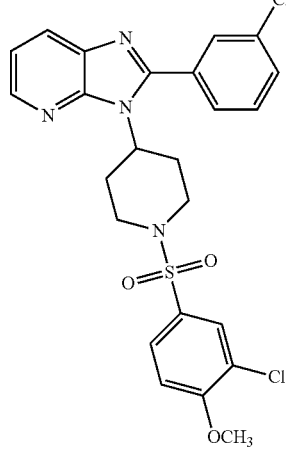
9. 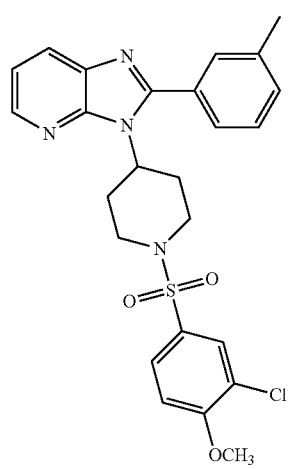 [SMILES: COc1ccc(S(=O)(=O)N2CCC(n3c(-c4cccc(C)c4)nc4cccnc43)CC2)cc1Cl]
10. 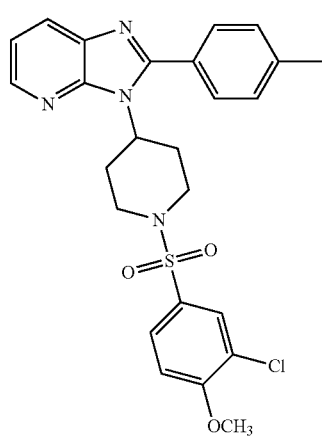 [SMILES: COc1ccc(S(=O)(=O)N2CCC(n3c(-c4ccc(C)cc4)nc4cccnc43)CC2)cc1Cl]

TABLE 4-continued
| Compound No. |
|---|
| 11. 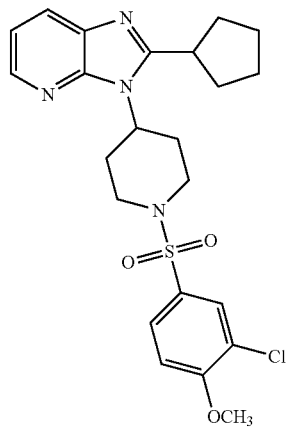 [SMILES: COc1ccc(S(=O)(=O)N2CCC(n3c(C4CCCC4)nc4cccnc43)CC2)cc1Cl] |
| 12. 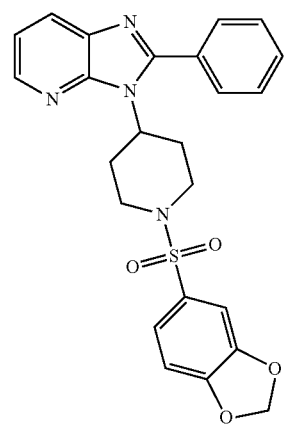 [SMILES: O=S(=O)(c1ccc2c(c1)OCO2)N1CCC(n2c(-c3ccccc3)nc3cccnc32)CC1] |
| 13. 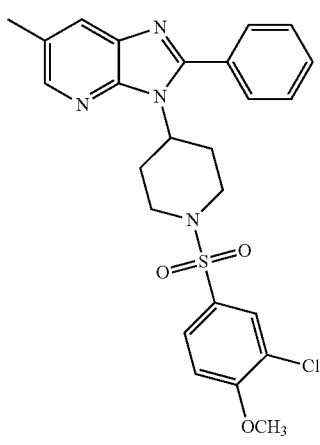 [SMILES: COc1ccc(S(=O)(=O)N2CCC(n3c(-c4ccccc4)nc4cc(C)cnc43)CC2)cc1Cl] |
TABLE 4-continued
| Compound No. |
|---|
| 14. 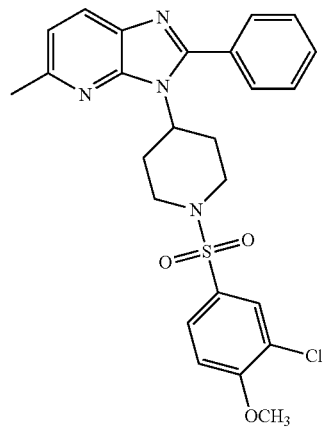 [SMILES: COc1ccc(S(=O)(=O)N2CCC(n3c(-c4ccccc4)nc4ccc(C)nc43)CC2)cc1Cl] |
| 15. 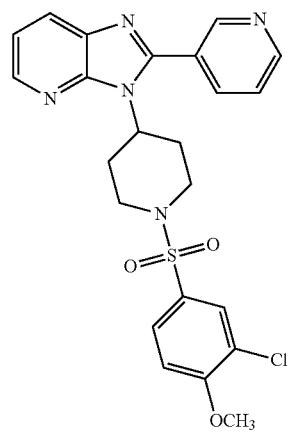 |
| 16. 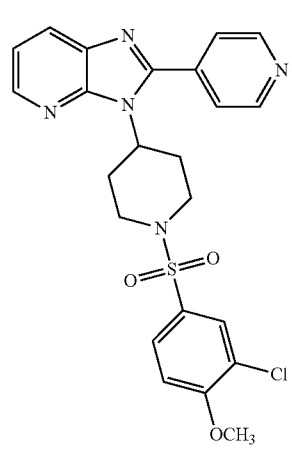 [SMILES: COc1ccc(S(=O)(=O)N2CCC(n3c(-c4ccncc4)nc4cccnc43)CC2)cc1Cl] |

TABLE 4-continued
Compound No.
17.
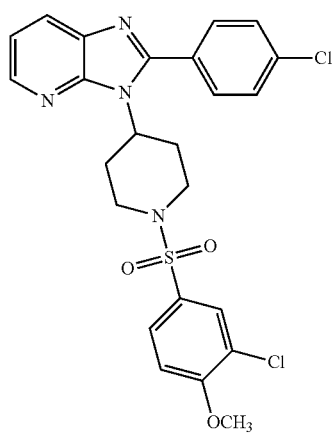 [SMILES: COc1ccc(S(=O)(=O)N2CCC(n3c(-c4ccc(Cl)cc4)nc4cccnc43)CC2)cc1Cl]
18.
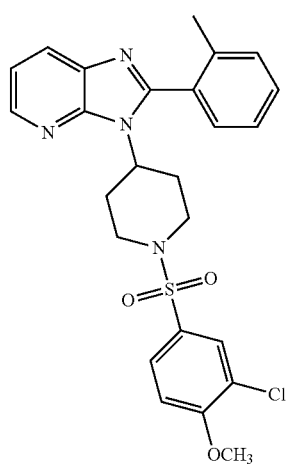 [SMILES: COc1ccc(S(=O)(=O)N2CCC(n3c(-c4ccccc4C)nc4cccnc43)CC2)cc1Cl]
19.
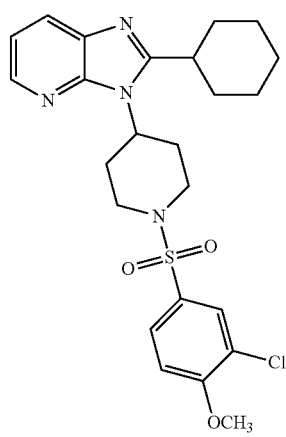 [SMILES: COc1ccc(S(=O)(=O)N2CCC(n3c(C4CCCCC4)nc4cccnc43)CC2)cc1Cl]
TABLE 4-continued
Compound No.
20.
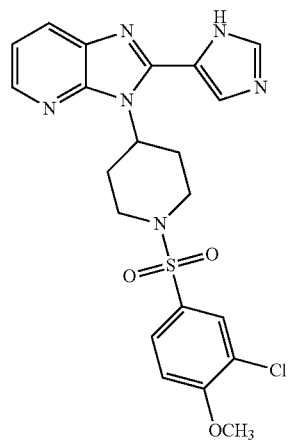 [SMILES: COc1ccc(S(=O)(=O)N2CCC(n3c(-c4cnc[nH]4)nc4cccnc43)CC2)cc1Cl]
21.
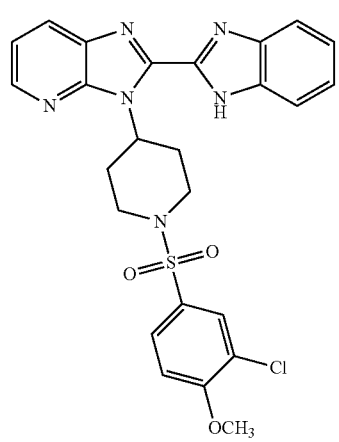 [SMILES: COc1ccc(S(=O)(=O)N2CCC(n3c(-c4nc5ccccc5[nH]4)nc4cccnc43)CC2)cc1Cl]
22.
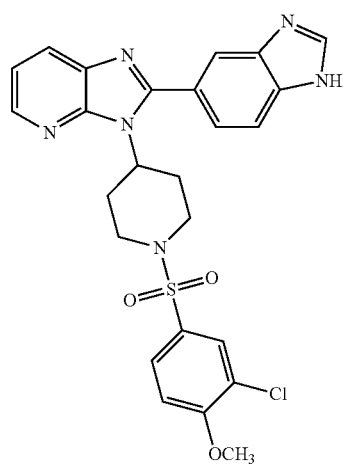 [SMILES: COc1ccc(S(=O)(=O)N2CCC(n3c(-c4ccc5[nH]cnc5c4)nc4cccnc43)CC2)cc1Cl]

TABLE 4-continued
Compound No.
23.
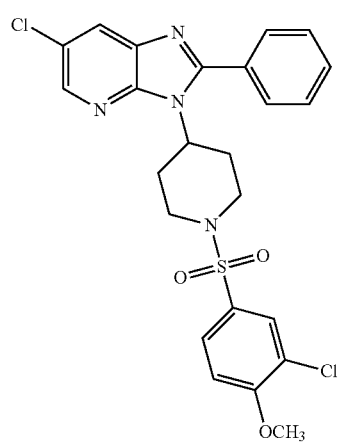 [SMILES: COc1ccc(S(=O)(=O)N2CCC(n3c(-c4ccccc4)nc4cc(Cl)cnc43)CC2)cc1Cl]
24.
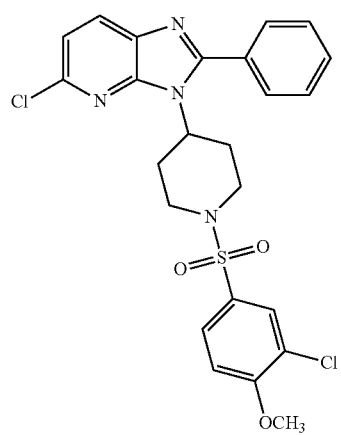 [SMILES: COc1ccc(S(=O)(=O)N2CCC(n3c(-c4ccccc4)nc4ccc(Cl)nc43)CC2)cc1Cl]
25.
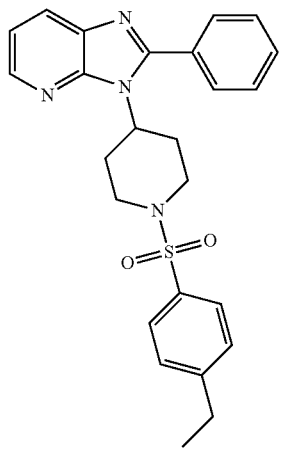 [SMILES: CCc1ccc(S(=O)(=O)N2CCC(n3c(-c4ccccc4)nc4cccnc43)CC2)cc1]
TABLE 4-continued
Compound No.
26.
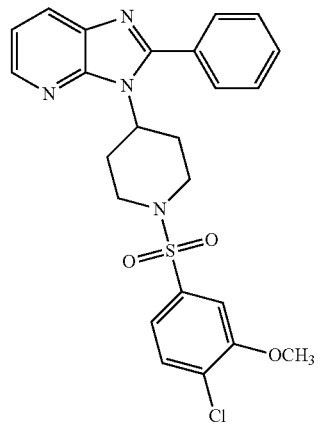 [SMILES: COc1cc(S(=O)(=O)N2CCC(n3c(-c4ccccc4)nc4cccnc43)CC2)ccc1Cl]
27.
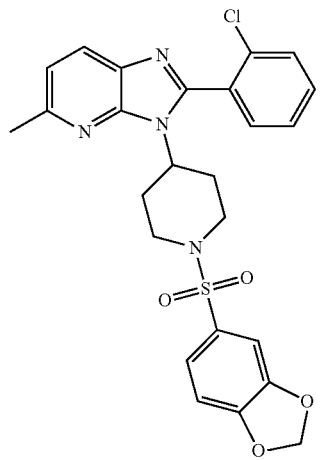 [SMILES: Cc1ccc2nc(-c3ccccc3Cl)n(C3CCN(S(=O)(=O)c4ccc5c(c4)OCO5)CC3)c2n1]
28.
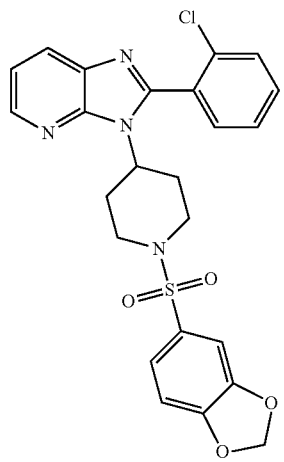 [SMILES: O=S(=O)(c1ccc2c(c1)OCO2)N1CCC(n2c(-c3ccccc3Cl)nc3cccnc32)CC1]

TABLE 4-continued
Compound No.
29.
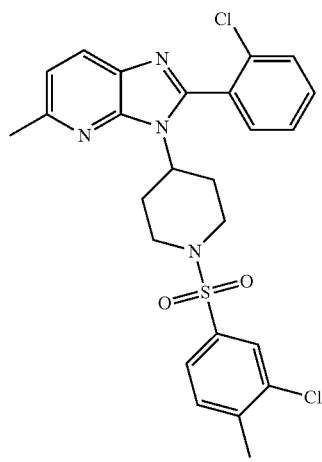 [SMILES: Cc1ccc2nc(-c3ccccc3Cl)n(C3CCN(S(=O)(=O)c4ccc(C)c(Cl)c4)CC3)c2n1]
30.
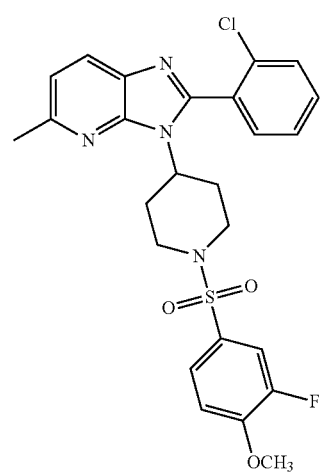 [SMILES: COc1ccc(S(=O)(=O)N2CCC(n3c(-c4ccccc4Cl)nc4ccc(C)nc43)CC2)cc1F]
31.
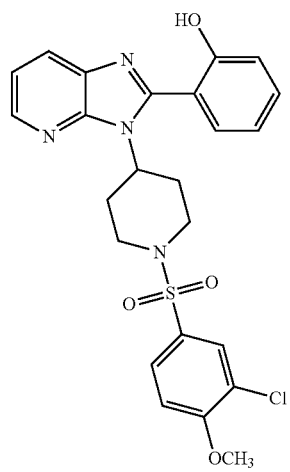
TABLE 4-continued
Compound No.
32.
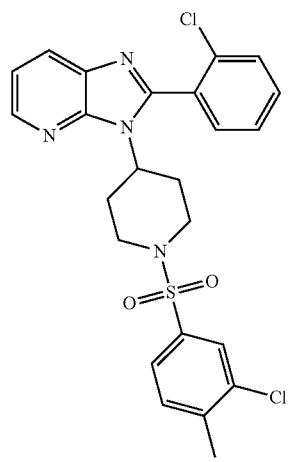 [SMILES: Cc1ccc(S(=O)(=O)N2CCC(n3c(-c4ccccc4Cl)nc4cccnc43)CC2)cc1Cl]
33.
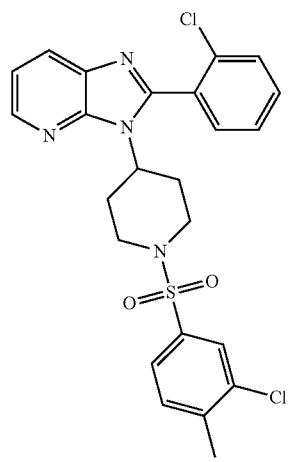 [SMILES: Cc1ccc(S(=O)(=O)N2CCC(n3c(-c4ccccc4Cl)nc4cccnc43)CC2)cc1Cl]
34.
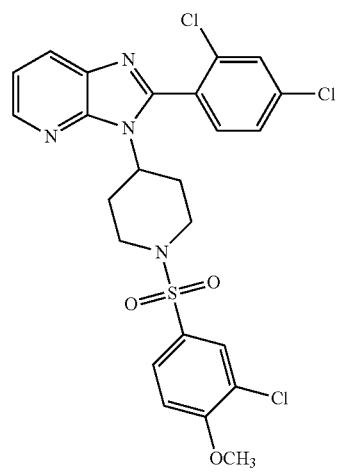 [SMILES: COc1ccc(S(=O)(=O)N2CCC(n3c(-c4ccc(Cl)cc4Cl)nc4cccnc43)CC2)cc1Cl]

TABLE 4-continued

Compound No.

35. 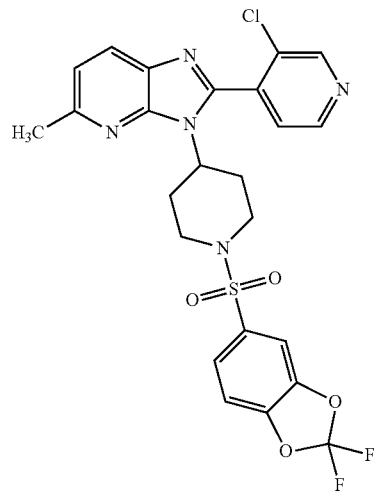 [SMILES: Cc1ccc2nc(-c3ccncc3Cl)n(C3CCN(S(=O)(=O)c4ccc5c(c4)OC(F)(F)O5)CC3)c2n1]

36. 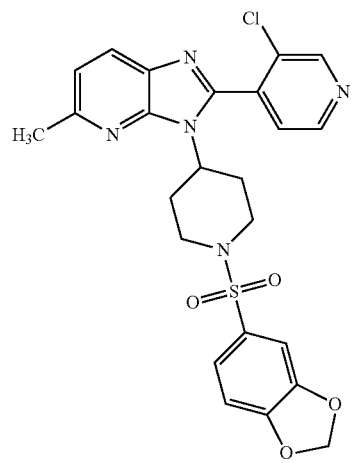 [SMILES: Cc1ccc2nc(-c3ccncc3Cl)n(C3CCN(S(=O)(=O)c4ccc5c(c4)OCO5)CC3)c2n1]

37. 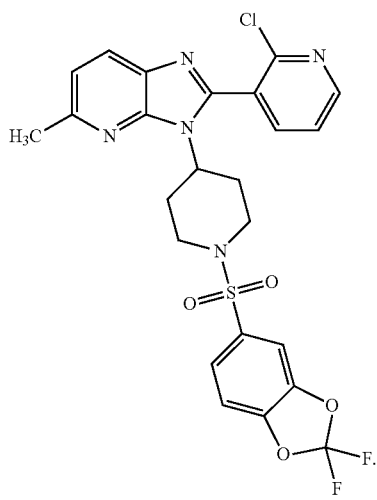 [SMILES: Cc1ccc2nc(-c3cccnc3Cl)n(C3CCN(S(=O)(=O)c4ccc5c(c4)OC(F)(F)O5)CC3)c2n1]

3. The pharmaceutical composition of claim 1, wherein Cy₂ is selected from the group consisting of:

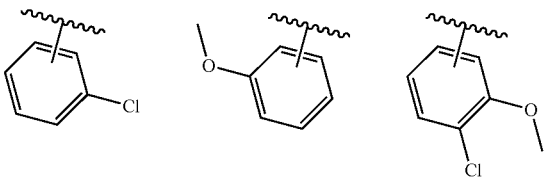

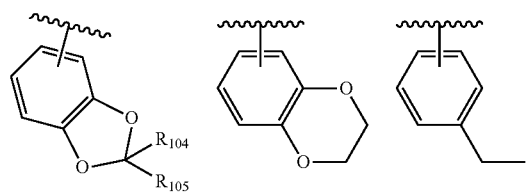

and

4. The pharmaceutical composition of claim 1, wherein Cy₁ is

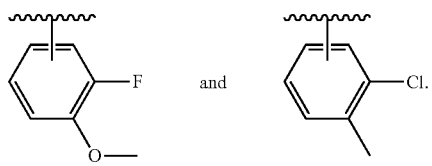

5. The pharmaceutical composition of claim 1, wherein Cy₂ is

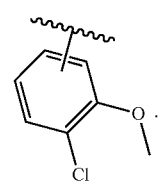

6. The pharmaceutical composition of claim 1, wherein the compound of Formula V is selected from the table below, or a pharmaceutically acceptable salt thereof:

TABLE 4
| Compound No. |
|---|
| 1. 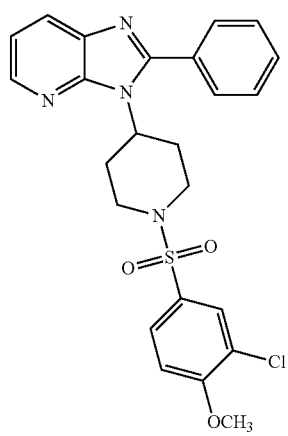 |
| 2. 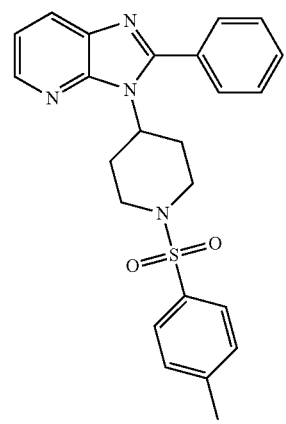 [SMILES: Cc1ccc(S(=O)(=O)N2CCC(n3c(-c4ccccc4)nc4cccnc43)CC2)cc1] |
| 7. 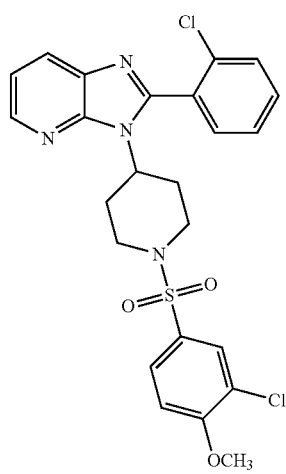 [SMILES: COc1ccc(S(=O)(=O)N2CCC(n3c(-c4ccccc4Cl)nc4cccnc43)CC2)cc1Cl] |
TABLE 4-continued
| Compound No. |
|---|
| 12. 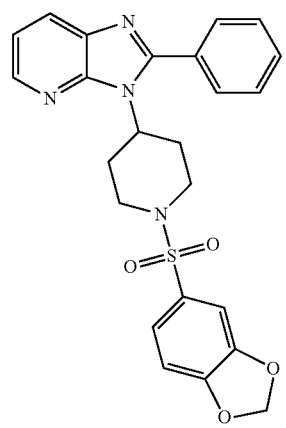 [SMILES: O=S(=O)(c1ccc2c(c1)OCO2)N1CCC(n2c(-c3ccccc3)nc3cccnc32)CC1] |
| 13. 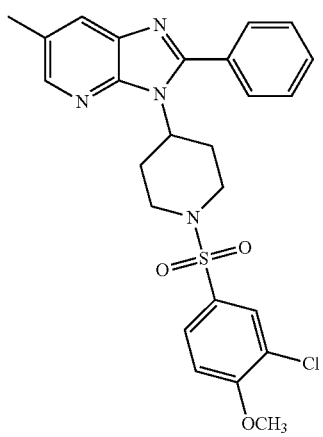 [SMILES: COc1ccc(S(=O)(=O)N2CCC(n3c(-c4ccccc4)nc4cc(C)cnc43)CC2)cc1Cl] |
| 14. 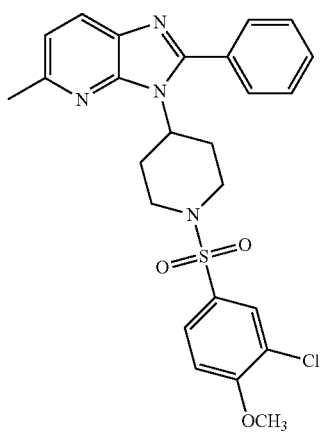 |

TABLE 4-continued
Compound No.
15.
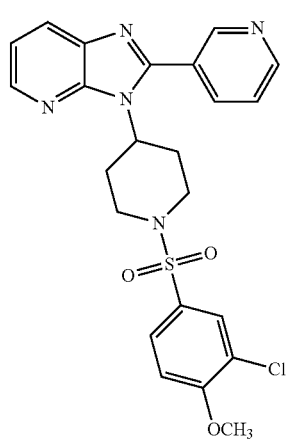
16.
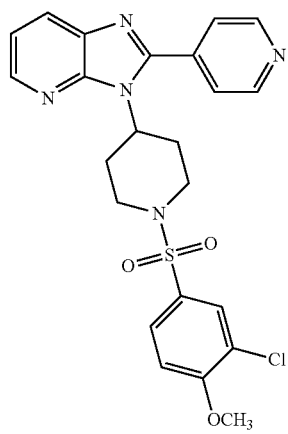
20.
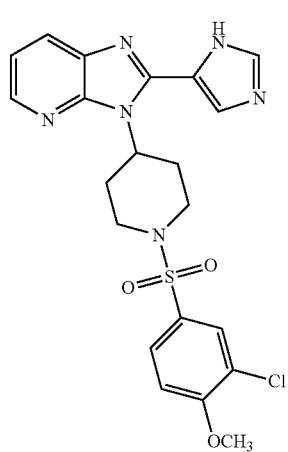 [SMILES: COc1ccc(S(=O)(=O)N2CCC(n3c(-c4cnc[nH]4)nc4cccnc43)CC2)cc1Cl]
TABLE 4-continued
Compound No.
25.
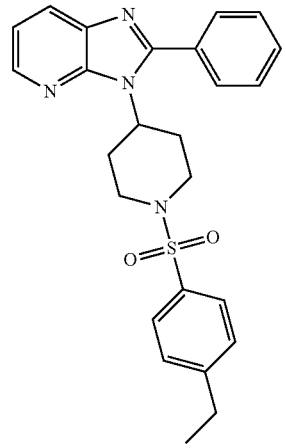 [SMILES: CCc1ccc(S(=O)(=O)N2CCC(n3c(-c4ccccc4)nc4cccnc43)CC2)cc1]
27.
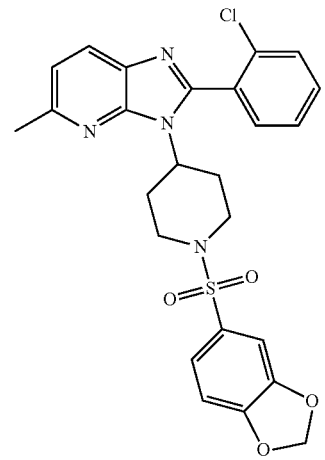 [SMILES: Cc1ccc2nc(-c3ccccc3Cl)n(C3CCN(S(=O)(=O)c4ccc5c(c4)OCO5)CC3)c2n1]
28.
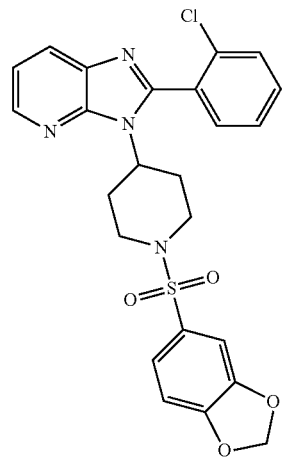 [SMILES: O=S(=O)(c1ccc2c(c1)OCO2)N1CCC(n2c(-c3ccccc3Cl)nc3cccnc32)CC1]

TABLE 4-continued
Compound No.
29. 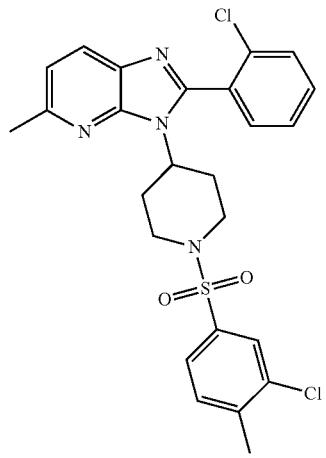 [SMILES: Cc1ccc2nc(-c3ccccc3Cl)n(C3CCN(S(=O)(=O)c4ccc(C)c(Cl)c4)CC3)c2n1]
30. 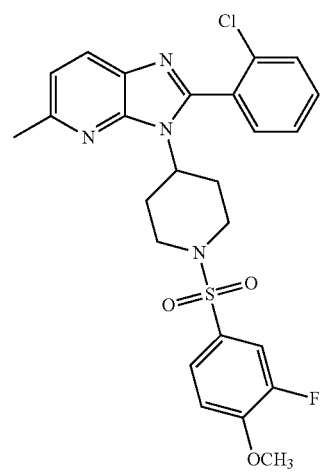 [SMILES: COc1ccc(S(=O)(=O)N2CCC(n3c(-c4ccccc4Cl)nc4ccc(C)nc43)CC2)cc1F]
31. 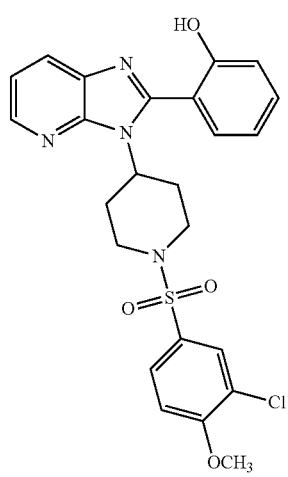
TABLE 4-continued
Compound No.
33. 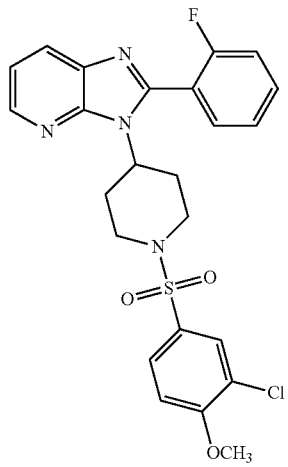
34. 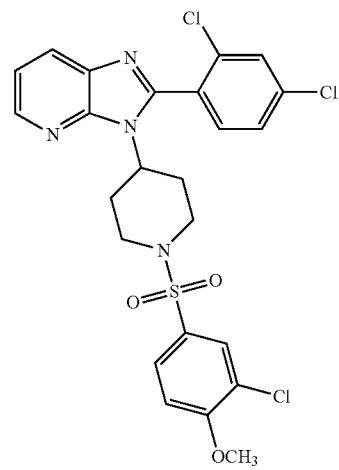 [SMILES: COc1ccc(S(=O)(=O)N2CCC(n3c(-c4ccc(Cl)cc4Cl)nc4cccnc43)CC2)cc1Cl]
35. 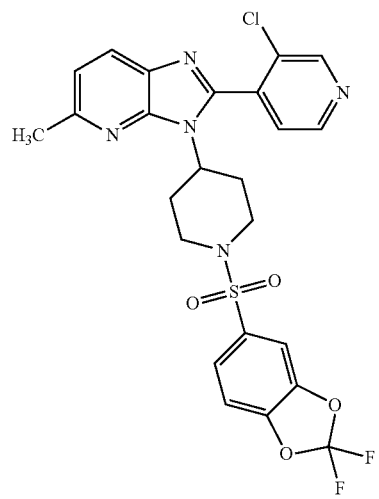 [SMILES: Cc1ccc2nc(-c3ccncc3Cl)n(C3CCN(S(=O)(=O)c4ccc5c(c4)OC(F)(F)O5)CC3)c2n1]

121
TABLE 4-continued

Compound No.

36.

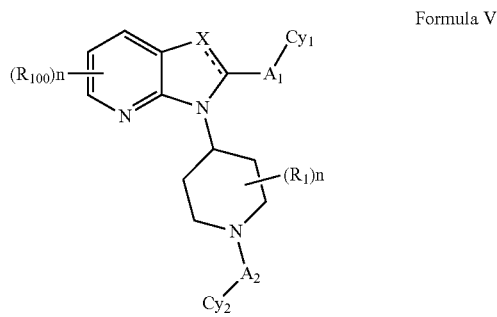

37.

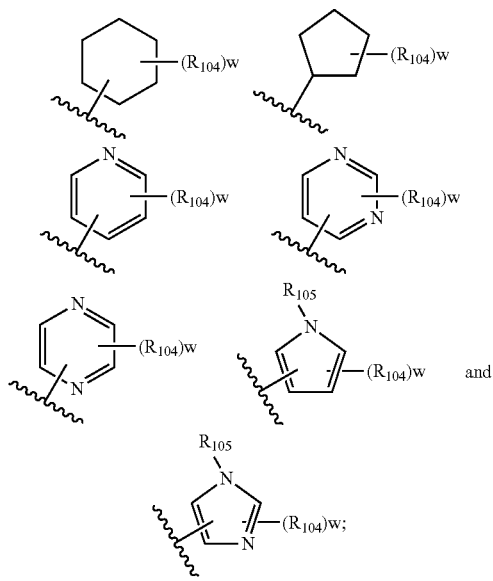

7. The pharmaceutical composition of claim 1 in the form of a sterile injectable aqueous or oleaginous suspension, a capsule, or a tablet.

8. The pharmaceutical composition of claim 2 in the form of a sterile injectable aqueous or oleaginous suspension, a capsule, or a tablet.

9. A method for treating cystic fibrosis or a symptom thereof in a subject in need thereof, comprising the step of administering to the subject a therapeutically effective amount of the pharmaceutical composition of claim 1.

10. A method of treating cystic fibrosis or a symptom thereof in a subject in need thereof, comprising the step of administering to the subject a therapeutically effective amount of the pharmaceutical composition of claim 2.

122

11. A compound of Formula V:

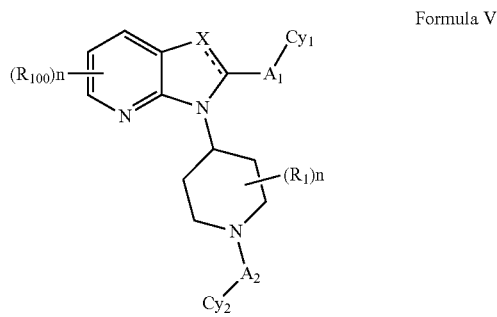

Formula V or a pharmaceutically acceptable salt, or ester thereof;
wherein
each n is independently 0, 1, 2, or 3;
X is N;
$A_1$ is absent;
$A_2$ is —S(O)$_2$—;
$Cy_1$ is selected from:

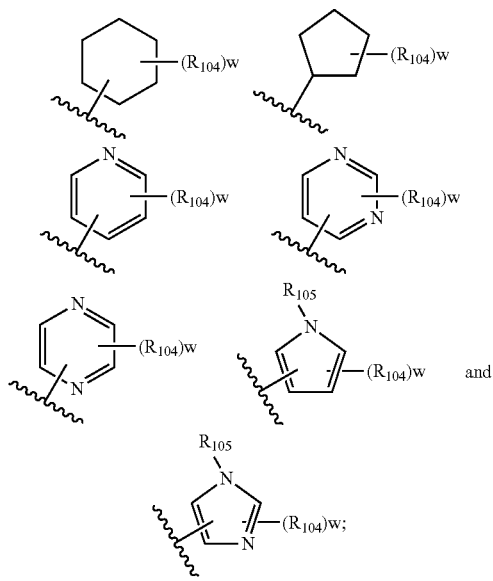

wherein w is 0 to 4;
or $Cy_1$ is

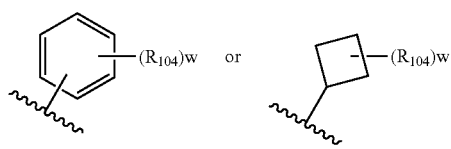

wherein w is 1 to 4;
each $R_{104}$ is independently selected from deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —OR$_{100}$, —SR$_{100}$, —S(O), —S(O)$_2$—, —S(O)$_2$N(R$_{100}$)(R$_{101}$) —NR$_{100}$R$_{101}$, —C(O)R$_{100}$, —C(O)OR$_{100}$, —C(O)NR$_{100}$R$_{101}$, —N(R$_{100}$)C(O)R$_{101}$, —CF$_3$, —CN, —NO$_2$, —N$_3$, acyl, alkoxy, substituted alkoxy, alkylamino, substituted alkylamino, dialkylamino, substituted dialkylamino, alkylthio and substituted alkylthio;

R$_{105}$ is selected from hydrogen, deuterium, halogen, alkyl, cycloalkyl, substituted alkyl, alkenyl, substituted alkenyl, alkynyl, substituted alkynyl, aliphatic, substituted aliphatic, aryl, substituted aryl, heterocycle, substituted heterocycle, heteroaryl, or substituted heteroaryl —OR$_{100}$, —SR$_{100}$, —S(O), —S(O)$_2$—, —S(O)$_2$N(R$_{100}$)(R$_{101}$) —NR$_{100}$R$_{101}$, —C(O)R$_{100}$, —C(O)OR$_{100}$, —C(O)NR$_{100}$R$_{101}$, —N(R$_{100}$)C(O)R$_{101}$, —CF$_3$, —CN, —NO$_2$, —N$_3$, acyl, alkoxy, substituted alkoxy, alkylamino, substituted alkylamino, dialkylamino, substituted dialkylamino, alkylthio and substituted alkylthio;

alternatively, two R$_{104}$ groups or an R$_{104}$ group with an R$_{105}$ group, together with the atoms to which they are attached and any intervening atoms, form an additional optionally substituted 3, 4, 5, 6 or 7 membered ring;

R$_{100}$ and R$_{100}$ are each independently hydrogen, deuterium, halogen, alkyl, cycloalkyl, substituted alkyl, alkenyl, substituted alkenyl, alkynyl, substituted alkynyl, aliphatic, substituted aliphatic, aryl and substituted aryl, heterocycle, substituted heterocycle, heteroaryl or substituted heteroaryl; alternatively, R$_{100}$ and R$_{101}$ together with the atoms to which they are attached and any intervening atoms form an optionally substituted, 3, 4, 5, 6 or 7 membered ring; and Cy$_2$ is substituted or unsubstituted phenyl.

12. The compound of claim 11, wherein Cy$_2$ is phenyl or

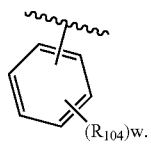

13. The compound of claim 12, wherein Cy$_2$ is selected from:

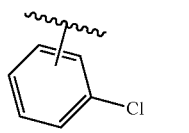 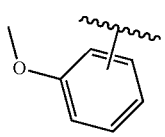 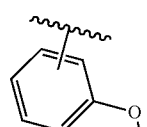

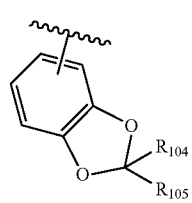 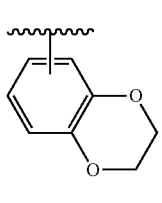 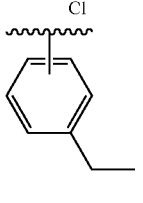

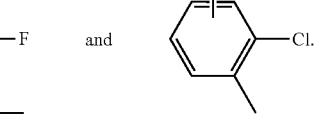 and 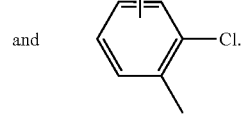

14. The compound of claim 13, wherein Cy$_2$ is

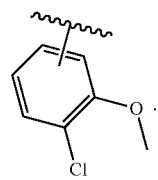

15. A compound selected from the compounds set forth in the table below, or a pharmaceutically acceptable salt thereof:

3.

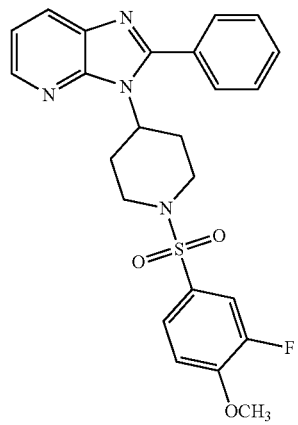 [SMILES: COc1ccc(S(=O)(=O)N2CCC(n3c(-c4ccccc4)nc4cccnc43)CC2)cc1F]

4.

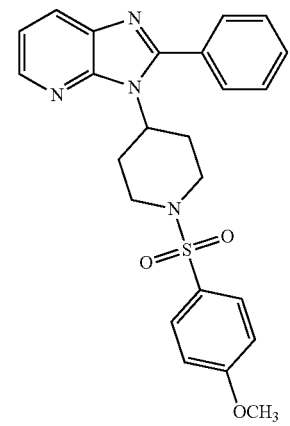 [SMILES: COc1ccc(S(=O)(=O)N2CCC(n3c(-c4ccccc4)nc4cccnc43)CC2)cc1]

5.

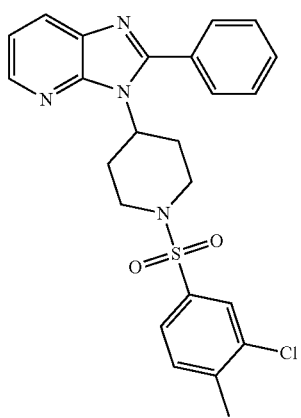 [SMILES: Cc1ccc(S(=O)(=O)N2CCC(n3c(-c4ccccc4)nc4cccnc43)CC2)cc1Cl]

-continued
7.
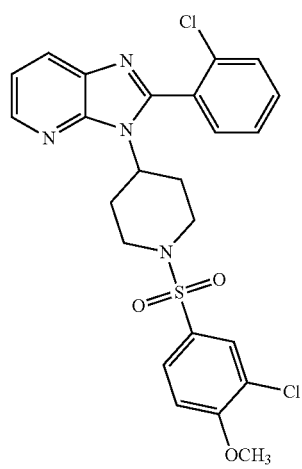 [SMILES: COc1ccc(S(=O)(=O)N2CCC(n3c(-c4ccccc4Cl)nc4cccnc43)CC2)cc1Cl]
8.
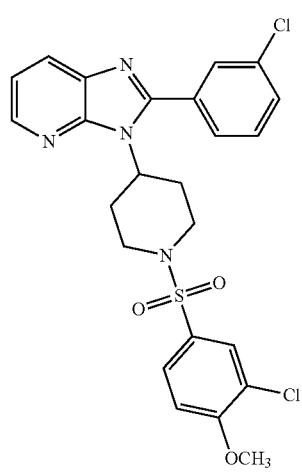 [SMILES: COc1ccc(S(=O)(=O)N2CCC(n3c(-c4cccc(Cl)c4)nc4cccnc43)CC2)cc1Cl]
9.
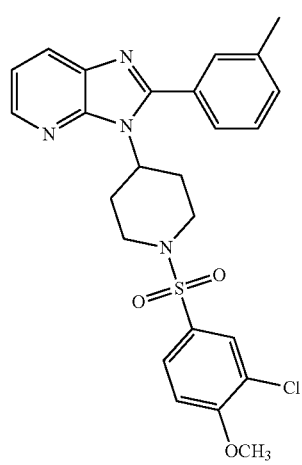 [SMILES: COc1ccc(S(=O)(=O)N2CCC(n3c(-c4cccc(C)c4)nc4cccnc43)CC2)cc1Cl]
-continued
10.
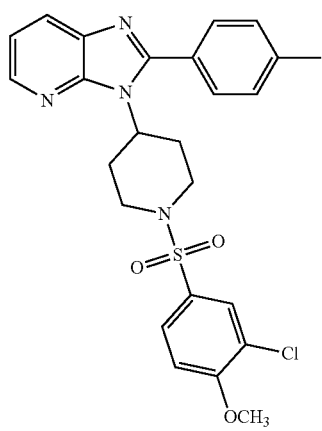 [SMILES: COc1ccc(S(=O)(=O)N2CCC(n3c(-c4ccc(C)cc4)nc4cccnc43)CC2)cc1Cl]
11.
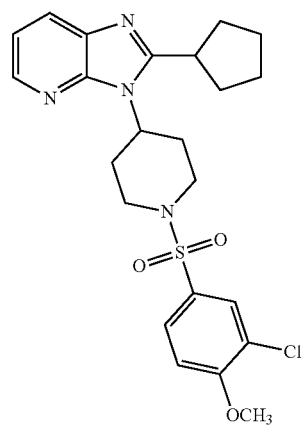 [SMILES: COc1ccc(S(=O)(=O)N2CCC(n3c(C4CCCC4)nc4cccnc43)CC2)cc1Cl]
12.
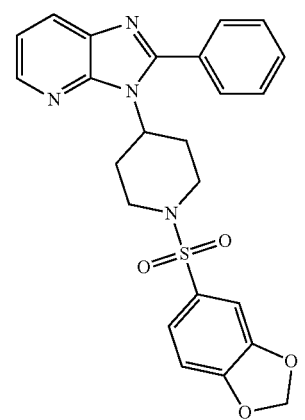 [SMILES: O=S(=O)(c1ccc2c(c1)OCO2)N1CCC(n2c(-c3ccccc3)nc3cccnc32)CC1]

13.
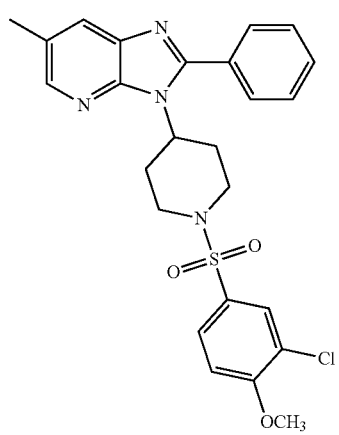 [SMILES: COc1ccc(S(=O)(=O)N2CCC(n3c(-c4ccccc4)nc4cc(C)cnc43)CC2)cc1Cl]
14.
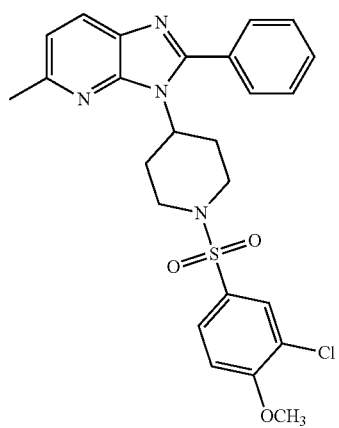 [SMILES: COc1ccc(S(=O)(=O)N2CCC(n3c(-c4ccccc4)nc4ccc(C)nc43)CC2)cc1Cl]
15.
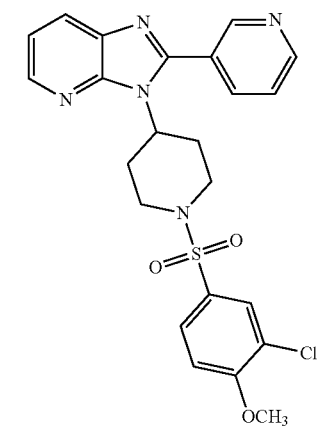 [SMILES: COc1ccc(S(=O)(=O)N2CCC(n3c(-c4cccnc4)nc4cccnc43)CC2)cc1Cl]
16.
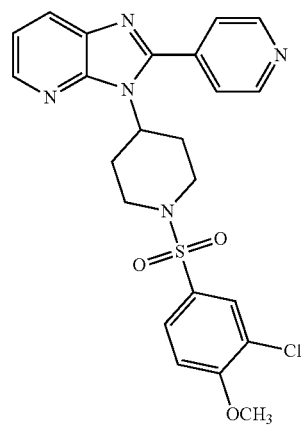 [SMILES: COc1ccc(S(=O)(=O)N2CCC(n3c(-c4ccncc4)nc4cccnc43)CC2)cc1Cl]
17.
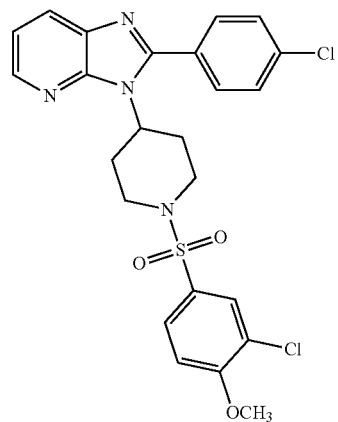 [SMILES: COc1ccc(S(=O)(=O)N2CCC(n3c(-c4ccc(Cl)cc4)nc4cccnc43)CC2)cc1Cl]
18.
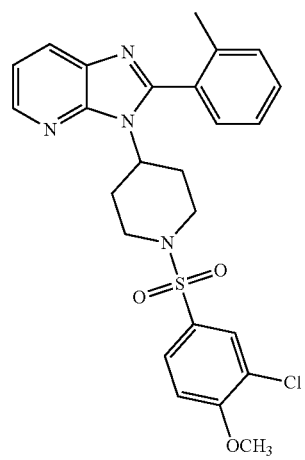 [SMILES: COc1ccc(S(=O)(=O)N2CCC(n3c(-c4ccccc4C)nc4cccnc43)CC2)cc1Cl]

19.
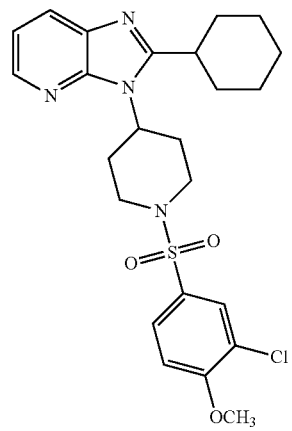 [SMILES: COc1ccc(S(=O)(=O)N2CCC(n3c(C4CCCCC4)nc4cccnc43)CC2)cc1Cl]
20.
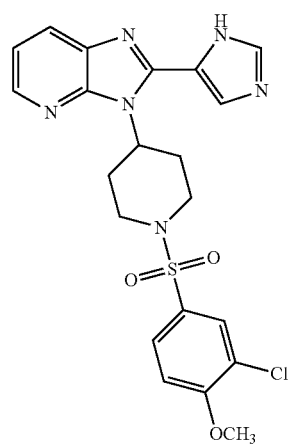 [SMILES: COc1ccc(S(=O)(=O)N2CCC(n3c(-c4cnc[nH]4)nc4cccnc43)CC2)cc1Cl]
21.
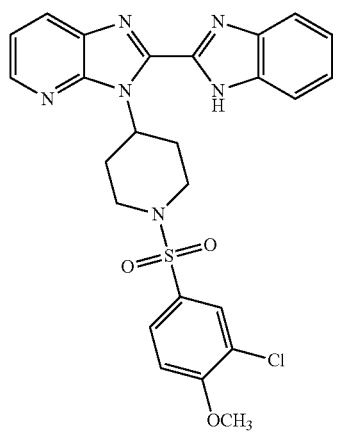 [SMILES: COc1ccc(S(=O)(=O)N2CCC(n3c(-c4nc5ccccc5[nH]4)nc4cccnc43)CC2)cc1Cl]
22.
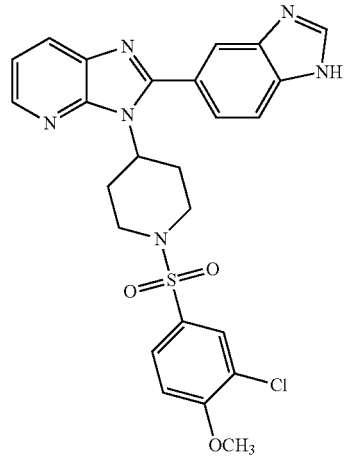 [SMILES: COc1ccc(S(=O)(=O)N2CCC(n3c(-c4ccc5[nH]cnc5c4)nc4cccnc43)CC2)cc1Cl]
23.
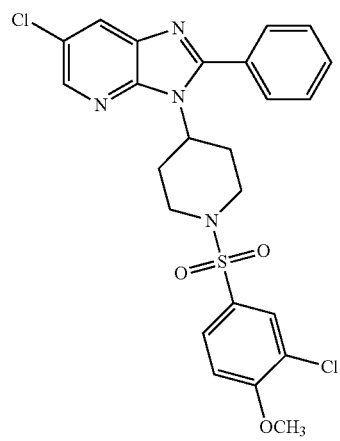 [SMILES: COc1ccc(S(=O)(=O)N2CCC(n3c(-c4ccccc4)nc4cc(Cl)cnc43)CC2)cc1Cl]
24.
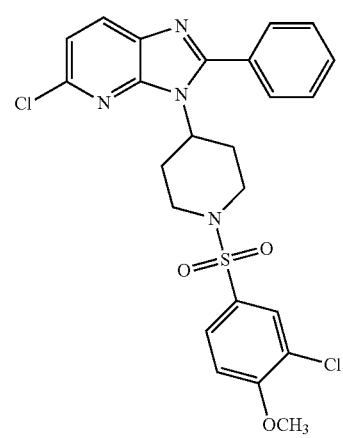 [SMILES: COc1ccc(S(=O)(=O)N2CCC(n3c(-c4ccccc4)nc4ccc(Cl)nc43)CC2)cc1Cl]

25.
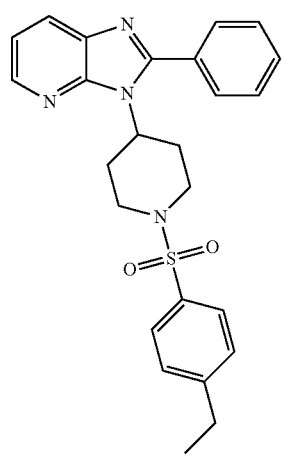 [SMILES: CCc1ccc(S(=O)(=O)N2CCC(n3c(-c4ccccc4)nc4cccnc43)CC2)cc1]
26.
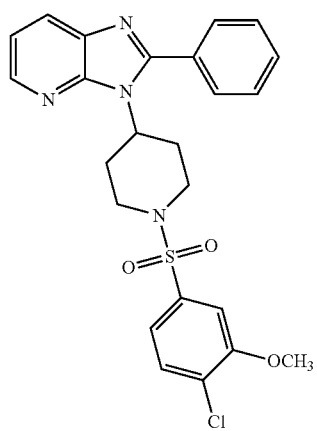 [SMILES: COc1cc(S(=O)(=O)N2CCC(n3c(-c4ccccc4)nc4cccnc43)CC2)ccc1Cl]
27.
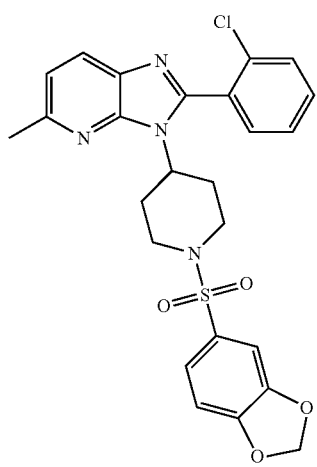 [SMILES: Cc1ccc2nc(-c3ccccc3Cl)n(C3CCN(S(=O)(=O)c4ccc5c(c4)OCO5)CC3)c2n1]
28.
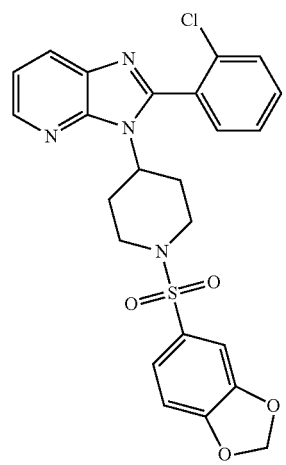 [SMILES: O=S(=O)(c1ccc2c(c1)OCO2)N1CCC(n2c(-c3ccccc3Cl)nc3cccnc32)CC1]
29.
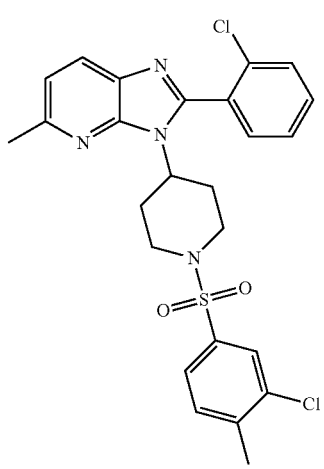 [SMILES: Cc1ccc2nc(-c3ccccc3Cl)n(C3CCN(S(=O)(=O)c4ccc(C)c(Cl)c4)CC3)c2n1]
30.
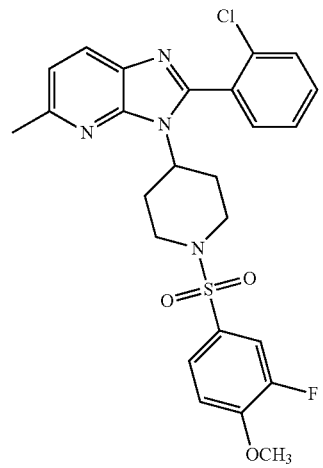 [SMILES: COc1ccc(S(=O)(=O)N2CCC(n3c(-c4ccccc4Cl)nc4ccc(C)nc43)CC2)cc1F]

-continued
31.
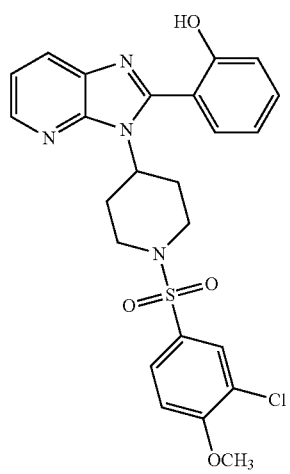
32.
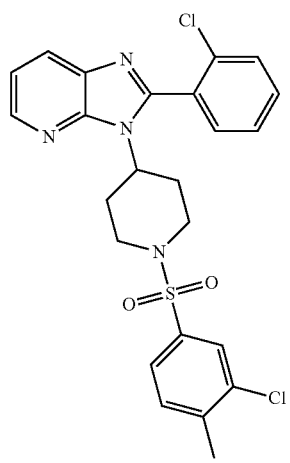 [SMILES: Cc1ccc(S(=O)(=O)N2CCC(n3c(-c4ccccc4Cl)nc4cccnc43)CC2)cc1Cl]
33.
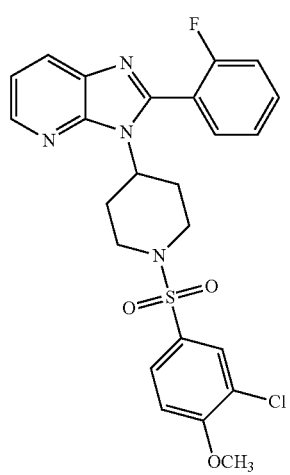
-continued
34.
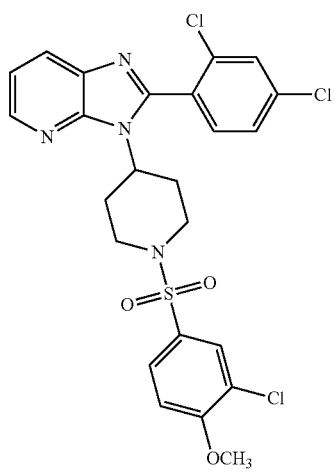 [SMILES: COc1ccc(S(=O)(=O)N2CCC(n3c(-c4ccc(Cl)cc4Cl)nc4cccnc43)CC2)cc1Cl]
35.
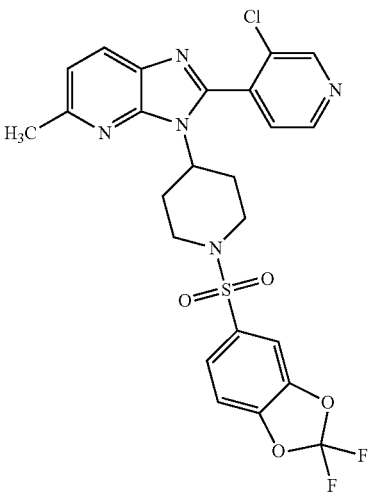 [SMILES: Cc1ccc2nc(-c3ccncc3Cl)n(C3CCN(S(=O)(=O)c4ccc5c(c4)OC(F)(F)O5)CC3)c2n1]
36.

37. 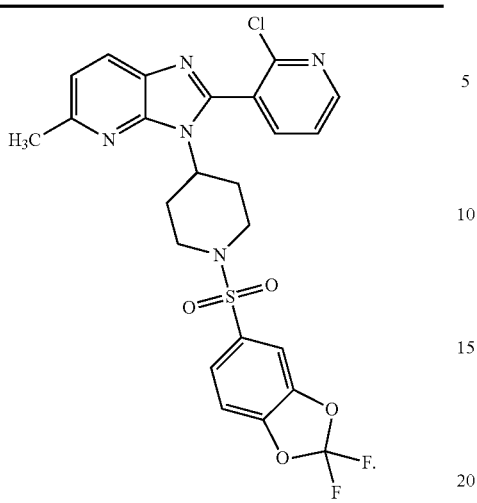
* * * * *